US008865188B2

(12) United States Patent
de los Rios et al.

(10) Patent No.: US 8,865,188 B2
(45) Date of Patent: Oct. 21, 2014

(54) METHODS AND COMPOSITIONS FOR CONTROLLING ASSEMBLY OF VIRAL PROTEINS

(75) Inventors: Miguel de los Rios, Del Mar, CA (US); Stephanie de los Rios, Del Mar, CA (US); Jacek Ostrowski, Encinitas, CA (US); Kenneth J. Oh, Pleasant Hill, CA (US); Ilan Zipkin, Belmont, CA (US)

(73) Assignee: Biomed Realty, L.P., San Diego, CA (US)

( * ) Notice: Subject to any disclaimer, the term of this patent is extended or adjusted under 35 U.S.C. 154(b) by 0 days.

(21) Appl. No.: 13/609,234

(22) Filed: Sep. 10, 2012

(65) Prior Publication Data

US 2013/0156818 A1  Jun. 20, 2013

Related U.S. Application Data

(60) Provisional application No. 61/532,986, filed on Sep. 9, 2011.

(51) Int. Cl.

| | | |
|---|---|---|
| *C07K 1/113* | (2006.01) | |
| *A61K 9/51* | (2006.01) | |
| *C07K 1/107* | (2006.01) | |
| *A61K 38/16* | (2006.01) | |
| *C07K 14/005* | (2006.01) | |

(52) U.S. Cl.
CPC ............ *C07K 1/1133* (2013.01); *A61K 38/162* (2013.01); *C07K 1/1075* (2013.01); *C07K 1/1072* (2013.01); *C07K 14/005* (2013.01); *C07K 1/1077* (2013.01); *C12N 2730/10122* (2013.01); *C07K 1/1136* (2013.01); *A61K 9/5184* (2013.01)
USPC ........... 424/400; 530/402; 530/408; 530/410; 530/358; 514/1.1; 514/773

(58) Field of Classification Search
CPC .............. A61K 2039/6075; A61K 2039/5258; A61K 39/12; A61K 39/29; A61K 9/5184; A61K 38/162; C07K 14/005; C07K 2319/735; C07K 2319/85
See application file for complete search history.

(56) References Cited

U.S. PATENT DOCUMENTS

| | | | |
|---|---|---|---|
| 5,133,961 A | 7/1992 | Ellis et al. | |
| 5,420,026 A | 5/1995 | Payne | |

(Continued)

FOREIGN PATENT DOCUMENTS

| | | |
|---|---|---|
| EP | 0863987 A2 | 9/1998 |
| EP | 0920514 B1 | 6/1999 |

(Continued)

OTHER PUBLICATIONS

Birnbaum et al. Hepatitis B virus nucleocapsid assembly: primary structure requirements in the core protein. J Virol. Jul. 1990;64(7):3319-30.*

(Continued)

*Primary Examiner* — Karlheinz R Skowronek
*Assistant Examiner* — Jia-Hai Lee
(74) *Attorney, Agent, or Firm* — Goodwin Procter LLP

(57) ABSTRACT

Provided herein are methods and compositions for controlling assembly of modified viral core proteins, for example, into a viral capsid or a nanocage. In some embodiments, the disclosed modified viral core proteins comprise at least one mutation or modification that can substantially prevent assembly of the viral core proteins until assembly is desired. In some embodiments, assembly of the viral core proteins may be triggered, for example, by contacting the viral core proteins with a reducing agent and/or by reducing the concentration of a denaturant. The viral core proteins may self-assemble to form a viral capsid or a nanocage.

32 Claims, 11 Drawing Sheets

(56) References Cited

U.S. PATENT DOCUMENTS

| | | | |
|---|---|---|---|
| 5,439,686 A | 8/1995 | Desai et al. |
| 5,498,421 A | 3/1996 | Grinstaff et al. |
| 5,620,689 A | 4/1997 | Allen et al. |
| 5,670,630 A | 9/1997 | Thill |
| 5,714,316 A | 2/1998 | Weiner et al. |
| 5,858,726 A | 1/1999 | Payne |
| 5,863,541 A | 1/1999 | Samulski et al. |
| 5,980,901 A | 11/1999 | Shih et al. |
| 6,046,173 A | 4/2000 | Forstova et al. |
| 6,063,370 A | 5/2000 | Dadey |
| 6,096,331 A | 8/2000 | Desai et al. |
| 6,204,059 B1 | 3/2001 | Samulski et al. |
| 6,231,864 B1 | 5/2001 | Birkett |
| 6,287,857 B1 | 9/2001 | O'Riordan et al. |
| 6,387,662 B1 | 5/2002 | Liang et al. |
| 6,420,160 B1 | 7/2002 | Bloch |
| 6,506,405 B1 | 1/2003 | Desai et al. |
| 6,506,559 B1 | 1/2003 | Fire et al. |
| 6,537,579 B1 | 3/2003 | Desai et al. |
| 6,573,009 B1 | 6/2003 | Noda et al. |
| 6,593,308 B2 | 7/2003 | Szoka, Jr. |
| 6,602,706 B1 | 8/2003 | Fallaux et al. |
| 6,602,932 B2 | 8/2003 | Feldheim et al. |
| 6,616,944 B2 | 9/2003 | Kissel et al. |
| 6,620,617 B2 | 9/2003 | Mathiowitz et al. |
| 6,627,202 B2 | 9/2003 | Murray et al. |
| 6,696,038 B1 | 2/2004 | Mahato et al. |
| 6,710,173 B1 | 3/2004 | Binley et al. |
| 6,749,868 B1 | 6/2004 | Desai et al. |
| 6,753,006 B1 | 6/2004 | Desai et al. |
| 6,984,386 B2 | 1/2006 | Douglas et al. |
| 7,056,704 B2 | 6/2006 | Tuschl et al. |
| 7,078,194 B2 | 7/2006 | Withers et al. |
| 7,101,995 B2 | 9/2006 | Lewis et al. |
| 7,148,342 B2 | 12/2006 | Tolentino et al. |
| 7,148,343 B2 | 12/2006 | Bair, Jr. et al. |
| 7,282,199 B2 | 10/2007 | Gao et al. |
| 7,332,321 B2 | 2/2008 | Belcher et al. |
| 7,332,337 B2 | 2/2008 | van Es et al. |
| 7,344,872 B2 | 3/2008 | Gao et al. |
| 7,365,978 B2 | 4/2008 | Chen et al. |
| 7,422,902 B1 | 9/2008 | Wheeler et al. |
| 7,964,196 B2 | 6/2011 | de los Rios et al. |
| 8,067,011 B2 | 11/2011 | Davis et al. |
| 2003/0153081 A1 | 8/2003 | Tagawa et al. |
| 2004/0005338 A1 | 1/2004 | Bachmann et al. |
| 2004/0247660 A1 | 12/2004 | Singh |
| 2005/0004002 A1 | 1/2005 | Desai et al. |
| 2005/0089526 A1 | 4/2005 | Moore et al. |
| 2006/0292118 A1 | 12/2006 | Kuroda et al. |
| 2006/0292174 A1 | 12/2006 | de los Rios et al. |
| 2007/0160628 A1* | 7/2007 | Birkett et al. ............... 424/204.1 |
| 2007/0248573 A1 | 10/2007 | Sturino |
| 2007/0249554 A1 | 10/2007 | Tuszynski |
| 2007/0258889 A1 | 11/2007 | Douglas et al. |
| 2007/0269370 A1 | 11/2007 | Davis et al. |
| 2007/0280962 A1 | 12/2007 | Murray |
| 2008/0050343 A1 | 2/2008 | Wilson et al. |
| 2008/0050345 A1 | 2/2008 | Wilson et al. |
| 2008/0069802 A1 | 3/2008 | Davis et al. |
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0125385 A1 | 5/2008 | Hajjar et al. |
| 2008/0131928 A1 | 6/2008 | Handa et al. |
| 2009/0226525 A1 | 9/2009 | de los Rios et al. |
| 2011/0293725 A1 | 12/2011 | de los Rios et al. |
| 2011/0293726 A1 | 12/2011 | de los Rios et al. |
| 2011/0293727 A1 | 12/2011 | de los Rios et al. |
| 2011/0293733 A1 | 12/2011 | de los Rios et al. |
| 2012/0315335 A1 | 12/2012 | de los Rios et al. |
| 2013/0156818 A1 | 6/2013 | de los Rios et al. |
| 2014/0010885 A1 | 1/2014 | de los Rios et al. |

FOREIGN PATENT DOCUMENTS

| | | |
|---|---|---|
| EP | 1204761 B1 | 5/2002 |
| EP | 1219705 A1 | 7/2002 |
| EP | 1447079 A1 | 8/2004 |
| EP | 1563834 A1 | 8/2005 |
| EP | 1845163 A2 | 10/2007 |
| EP | 1849799 A1 | 10/2007 |
| EP | 1944043 A1 | 7/2008 |
| WO | WO-95/32706 A1 | 12/1995 |
| WO | WO-99/40214 A2 | 8/1999 |
| WO | WO-00/09158 A1 | 2/2000 |
| WO | WO-01/02551 A2 | 1/2001 |
| WO | WO-01/12235 A2 | 2/2001 |
| WO | WO-02/44204 A2 | 6/2002 |
| WO | WO-2004/047812 A1 | 6/2004 |
| WO | WO-2006/033679 A2 | 3/2006 |
| WO | WO-2006/066048 A2 | 6/2006 |
| WO | WO-2007/126764 A2 | 11/2007 |
| WO | WO-2007/136263 A1 | 11/2007 |
| WO | WO-2008/010864 A2 | 1/2008 |
| WO | WO-2008/021908 A2 | 2/2008 |
| WO | WO-2008/024427 A2 | 2/2008 |
| WO | WO-2008/027084 A2 | 3/2008 |
| WO | WO-2008/037504 A1 | 4/2008 |
| WO | WO-2008/048288 A2 | 4/2008 |
| WO | WO-2008/051101 A1 | 5/2008 |
| WO | WO-2008/054826 A2 | 5/2008 |
| WO | WO-2008/124165 A2 | 10/2008 |
| WO | WO 2008/124165 A2 * | 10/2008 ............. C07K 14/02 |
| WO | WO-2010/042749 A2 | 4/2010 |
| WO | WO-2010/042751 A2 | 4/2010 |
| WO | WO-2010/042755 A2 | 4/2010 |
| WO | WO-2010/120874 A2 | 10/2010 |

OTHER PUBLICATIONS

Nassal et al. Topological analysis of the hepatitis B virus core particle by cysteine-cysteine cross-linking. J Mol Biol. Jun. 20, 1992;225(4):1013-25.*

Wynne et al. The crystal structure of the human hepatitis B virus capsid. Mol Cell. Jun. 1999;3(6):771-80.*

Boisgerault, et al., "Virus-like particles: a new family of delivery systems." Expert Rev. Vaccines 1(1):101-109, 2002.

Bottcher, et al., "Determination of the fold of the core protein of hepatitis B virus by electron cryomicroscopy." Nature 386:88-91, 1997.

Brumfield, "Heterologous expression of the modified coat protein of Cowpea chlorotic mottle bromovirus results in the assembly of protein cages with altered architecture and function." J. Gen. Virol. 85:1049-1053, 2004.

Crommelin, et al., "Nanotechnological approaches for the delivery of macromolecules." J Controlled Release 87:81-88, 2003.

Crowther, et al., "Three-dimensional structure of hepatitis B virus core particles determined by electron cryomicroscopy." Cell 77:943-50, 1994.

de Kruif, et al., "Biosynthetically lipid-modified human scFv fragments from phage display libraries as targeting molecules for immunoliposomes" FEBS Lett, 399(3):232-336, 1996.

DeNardo, et al., "Efficacy and Toxicity of 67Cu-2IT-BAT-Lym-1 Radio-immunoconjugate in Mice Implanted with Hamuan Burkitt's Lymphoma (Raji)," Clin. Cancer Res., 3:71-79, 1997.

Fasbender, et al., "Complexes of Adenovirus with Polycationic Polymers and Cationic Lipids Increase the Efficiency of Gene Transfer in Vitro and Vivo" J. Biol. Chem, 272(10):6479-6489, 1997.

Fernandez, et al., "Activated protein C Correlates Inversely with Thrombin Levels in Resting Healthy Individuals" Am. J. Hematol., 56:29-31, 1997.

Ganem and Schneider, "Hepadnaviridae: The Viruses and Their Replication," Chapter 35 of Fundamental Virology, 4th Ed., by David Knipe and Peter Howley, 2001, Published by Lippincott, Williams and Wilkins, Philadelphia, PA, pp. 1285, 1302, and 1303.

Haag, "Supramolecular drug-delivery systems based on polymeric core-shell architectures." Angew Chem. Int. Ed. 43:278-282, 2004.

(56) References Cited

OTHER PUBLICATIONS

Hashida, et al., "Fusion of HIV-1 Tat protein transduction domain to poly-lisine as a new DNA delivery tool" British J. of Cancer, 90(6):1252-1258, 2004.
International Preliminary Report on Patentability for PCT/US2010/31023, dated Oct. 18, 2011, (8 pages).
International Search Report for PCT/US2005/18456, dated Sep. 13, 2006, (4 pages).
International Search Report for PCT/US2008/04585, dated Mar. 17, 2009, (4 pages).
International Search Report for PCT/US2010/31023, mailed Mar. 28, 2011, (7 pages).
Jenny, et al., "A critical review of the methods for cleavage of fusion proteins with thrombin and factor Xa." Prot. Express Purif. 31:1-11, 2003.
Kayser, et al., "Formulation and biopharmaceutical issues in the development of drug delivery systems for antiparasitic drugs." Parasitol Res. 90:S63-S70, 2003.
Lamprecht, et al., "Biodegradable nanoparticles for targeted drug delivery in treatment of inflammatory bowel disease." J. Pharmacol. Exp. Ther. 299:775-81, 2002.
Larsen, et al., "Lyumphoproliferative disorders: prospects for gene therapy" Pathology, 37(6):523-533, 2005.
Leng, et al., Nucleic Acids Research, 33(4): e40, pp. 1-9, 2005.
Liu, et al.,"Nanostructured materials designed for cell binding and transduction." Biomacromolecules 2:362-368, 2001.
Lundstrom, et al., "Breakthrough in cancer therapy:encapsulation of drugs and viruses" Curr. Drug Disc. 19-23, 2002.
Maeda, "The enhanced permeability and retention (EPR) effect in tumor vasculature: the key role of tumor-selective macromolecular drug targeting." Adv. Enzyme Regul. 41:189-207, 2001.
Managit, et al., "Targeted and sustained drug delivery using PEGylated galatosylated liposomes." Int. J. Pharmaceutics 266:77-84, 2003.
Mansfield, et al., "recombinant RFB4 immunotoxins exhibit potent cytoxic activity for CD22-bearing cells and tumors" Blood, 90(5):2020-2026, 1997.
Martin, et al., "Immunospecific targeting of liposomes to cells: a novel and efficient method for covalent attachment of Fab' fragments via disulfide bonds." Biochemistry 20:4229-38, 1981.
Moghimi, et al., "Long-circulating and target-specific nanoparticles: theory to practice." Pharmacol Rev. 53:283-318, 2001.
Monsky, et al., "Augmentation of transvascular transport of macromolecules and nanoparticles in tumors using vascular endothelial growth factor." Cancer Res. 59:4129-35, 1999.
Moreira, et al., "Use of the post-insertion technique to insert peptide ligands into pre-formed Stealth liposomes with retention of binding activity and cytotoxicity" Pharmaceutical Research 19(3):265-269, 2002.
Paddison, et al., "Stable Expression of Gene Suppression by RNAi in mammalian cells" PNAS, 99, (3):1443-1448, 2002.
Panyam, et al., "Biodegradable nanoparticles for drug and gene delivery to cells and tissue." Adv. Drug Del. Rev. 55:329-47, 2003.
Panyam, et al., "Fluorescence and electron microscopy probes for cellular and tissue uptake of poly(D,L-lactide-coglycolide) nanoparticles." Int. J. Pharm. 262:1-11, 2003.
Perales, et al., "An evaluation of receptor-mediated gene transfer using synthetic DNA-ligand complexes" European J. of Biochemistry, 226(2):255-266, 1994.
Roco, et al., "Social Implications of Nanoscience and Technology." National Science Foundation Report, 2001 (280 pages).
Rosenthal, et al., "Viral workhorses." Scientific American, pp. 1-4 ,2002.
Sahoo, et al., "Nanotech approaches to drug delivery and imaging." Drug Disc. Today 8:1112-1120, 2003.
Sahoo, et al.,"Pegylated zinc protoporphyrin: a water-soluble heme oxygenase inhibitor with tumor targeting capacity." Bioconjugate Chem. 13:1031-1038, 2002.
Schmidt, et al., "Binding of external ligands onto an engineered virus capsid," Protein Eng. 14:769-774, 2001.
Schmidt, et al., "Protein and peptide delivery via engineered polyomavirus-like particles." FASEB J 15:1646-1648, 2001.
Scott, et al., "Chemical camouflage of antigenic determinants: stealth erythrocytes" Proc. Natl. Acad. Sci. U. S. A.94(14):7566-7571, (1997).
Sinha, et al., "Biodegradable microspheres for protein delivery." J. Controlled Rel. 90:261-280, 2003.
Stevens, "The cost and value of three-dimensional protein structure" Drug Disc. World 4, 4:35-48, 2003.
Wagner, et al., "Transferrin-polycation-DNA complexes: The effect of polycations on the structure of the complex and DNA delivery to cells" Proceedings of the National Academy of Science of USA, Nat'l Acad. of Sci.,88(10):4255-4259, 1991.
Wynne, et al., "The crystal structure of the human hepatitis B virus capsid." Molecular Cell 3:771-80, 1999.
Yamada, et al., "Nanoparticles for the Delivery of Genes and Drugs to Human Hepatocytes", Nature Biotechnology, 21(8):885-890, 2003.
Zhao, "Intracellular Cargo Delivery Using Tat Peptide and Derivatives," Medical Research Reviews 24(1):1-12, 2004.
Zlotnick, "Are weak protein-protein interactions the general rule in capsid assembly?" Virology, 315:269-274, 2003.
Zlotnick, et al., "Dimorphism of Hepatitis B Virus Capsids is Strongly Influenced by the C-Terminus of the Capsid Protein," Biochemistry, 35:7412-7421, 1996.
Zlotnick, et al., "Localization of the C Terminus of the Assembly Domain of Hepatitis B Virus Capsid Protein: Implications for Morphogenesis and Organization of Encapsidated RNA" Proc. Natl. Acad. Sci. USA, 94:9556-9561, 1997.

\* cited by examiner

SEQUENCE LISTING

<160> NUMBER OF SEQ ID NOS: 149

<210> SEQ ID NO 1
<211> LENGTH: 180
<212> TYPE: PRT
<213> ORGANISM: Hepatitis B virus

<400> SEQUENCE: 1

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu
            180

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro

```
                   130                 135                 140
Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 3
<211> LENGTH: 550
<212> TYPE: DNA
<213> ORGANISM: Hepatitis B virus

<400> SEQUENCE: 3
atggacattg acccttataa agaatttgga gcttctgtgg agttactctc ttttttgcct     60
tctgactttt ttccttctat tcgagatctc ctcgacaccg cctccgctct gtatcgggag   120
gctttagagt ctccggaaca ttgttcacct caccatacag cactcaggca agctattctg   180
tgttggggtg agttaatgaa tctggccacc tgggtgggaa gtaatttgga agatccagca   240
tccagggaat tagtagtcag ctatgtcaat gttaatatgg cctaaaaat cagacaacta   300 ctgtggtttc acatttcctg tcttactttt ggaagagaaa ctgttcttga gtatttggtg   360
tcttttggag tgtggattcg cactcctcct gcttacagac caccaaatgc ccctatctta   420
tcaacacttc cggaaactac tgttgttaga cgacgaggca ggtcccctag aagaagaact   480 cccctcgcctc gcagacgaag gtctcaatcg ccgcgtcgca aagatctca atctcgggaa   540 tctcaatgtt                                                           550

<210> SEQ ID NO 4
<211> LENGTH: 550
<212> TYPE: DNA
<213> ORGANISM: Hepatitis B virus

<400> SEQUENCE: 4
atggacattg atccttataa agaatttgga gcttactgtgg agttactctc gttttttgcct    60 tctgacttct ttccttcagt acgagatctt ctagataccg cctcagctct gtatcgggaa   120
gccttagagt ctcctgagca ttgttcacct caccatactg cactcaggca agcaattctt   180
tgctgggggg aactaatgac tttagccacc tgggtgggtg gtaatttgga agatccaata   240
tccagagacc tagtagtcag ttatgttaac actcatatgg cctaaagtt caggcaacta   300 ttgtggtttc acatttcttg tctcactttt ggaagagaaa cggtcataga gtatttggtg   360
tctttcggag tgtggattcg cactcctcta gcttatagac caccaaatgc ccctatctta   420
tcaacacttc cggagactac tgttgttaga cgacgaggca ggtcccctag aagaagaact   480 cccctcgcctc gcagacgaag gtctcaatcg ccgcgtcgca caaaatctca atctcgggga   540
tctcaatgtt                                                           550

<210> SEQ ID NO 5
<211> LENGTH: 149
<212> TYPE: PRT
<213> ORGANISM: Hepatitis B virus

<400> SEQUENCE: 5

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
```

```
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 6
<211> LENGTH: 149
<212> TYPE: PRT
<213> ORGANISM: Hepatitis B virus

<400> SEQUENCE: 6

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 7
<211> LENGTH: 138
<212> TYPE: PRT
<213> ORGANISM: Hepatitis B virus

<400> SEQUENCE: 7

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
```

```
                35                  40                  45
Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro
                130                 135
```

<210> SEQ ID NO 8
<211> LENGTH: 138
<212> TYPE: PRT
<213> ORGANISM: Hepatitis B virus

<400> SEQUENCE: 8

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro
                130                 135
```

<210> SEQ ID NO 9
<211> LENGTH: 170
<212> TYPE: PRT
<213> ORGANISM: Hepatitis B virus

<400> SEQUENCE: 9

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
```

```
                    85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
            115                 120                 125
Pro Pro Ala Tyr Arg Pro Asn Ala Pro Ile Leu Ser Thr Leu Pro
            130                 135                 140
Glu Thr Thr Val Val Arg Arg Arg Gly Arg Ser Pro Arg Arg Arg Thr
145                 150                 155                 160
Pro Ser Pro Arg Arg Arg Ser Gln Ser
                165                 170

<210> SEQ ID NO 10
<211> LENGTH: 162
<212> TYPE: PRT
<213> ORGANISM: Hepatitis B virus

<400> SEQUENCE: 10

Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Glu Asp Pro Ala
65                  70                  75                  80
Ser Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
            115                 120                 125
Pro Pro Ala Tyr Arg Pro Asn Ala Pro Ile Leu Ser Thr Leu Pro
            130                 135                 140
Glu Thr Thr Val Val Arg Arg Arg Gly Arg Ser Pro Arg Arg Arg Thr
145                 150                 155                 160
Pro Ser

<210> SEQ ID NO 11
<211> LENGTH: 155
<212> TYPE: PRT
<213> ORGANISM: Hepatitis B virus

<400> SEQUENCE: 11

Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Glu Asp Pro Ala
65                  70                  75                  80
```

```
Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser
145                 150                 155

<210> SEQ ID NO 12
<211> LENGTH: 149
<212> TYPE: PRT
<213> ORGANISM: Hepatitis B virus

<400> SEQUENCE: 12

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Cys Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 13
<211> LENGTH: 149
<212> TYPE: PRT
<213> ORGANISM: Hepatitis B virus

<400> SEQUENCE: 13

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Cys Pro Ala
65                  70                  75                  80

Ser Arg Asp Leu Val Val Asn Tyr Val Asn Thr Asn Met Gly Leu Lys
                85                  90                  95
```

```
Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val
145

<210> SEQ ID NO 14
<211> LENGTH: 149
<212> TYPE: PRT
<213> ORGANISM: Hepatitis B virus

<400> SEQUENCE: 14

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
50                  55                  60

Leu Met Thr Leu Ala Thr Trp Val Gly Asn Asn Leu Glu Asp Pro Cys
65                  70                  75                  80

Ser Arg Asp Leu Val Val Asn Tyr Val Asn Thr Asn Met Gly Leu Lys
            85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val
145

<210> SEQ ID NO 15
<211> LENGTH: 149
<212> TYPE: PRT
<213> ORGANISM: Hepatitis B virus
<220> FEATURE:
<221> NAME/KEY: MISC_FEATURE
<222> LOCATION: (14)..(14)
<223> OTHER INFORMATION: X at 14: X=E, H
<220> FEATURE:
<221> NAME/KEY: MISC_FEATURE
<222> LOCATION: (18)..(18)
<223> OTHER INFORMATION: X at 18: X=F, H
<220> FEATURE:
<221> NAME/KEY: MISC_FEATURE
<222> LOCATION: (23)..(23)
<223> OTHER INFORMATION: X at 23: X = F, C, H
<220> FEATURE:
<221> NAME/KEY: MISC_FEATURE
<222> LOCATION: (29)..(29)
<223> OTHER INFORMATION: X at 29: X = D, C
<220> FEATURE:
<221> NAME/KEY: MISC_FEATURE
<222> LOCATION: (33)..(33)
<223> OTHER INFORMATION: X at 33: X = T, C, H
<220> FEATURE:
<221> NAME/KEY: MISC_FEATURE
<222> LOCATION: (36)..(36)
```

```
<223> OTHER INFORMATION: X at 36: X = A, H
<220> FEATURE:
<221> NAME/KEY: MISC_FEATURE
<222> LOCATION: (37)..(37)
<223> OTHER INFORMATION: X at 37 X = L, C, H
<220> FEATURE:
<221> NAME/KEY: MISC_FEATURE
<222> LOCATION: (38)..(38)
<223> OTHER INFORMATION: X at 48: X = C, A
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: MISC_FEATURE
<222> LOCATION: (61)..(61)
<223> OTHER INFORMATION: X at 61: X = C, A
<220> FEATURE:
<221> NAME/KEY: MISC_FEATURE
<222> LOCATION: (77)..(77)
<223> OTHER INFORMATION: X at 77: X = E, C
<220> FEATURE:
<221> NAME/KEY: MISC_FEATURE
<222> LOCATION: (78)..(78)
<223> OTHER INFORMATION: X at 78: X = D, C, S, E
<220> FEATURE:
<221> NAME/KEY: MISC_FEATURE
<222> LOCATION: (79)..(79)
<223> OTHER INFORMATION: X at 79: X = P, C
<220> FEATURE:
<221> NAME/KEY: MISC_FEATURE
<222> LOCATION: (80)..(80)
<223> OTHER INFORMATION: X at 80: X = A, C
<220> FEATURE:
<221> NAME/KEY: MISC_FEATURE
<222> LOCATION: (107)..(107)
<223> OTHER INFORMATION: X at 107: X = C, A
<220> FEATURE:
<221> NAME/KEY: MISC_FEATURE
<222> LOCATION: (118)..(118)
<223> OTHER INFORMATION: X at 118: X = Y, H
<220> FEATURE:
<221> NAME/KEY: MISC_FEATURE
<222> LOCATION: (121)..(121)
<223> OTHER INFORMATION: X at 121: X = S, C
<220> FEATURE:
<221> NAME/KEY: MISC_FEATURE
<222> LOCATION: (122)..(122)
<223> OTHER INFORMATION: X at 122: X = F, H
<220> FEATURE:
<221> NAME/KEY: MISC_FEATURE
<222> LOCATION: (124)..(124)
<223> OTHER INFORMATION: X at 124: X = V, C
<220> FEATURE:
<221> NAME/KEY: MISC_FEATURE
<222> LOCATION: (127)..(127)
<223> OTHER INFORMATION: X at 127: X = R, C
<220> FEATURE:
<221> NAME/KEY: MISC_FEATURE
<222> LOCATION: (132)..(132)
<223> OTHER INFORMATION: X at 132: X = Y, A, V, I, F, C
<220> FEATURE:
<221> NAME/KEY: MISC_FEATURE
<222> LOCATION: (137)..(137)
<223> OTHER INFORMATION: X at 137: X = A, H
<220> FEATURE:
<221> NAME/KEY: MISC_FEATURE
<222> LOCATION: (139)..(139)
<223> OTHER INFORMATION: X at 139: X = I, A
<220> FEATURE:
<221> NAME/KEY: MISC_FEATURE
<222> LOCATION: (141)..(141)
<223> OTHER INFORMATION: X at 141: X = S, C

<400> SEQUENCE: 15

Met Asp Ile Asp Pro Tyr Lys Glu Phe Gly Ala Thr Val Xaa Leu Leu
1               5                   10                  15
```

```
Ser Xaa Leu Pro Ser Asp Xaa Phe Pro Ser Val Arg Xaa Leu Leu Asp
         20                  25                  30

Xaa Ala Ser Xaa Xaa Tyr Arg Glu Ala Leu Glu Ser Pro Glu His Xaa
         35                  40                  45

Ser Pro His His Thr Ala Leu Arg Gln Ala Ile Leu Xaa Trp Gly Glu
 50                      55                  60

Leu Met Thr Leu Ala Thr Trp Val Gly Asn Asn Leu Xaa Xaa Pro Xaa
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Xaa Leu Thr Phe Gly Arg
            100                 105                 110

Glu Thr Val Leu Glu Xaa Leu Val Xaa Xaa Gly Xaa Trp Ile Xaa Thr
            115                 120                 125

Pro Pro Ala Xaa Arg Pro Pro Asn Xaa Pro Xaa Leu Xaa Thr Leu Pro
            130                 135                 140

Glu Thr Thr Val Val
145

<210> SEQ ID NO 16
<211> LENGTH: 162
<212> TYPE: PRT
<213> ORGANISM: Hepatitis B virus

<400> SEQUENCE: 16

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
 50                  55                      60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
            115                 120                 125

Pro Pro Ala Tyr Arg Pro Pro Asn Ala Pro Ile Leu Cys Thr Leu Pro
            130                 135                 140

Glu Thr Thr Val Val Arg Arg Arg Gly Arg Ser Pro Arg Arg Arg Thr
145                 150                 155                 160

Pro Ser

<210> SEQ ID NO 17
<211> LENGTH: 162
<212> TYPE: PRT
<213> ORGANISM: Hepatitis B virus

<400> SEQUENCE: 17

Met Asp Ile Asp Pro Tyr Lys Glu Phe Gly Ala Thr Val His Leu Leu
1               5                   10                  15

Ser Phe Leu Pro Ser Asp Phe Phe Pro Ser Val Arg Asp Leu Leu Asp
```

```
                    20                  25                  30
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Arg Arg Arg Gly Arg Ser Pro Arg Arg Arg Thr
145                 150                 155                 160

Pro Ser

<210> SEQ ID NO 18
<211> LENGTH: 162
<212> TYPE: PRT
<213> ORGANISM: Hepatitis B virus

<400> SEQUENCE: 18

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Cys Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Arg Arg Arg Gly Arg Ser Pro Arg Arg Arg Thr
145                 150                 155                 160

Pro Ser

<210> SEQ ID NO 19
<211> LENGTH: 162
<212> TYPE: PRT
<213> ORGANISM: Hepatitis B virus

<400> SEQUENCE: 19

Met Asp Ile Asp Pro Tyr Lys Glu Phe Gly Ala Thr Val Glu Leu Leu
 1               5                  10                  15
```

```
Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Ala Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser
```

<210> SEQ ID NO 20
<211> LENGTH: 162
<212> TYPE: PRT
<213> ORGANISM: Hepatitis B virus

<400> SEQUENCE: 20

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Val Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser
```

<210> SEQ ID NO 21
<211> LENGTH: 162
<212> TYPE: PRT
<213> ORGANISM: Hepatitis B virus

<400> SEQUENCE: 21

```
Met Asp Ile Asp Pro Tyr Lys Glu Phe Gly Ala Thr Val Glu Leu Leu
1               5                   10                  15
```

```
Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Phe Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 22
<211> LENGTH: 162
<212> TYPE: PRT
<213> ORGANISM: Hepatitis B virus

<400> SEQUENCE: 22

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ala Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 23
<211> LENGTH: 162
<212> TYPE: PRT
<213> ORGANISM: Hepatitis B virus

<400> SEQUENCE: 23

Met Asp Ile Asp Pro Tyr Lys Glu Phe Gly Ala Thr Val Glu Leu Leu
```

```
1               5                   10                  15
Ser His Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser
```

<210> SEQ ID NO 24
<211> LENGTH: 162
<212> TYPE: PRT
<213> ORGANISM: Hepatitis B virus

<400> SEQUENCE: 24

```
Met Asp Ile Asp Pro Tyr Lys Glu Phe Gly Ala Thr Val Glu Leu Leu
1               5                   10                  15

Ser Phe Leu Pro Ser Asp His Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser
```

<210> SEQ ID NO 25
<211> LENGTH: 162
<212> TYPE: PRT
<213> ORGANISM: Hepatitis B virus

<400> SEQUENCE: 25

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

His Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 26
<211> LENGTH: 162
<212> TYPE: PRT
<213> ORGANISM: Hepatitis B virus

<400> SEQUENCE: 26

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 27
<211> LENGTH: 162
<212> TYPE: PRT
<213> ORGANISM: Hepatitis B virus

<400> SEQUENCE: 27

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala His Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser

<210> SEQ ID NO 28
<211> LENGTH: 162
<212> TYPE: PRT
<213> ORGANISM: Hepatitis B virus

<400> SEQUENCE: 28

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu His Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser

<210> SEQ ID NO 29
<211> LENGTH: 162
<212> TYPE: PRT
<213> ORGANISM: Hepatitis B virus

<400> SEQUENCE: 29

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser His Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Thr
145                 150                 155                 160

Pro Ser

<210> SEQ ID NO 30
<211> LENGTH: 162
<212> TYPE: PRT
<213> ORGANISM: Hepatitis B virus

<400> SEQUENCE: 30

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn His Pro Ile Leu Ser Thr Leu Pro
    130                 135                 140

Glu Thr Thr Val Val Arg Arg Gly Arg Ser Pro Arg Arg Thr
145                 150                 155                 160

Pro Ser

<210> SEQ ID NO 31
<211> LENGTH: 162
<212> TYPE: PRT
<213> ORGANISM: Hepatitis B virus

<400> SEQUENCE: 31

```
Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Cys Asp Pro Ala
65                  70                  75                  80
Ser Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Cys Phe Gly Val Trp Ile Arg Thr
        115                 120                 125
Pro Pro Ala Phe Arg Pro Pro Asn Ala Pro Ile Leu Cys Thr Leu Pro
    130                 135                 140
Glu Thr Thr Val Val Arg Arg Arg Gly Arg Ser Pro Arg Arg Arg Thr
145                 150                 155                 160
Pro Ser
```

<210> SEQ ID NO 32
<211> LENGTH: 162
<212> TYPE: PRT
<213> ORGANISM: Hepatitis B virus

<400> SEQUENCE: 32

```
Met Asp Ile Asp Pro Tyr Lys Glu Phe Gly Ala Thr Val Glu Leu Leu
1               5                   10                  15
Ser His Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Cys Asp Pro Ala
65                  70                  75                  80
Ser Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Cys Phe Gly Val Trp Ile Arg Thr
        115                 120                 125
Pro Pro Ala Tyr Arg Pro Pro Asn Ala Pro Ile Leu Cys Thr Leu Pro
    130                 135                 140
Glu Thr Thr Val Val Arg Arg Arg Gly Arg Ser Pro Arg Arg Arg Thr
145                 150                 155                 160
Pro Ser
```

<210> SEQ ID NO 33
<211> LENGTH: 162
<212> TYPE: PRT

<213> ORGANISM: Hepatitis B virus

<400> SEQUENCE: 33

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Ala Arg Pro Pro Asn Ala Pro Ile Leu Cys Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 34
<211> LENGTH: 162
<212> TYPE: PRT
<213> ORGANISM: Hepatitis B virus

<400> SEQUENCE: 34

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Tyr Arg Pro Pro Asn His Pro Ile Leu Cys Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 35
<211> LENGTH: 149

```
<212> TYPE: PRT
<213> ORGANISM: Hepatitis B virus

<400> SEQUENCE: 35

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Ala
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 36
<211> LENGTH: 149
<212> TYPE: PRT
<213> ORGANISM: Hepatitis B virus

<400> SEQUENCE: 36

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Ala Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 37
<211> LENGTH: 149
<212> TYPE: PRT
<213> ORGANISM: Hepatitis B virus
```

```
<400> SEQUENCE: 37

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 38
<211> LENGTH: 150
<212> TYPE: PRT
<213> ORGANISM: Hepatitis B virus

<400> SEQUENCE: 38

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Ala
        35                  40                  45

Ser Pro His His Thr Ala Leu Arg Gln Ala Ile Leu Ala Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Asp
145                 150

<210> SEQ ID NO 39
<211> LENGTH: 149
<212> TYPE: PRT
<213> ORGANISM: Hepatitis B virus

<400> SEQUENCE: 39

Met Asp Ile Asp Pro Tyr Lys Glu Phe Gly Ala Thr Val Glu Leu Leu
```

```
                1               5                   10                  15
        Ser Phe Leu Pro Ser Asp Phe Pro Ser Val Arg Asp Leu Leu Asp
                        20                  25                  30

Thr Ala Ser Ala Leu Tyr Arg Glu Ala Leu Glu Ser Pro Glu His Ala
                        35                  40                  45

Ser Pro His His Thr Ala Leu Arg Gln Ala Ile Leu Cys Trp Gly Glu
                        50                  55                  60

Leu Met Thr Leu Ala Thr Trp Val Gly Asn Asn Leu Cys Asp Pro Ala
        65                      70                  75                  80

Ser Arg Asp Leu Val Val Asn Tyr Val Asn Thr Asn Met Gly Leu Lys
                        85                  90                  95

Ile Arg Gln Leu Leu Trp Phe His Ile Ser Ala Leu Thr Phe Gly Arg
                        100                 105                 110

Glu Thr Val Leu Glu Tyr Leu Val Ser Phe Gly Val Trp Ile Arg Thr
                        115                 120                 125

Pro Pro Ala Tyr Arg Pro Pro Asn Ala Pro Ile Leu Ser Thr Leu Pro
                        130                 135                 140

Glu Thr Thr Val Val
        145

<210> SEQ ID NO 40
<211> LENGTH: 149
<212> TYPE: PRT
<213> ORGANISM: Hepatitis B virus

<400> SEQUENCE: 40

Met Asp Ile Asp Pro Tyr Lys Glu Phe Gly Ala Thr Val Glu Leu Leu
        1               5                   10                  15

Ser Phe Leu Pro Ser Asp Phe Pro Ser Val Arg Asp Leu Leu Asp
                        20                  25                  30

Thr Ala Ser Ala Leu Tyr Arg Glu Ala Leu Glu Ser Pro Glu His Cys
                        35                  40                  45

Ser Pro His His Thr Ala Leu Arg Gln Ala Ile Leu Ala Trp Gly Glu
                        50                  55                  60

Leu Met Thr Leu Ala Thr Trp Val Gly Asn Asn Leu Cys Asp Pro Ala
        65                      70                  75                  80

Ser Arg Asp Leu Val Val Asn Tyr Val Asn Thr Asn Met Gly Leu Lys
                        85                  90                  95

Ile Arg Gln Leu Leu Trp Phe His Ile Ser Ala Leu Thr Phe Gly Arg
                        100                 105                 110

Glu Thr Val Leu Glu Tyr Leu Val Ser Phe Gly Val Trp Ile Arg Thr
                        115                 120                 125

Pro Pro Ala Tyr Arg Pro Pro Asn Ala Pro Ile Leu Ser Thr Leu Pro
                        130                 135                 140

Glu Thr Thr Val Val
        145

<210> SEQ ID NO 41
<211> LENGTH: 149
<212> TYPE: PRT
<213> ORGANISM: Hepatitis B virus

<400> SEQUENCE: 41

Met Asp Ile Asp Pro Tyr Lys Glu Phe Gly Ala Thr Val Glu Leu Leu
        1               5                   10                  15

Ser Phe Leu Pro Ser Asp Phe Pro Ser Val Arg Asp Leu Leu Asp
```

```
                    20                  25                  30
Thr Ala Ser Ala Leu Tyr Arg Glu Ala Leu Glu Ser Pro Glu His Ala
            35                  40                  45

Ser Pro His His Thr Ala Leu Arg Gln Ala Ile Leu Ala Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val
145

<210> SEQ ID NO 42
<211> LENGTH: 183
<212> TYPE: PRT
<213> ORGANISM: Hepatitis B virus

<400> SEQUENCE: 42

Met Asp Ile Asp Pro Tyr Lys Glu Phe Gly Ala Thr Val Glu Leu Leu
1               5                   10                  15

Ser Phe Leu Pro Ser Asp Cys Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Cys Arg Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Ser
                165                 170                 175

Gln Ser Arg Glu Ser Gln Cys
            180

<210> SEQ ID NO 43
<211> LENGTH: 183
<212> TYPE: PRT
<213> ORGANISM: Hepatitis B virus

<400> SEQUENCE: 43

Met Asp Ile Asp Pro Tyr Lys Glu Phe Gly Ala Ser Val Glu Leu Leu
```

```
  1               5                   10                  15
Ser Phe Leu Pro Ser Asp Cys Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
            50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Cys Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 44
<211> LENGTH: 183
<212> TYPE: PRT
<213> ORGANISM: Hepatitis B virus

<400> SEQUENCE: 44

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Cys Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
            50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 45
<211> LENGTH: 183
<212> TYPE: PRT
<213> ORGANISM: Hepatitis B virus

<400> SEQUENCE: 45

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Cys Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 46
<211> LENGTH: 183
<212> TYPE: PRT
<213> ORGANISM: Hepatitis B virus

<400> SEQUENCE: 46

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Cys Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Cys Trp Ile Arg Thr
        115                 120                 125

Pro Pro Ala Tyr Arg Pro Pro Asn Ala Pro Ile Leu Ser Thr Leu Pro
    130                 135                 140
```

```
Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 47
<211> LENGTH: 183
<212> TYPE: PRT
<213> ORGANISM: Hepatitis B virus

<400> SEQUENCE: 47

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Cys Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Cys Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 48
<211> LENGTH: 183
<212> TYPE: PRT
<213> ORGANISM: Hepatitis B virus

<400> SEQUENCE: 48

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Cys Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95
```

```
Ile Arg Gln Leu Leu Trp Phe His Ile Ser Cys Leu Thr Phe Gly Arg
            100                 105                 110

Glu Thr Val Leu Glu Tyr Leu Cys Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
            165                 170                 175

Gln Ser Arg Glu Ser Gln Cys
            180

<210> SEQ ID NO 49
<211> LENGTH: 183
<212> TYPE: PRT
<213> ORGANISM: Hepatitis B virus

<400> SEQUENCE: 49

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Cys Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Cys Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
            165                 170                 175

Gln Ser Arg Glu Ser Gln Cys
            180

<210> SEQ ID NO 50
<211> LENGTH: 149
<212> TYPE: PRT
<213> ORGANISM: Hepatitis B virus

<400> SEQUENCE: 50

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45
```

```
Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Ser Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 51
<211> LENGTH: 149
<212> TYPE: PRT
<213> ORGANISM: Hepatitis B virus

<400> SEQUENCE: 51

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Glu Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 52
<211> LENGTH: 12
<212> TYPE: PRT
<213> ORGANISM: Hepatitis B virus

<400> SEQUENCE: 52

Gly Pro Gly Ala Pro Gly Leu Val Pro Arg Gly Ser
1               5                   10

<210> SEQ ID NO 53
<211> LENGTH: 12
<212> TYPE: PRT
<213> ORGANISM: Hepatitis B virus

<400> SEQUENCE: 53

Gly Pro Ala Ser Gly Pro Gly Ile Glu Gly Arg Ala
```

<210> SEQ ID NO 54
<211> LENGTH: 162
<212> TYPE: PRT
<213> ORGANISM: Hepatitis B virus

<400> SEQUENCE: 54

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 55
<211> LENGTH: 162
<212> TYPE: PRT
<213> ORGANISM: Hepatitis B virus

<400> SEQUENCE: 55

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser

<210> SEQ ID NO 56
<211> LENGTH: 34
<212> TYPE: PRT
<213> ORGANISM: Hepatitis B virus

<400> SEQUENCE: 56

Arg Arg Arg Gly Arg Ser Pro Arg Arg Arg Thr Pro Ser Pro Arg Arg
1               5                   10                  15

Arg Arg Ser Gln Ser Pro Arg Arg Arg Ser Gln Ser Arg Glu Ser
            20                  25                  30

Gln Cys

<210> SEQ ID NO 57
<211> LENGTH: 4
<212> TYPE: PRT
<213> ORGANISM: Hepatitis B virus

<400> SEQUENCE: 57

Ser Gln Ser Pro
1

<210> SEQ ID NO 58
<211> LENGTH: 13
<212> TYPE: PRT
<213> ORGANISM: Hepatitis B virus

<400> SEQUENCE: 58

Lys Leu Ala Ala Ala Lys Lys Lys Lys Leu Glu His
1               5                   10

<210> SEQ ID NO 59
<211> LENGTH: 10
<212> TYPE: PRT
<213> ORGANISM: Hepatitis B virus

<400> SEQUENCE: 59

Asp Lys Leu Ala Ala Ala Lys Leu Glu His
1               5                   10

<210> SEQ ID NO 60
<211> LENGTH: 168
<212> TYPE: PRT
<213> ORGANISM: Hepatitis B virus

<400> SEQUENCE: 60

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg

```
            100                 105                 110
Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Asp Lys Leu Ala Ala Ala Lys Lys Lys Lys Lys
145                 150                 155                 160

Leu Glu His His His His His
                165

<210> SEQ ID NO 61
<211> LENGTH: 170
<212> TYPE: PRT
<213> ORGANISM: Hepatitis B virus

<400> SEQUENCE: 61

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Asp Lys Leu Ala Ala Ala Lys Lys Lys Lys Lys
145                 150                 155                 160

Lys Lys Leu Glu His His His His His
                165                 170

<210> SEQ ID NO 62
<211> LENGTH: 172
<212> TYPE: PRT
<213> ORGANISM: Hepatitis B virus

<400> SEQUENCE: 62

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
```

```
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Asn Ala Pro Ile Leu Ser Thr Leu Pro
        130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170

<210> SEQ ID NO 63
<211> LENGTH: 173
<212> TYPE: PRT
<213> ORGANISM: Hepatitis B virus

<400> SEQUENCE: 63

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Asn Ala Pro Ile Leu Ser Thr Leu Pro
        130                 135                 140

Glu Thr Thr Val Val Asp Lys Leu Ala Ala Ala Lys Lys Lys Lys Lys
145                 150                 155                 160

Lys Lys Lys Lys Lys Leu Glu His His His His His
                165                 170

<210> SEQ ID NO 64
<211> LENGTH: 174
<212> TYPE: PRT
<213> ORGANISM: Hepatitis B virus

<400> SEQUENCE: 64

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
```

```
                65                  70                  75                  80
Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Lys Lys Lys Lys
145                 150                 155                 160

Lys Lys Lys Lys Lys Lys Lys Leu Glu His His His His His
                165                 170
```

<210> SEQ ID NO 65
<211> LENGTH: 176
<212> TYPE: PRT
<213> ORGANISM: Hepatitis B virus

<400> SEQUENCE: 65

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
                50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Lys Lys Lys Lys
145                 150                 155                 160

Lys Lys Lys Lys Lys Lys Lys Leu Glu His His His His His His
                165                 170                 175
```

<210> SEQ ID NO 66
<211> LENGTH: 183
<212> TYPE: PRT
<213> ORGANISM: Hepatitis B virus

<400> SEQUENCE: 66

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
```

```
Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Lys Lys Lys Lys Lys Lys Lys Lys Lys Lys Lys Leu
                165                 170                 175

Glu His His His His His His
            180
```

<210> SEQ ID NO 67
<211> LENGTH: 176
<212> TYPE: PRT
<213> ORGANISM: Hepatitis B virus

<400> SEQUENCE: 67

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Ser
145                 150                 155                 160

Gln Ser Pro Lys Lys Lys Lys Leu Glu His His His His His His
                165                 170                 175
```

<210> SEQ ID NO 68
<211> LENGTH: 180
<212> TYPE: PRT
<213> ORGANISM: Hepatitis B virus

<400> SEQUENCE: 68

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
```

```
                        20                  25                  30
Thr Ala Ser Ala Leu Tyr Arg Glu Ala Leu Glu Ser Pro Glu His Cys
                    35                  40                  45

Ser Pro His His Thr Ala Leu Arg Gln Ala Ile Leu Cys Trp Gly Glu
                50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Ala Lys Ala Lys
145                 150                 155                 160

Ala Lys Ala Lys Ala Lys Ala Lys Ala Lys Leu Glu His His
                165                 170                 175

His His His His
            180

<210> SEQ ID NO 69
<211> LENGTH: 180
<212> TYPE: PRT
<213> ORGANISM: Hepatitis B virus

<400> SEQUENCE: 69

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
                50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Gly Lys Gly Lys
145                 150                 155                 160

Gly Lys Gly Lys Gly Lys Gly Lys Gly Lys Leu Glu His His
                165                 170                 175

His His His His
            180

<210> SEQ ID NO 70
<211> LENGTH: 172
```

```
<212> TYPE: PRT
<213> ORGANISM: Hepatitis B virus

<400> SEQUENCE: 70

Met Asp Ile Asp Pro Tyr Lys Glu Phe Gly Ala Thr Val Glu Leu Leu
1               5                   10                  15

Ser His Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170

<210> SEQ ID NO 71
<211> LENGTH: 172
<212> TYPE: PRT
<213> ORGANISM: Hepatitis B virus

<400> SEQUENCE: 71

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Ala Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170
```

<210> SEQ ID NO 72
<211> LENGTH: 172
<212> TYPE: PRT
<213> ORGANISM: Hepatitis B virus

<400> SEQUENCE: 72

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Val Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170
```

<210> SEQ ID NO 73
<211> LENGTH: 172
<212> TYPE: PRT
<213> ORGANISM: Hepatitis B virus

<400> SEQUENCE: 73

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ala Leu Ser Thr Leu Pro
    130                 135                 140

Glu Thr Thr Val Val Asp Lys Leu Ala Ala Ala Lys Lys Lys Lys Lys
145                 150                 155                 160
```

Lys Lys Lys Lys Leu Glu His His His His His
            165                 170

<210> SEQ ID NO 74
<211> LENGTH: 172
<212> TYPE: PRT
<213> ORGANISM: Hepatitis B virus

<400> SEQUENCE: 74

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Ile Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
            165                 170

<210> SEQ ID NO 75
<211> LENGTH: 172
<212> TYPE: PRT
<213> ORGANISM: Hepatitis B virus

<400> SEQUENCE: 75

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Phe Arg Pro Pro Asn Ala Pro Ile Leu Ser Thr Leu Pro
    130                 135                 140

Glu Thr Thr Val Val Asp Lys Leu Ala Ala Ala Lys Lys Lys Lys
145                 150                 155                 160

Lys Lys Lys Lys Leu Glu His His His His His
                165                 170

<210> SEQ ID NO 76
<211> LENGTH: 172
<212> TYPE: PRT
<213> ORGANISM: Hepatitis B virus

<400> SEQUENCE: 76

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Ala
            35                  40                  45

Ser Pro His His Thr Ala Leu Arg Gln Ala Ile Leu Cys Trp Gly Glu
50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170

<210> SEQ ID NO 77
<211> LENGTH: 172
<212> TYPE: PRT
<213> ORGANISM: Hepatitis B virus

<400> SEQUENCE: 77

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Ala
            35                  40                  45

Ser Pro His His Thr Ala Leu Arg Gln Ala Ile Leu Ala Trp Gly Glu
50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
            130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170

<210> SEQ ID NO 78
<211> LENGTH: 172
<212> TYPE: PRT
<213> ORGANISM: Hepatitis B virus

<400> SEQUENCE: 78

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Tyr Arg Pro Pro Asn Ala Pro Ile Leu Ser Thr Leu Pro
            130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170

<210> SEQ ID NO 79
<211> LENGTH: 172
<212> TYPE: PRT
<213> ORGANISM: Hepatitis B virus

<400> SEQUENCE: 79

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

```
Glu Thr Val Leu Glu Tyr Leu Val Cys Phe Gly Val Trp Ile Arg Thr
            115                 120                 125

Pro Pro Ala Tyr Arg Pro Pro Asn Ala Pro Ile Leu Cys Thr Leu Pro
        130                 135                 140

Glu Thr Thr Val Val Asp Lys Leu Ala Ala Lys Lys Lys Lys
145                 150                 155                 160

Lys Lys Lys Lys Leu Glu His His His His His
                165                 170

<210> SEQ ID NO 80
<211> LENGTH: 172
<212> TYPE: PRT
<213> ORGANISM: Hepatitis B virus

<400> SEQUENCE: 80

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Phe Arg Pro Pro Asn Ala Pro Ile Leu Cys Thr Leu Pro
    130                 135                 140

Glu Thr Thr Val Val Asp Lys Leu Ala Ala Lys Lys Lys Lys
145                 150                 155                 160

Lys Lys Lys Lys Leu Glu His His His His His
                165                 170

<210> SEQ ID NO 81
<211> LENGTH: 172
<212> TYPE: PRT
<213> ORGANISM: Hepatitis B virus

<400> SEQUENCE: 81

Met Asp Ile Asp Pro Tyr Lys Glu Phe Gly Ala Thr Val Glu Leu Leu
1               5                   10                  15

Ser His Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95
```

```
Ile Arg Gln Leu Leu Trp Phe His Ile Ser Cys Leu Thr Phe Gly Arg
                100                 105                 110

Glu Thr Val Leu Glu Tyr Leu Val Cys Phe Gly Val Trp Ile Arg Thr
            115                 120                 125

Pro Pro Ala Tyr Arg Pro Pro Asn Ala Pro Ile Leu Cys Thr Leu Pro
        130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170

<210> SEQ ID NO 82
<211> LENGTH: 172
<212> TYPE: PRT
<213> ORGANISM: Hepatitis B virus

<400> SEQUENCE: 82

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Glu Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Asp Lys Leu Ala Ala Ala Lys Lys Lys Lys Lys
145                 150                 155                 160

Lys Lys Lys Lys Leu Glu His His His His His
                165                 170

<210> SEQ ID NO 83
<211> LENGTH: 172
<212> TYPE: PRT
<213> ORGANISM: Hepatitis B virus

<400> SEQUENCE: 83

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Lys Asp Pro Ala
65                  70                  75                  80
```

```
Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Lys Lys Lys Lys Lys
145                 150                 155                 160

Lys Lys Lys Lys Leu Glu His His His His His His
                165                 170

<210> SEQ ID NO 84
<211> LENGTH: 10
<212> TYPE: PRT
<213> ORGANISM: Hepatitis B virus

<400> SEQUENCE: 84

Asp Lys Leu Ala Ala Ala Arg Leu Glu His
1               5                   10

<210> SEQ ID NO 85
<211> LENGTH: 3
<212> TYPE: PRT
<213> ORGANISM: Hepatitis B virus

<400> SEQUENCE: 85

Ser Ala Gly
1

<210> SEQ ID NO 86
<211> LENGTH: 3
<212> TYPE: PRT
<213> ORGANISM: Hepatitis B virus

<400> SEQUENCE: 86

Thr Ala Gly
1

<210> SEQ ID NO 87
<211> LENGTH: 3
<212> TYPE: PRT
<213> ORGANISM: Hepatitis B virus

<400> SEQUENCE: 87

Gly Ala Gly
1

<210> SEQ ID NO 88
<211> LENGTH: 171
<212> TYPE: PRT
<213> ORGANISM: Hepatitis B virus

<400> SEQUENCE: 88

Met Asp Ile Asp Pro Tyr Lys Glu Phe Gly Ala Thr Val Glu Leu Leu
1               5                   10                  15

Ser His Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45
```

```
Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Leu Glu His His His His His Cys
                165                 170

<210> SEQ ID NO 89
<211> LENGTH: 570
<212> TYPE: DNA
<213> ORGANISM: Hepatitis B virus

<400> SEQUENCE: 89
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg tgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg tacccegccg gcgtatcgtc cgccgaatgc gccgattctg     420 agcacccctgc cggaaaccac cgttgtgcgt cgccgtggtc gcagcccgcg ccgtcgtacc     480
ccgagcccgc gtcgtcgtcg tagccagagc ccgtcgtcgt ccgcagccag agccgcgaa     540 agccagctcg agcaccacca ccaccaccac                                       570

<210> SEQ ID NO 90
<211> LENGTH: 190
<212> TYPE: PRT
<213> ORGANISM: Hepatitis B virus

<400> SEQUENCE: 90

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
```

|     | 100 |     |     | 105 |     |     |     | 110 |     |     |     |
| --- | --- | --- | --- | --- | --- | --- | --- | --- | --- | --- | --- |

Glu Thr Val Leu Glu Tyr Leu Val Ser Phe Gly Val Trp Ile Arg Thr
    115                120                  125

Pro Pro Ala Tyr Arg Pro Pro Asn Ala Pro Ile Leu Ser Thr Leu Pro
   130                 135                140

Glu Thr Thr Val Val Arg Arg Arg Gly Arg Ser Pro Arg Arg Arg Thr
145                150                155                160

Pro Ser Pro Arg Arg Arg Ser Gln Ser Pro Arg Arg Arg Arg Ser
           165                170              175

Gln Ser Arg Glu Ser Gln Leu Glu His His His His His
        180                185              190

<210> SEQ ID NO 91
<211> LENGTH: 492
<212> TYPE: DNA
<213> ORGANISM: Hepatitis B virus

<400> SEQUENCE: 91

| | |
|---|---|
| atggatatcg atccgtataa agaatttggc gccaccgtgg aactgctgag ctttctgccg | 60 |
| agcgatttct ttccgagcgt gcgtgatctg ctggataccg cgagcgcgct gtatcgcgaa | 120 |
| gcgctggaaa gcccggaaca ttgtagcccg caccataccg ccctgcgtca ggcgattctg | 180 |
| tgctggggtg aactgatgac cctggcgacc tgggttggca caacctgtg cgatccggcg | 240 |
| agccgcgatc tggttgtgaa ctatgtgaat accaacatgg gcctgaaaat tcgtctgctg | 300 |
| ctgtggtttc atatcagctg cctgaccttt ggcgcgaaa ccgtgctgga atatctggtg | 360 |
| agctttggcg tttggatccg taccccgccg gcgtatcgtc cgccgaatgc gccgattctg | 420 |
| agcaccctgc cggaaaccac cgttgtcgac aagcttgcgg ccgcactcga gcaccaccac | 480 |
| caccaccact ga | 492 |

<210> SEQ ID NO 92
<211> LENGTH: 28
<212> TYPE: DNA
<213> ORGANISM: Hepatitis B virus

<400> SEQUENCE: 92

| | |
|---|---|
| cgactcacta tagggaatt gtgagcgg | 28 |

<210> SEQ ID NO 93
<211> LENGTH: 45
<212> TYPE: DNA
<213> ORGANISM: Hepatitis B virus

<400> SEQUENCE: 93

| | |
|---|---|
| ggcctcgagc ttcttttct ctttgcggc cgcaagcttg tcgac | 45 |

<210> SEQ ID NO 94
<211> LENGTH: 51
<212> TYPE: DNA
<213> ORGANISM: Hepatitis B virus

<400> SEQUENCE: 94

| | |
|---|---|
| ggcctcgagc ttcttcttt tcttcttct tgcggccgca agcttgtcga c | 51 |

<210> SEQ ID NO 95
<211> LENGTH: 57
<212> TYPE: DNA
<213> ORGANISM: Hepatitis B virus

```
<400> SEQUENCE: 95
ggcctcgagc ttcttctttt tcttcttctt tttctttgcg gccgcaagct tgtcgac      57

<210> SEQ ID NO 96
<211> LENGTH: 60
<212> TYPE: DNA
<213> ORGANISM: Hepatitis B virus

<400> SEQUENCE: 96
ggcctcgagt ttcttcttct tcttcttctt cttttcttt gcggccgcaa gcttgtcgac   60

<210> SEQ ID NO 97
<211> LENGTH: 63
<212> TYPE: DNA
<213> ORGANISM: Hepatitis B virus

<400> SEQUENCE: 97
ggcctcgagc ttcttctttt tcttcttctt tttcttcttc tttgcggccg caagcttgtc   60
gac                                                                 63

<210> SEQ ID NO 98
<211> LENGTH: 69
<212> TYPE: DNA
<213> ORGANISM: Hepatitis B virus

<400> SEQUENCE: 98
ggcctcgagc ttcttctttt tcttcttctt tttcttcttc ttttctttg cggccgcaag   60 cttgtcgac                                                           69

<210> SEQ ID NO 99
<211> LENGTH: 90
<212> TYPE: DNA
<213> ORGANISM: Hepatitis B virus

<400> SEQUENCE: 99
ggcctcgagc tttttcttct tcttcttctt cttcttcttt ttcttcttct tcttcttctt   60
cttttctttt gcggccgcaa gcttgtcgac                                    90

<210> SEQ ID NO 100
<211> LENGTH: 81
<212> TYPE: DNA
<213> ORGANISM: Hepatitis B virus

<400> SEQUENCE: 100
ggcctcgagc ttcgccttag ccttcgcctt agcctttgcc ttcgccttag cctttgcctt   60
tgcggccgca agcttgtcga c                                             81

<210> SEQ ID NO 101
<211> LENGTH: 81
<212> TYPE: DNA
<213> ORGANISM: Hepatitis B virus

<400> SEQUENCE: 101
ggcctcgagc ttaccctgc ccttgcccctt acccttgccc ttacccttgc ccttaccctt   60
tgcggccgca agcttgtcga c                                             81

<210> SEQ ID NO 102
<211> LENGTH: 69
<212> TYPE: DNA
<213> ORGANISM: Hepatitis B virus
```

<400> SEQUENCE: 102
ggcctcgagt tcttcttct tcttcgggct ctggctcttc ttttctttg cggccgcaag    60 cttgtcgac                                                          69

<210> SEQ ID NO 103
<211> LENGTH: 30
<212> TYPE: DNA
<213> ORGANISM: Hepatitis B virus

<400> SEQUENCE: 103
attctcgagg ctgcgaccac ggcgacgcac                                   30

<210> SEQ ID NO 104
<211> LENGTH: 30
<212> TYPE: DNA
<213> ORGANISM: Hepatitis B virus

<400> SEQUENCE: 104
attctcgagg ctcggggtac gacggcgcgg                                   30

<210> SEQ ID NO 105
<211> LENGTH: 42
<212> TYPE: DNA
<213> ORGANISM: Hepatitis B virus

<400> SEQUENCE: 105
attctcgagg ctctggctac gacgacgacg cgggctcggg gt                     42

<210> SEQ ID NO 106
<211> LENGTH: 75
<212> TYPE: DNA
<213> ORGANISM: Hepatitis B virus

<400> SEQUENCE: 106
ggcctcgagc ttcttctttt tcttcttctt tttcttgccg gcgctgcccg cgctgacaac    60
ggtggtttcc ggcag                                                   75

<210> SEQ ID NO 107
<211> LENGTH: 75
<212> TYPE: DNA
<213> ORGANISM: Hepatitis B virus

<400> SEQUENCE: 107
ggcctcgagc ttcttctttt tcttcttctt tttcttgccg gcggtgcccg cggtgacaac    60
ggtggtttcc ggcag                                                   75

<210> SEQ ID NO 108
<211> LENGTH: 75
<212> TYPE: DNA
<213> ORGANISM: Hepatitis B virus

<400> SEQUENCE: 108
ggcctcgagc ttcttctttt tcttcttctt tttcttgccg gcgccgcccg cgccgacaac    60
ggtggtttcc ggcag                                                   75

<210> SEQ ID NO 109
<211> LENGTH: 516
<212> TYPE: DNA
<213> ORGANISM: Hepatitis B virus

```
<400> SEQUENCE: 109
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg cgatccggcg      240 agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                               516

<210> SEQ ID NO 110
<211> LENGTH: 28
<212> TYPE: DNA
<213> ORGANISM: Hepatitis B virus

<400> SEQUENCE: 110
aactgctgag ccatctgccg agcgattt                                         28

<210> SEQ ID NO 111
<211> LENGTH: 28
<212> TYPE: DNA
<213> ORGANISM: Hepatitis B virus

<400> SEQUENCE: 111
aaatcgctcg gcagatggct cagcagtt                                         28

<210> SEQ ID NO 112
<211> LENGTH: 28
<212> TYPE: DNA
<213> ORGANISM: Hepatitis B virus

<400> SEQUENCE: 112
taccccgccg gcggctcgtc cgccgaat                                         28

<210> SEQ ID NO 113
<211> LENGTH: 28
<212> TYPE: DNA
<213> ORGANISM: Hepatitis B virus

<400> SEQUENCE: 113
attcggcgga cgagccgccg gcggggta                                         28

<210> SEQ ID NO 114
<211> LENGTH: 28
<212> TYPE: DNA
<213> ORGANISM: Hepatitis B virus

<400> SEQUENCE: 114
taccccgccg gcggttcgtc cgccgaat                                         28

<210> SEQ ID NO 115
<211> LENGTH: 28
<212> TYPE: DNA
<213> ORGANISM: Hepatitis B virus

<400> SEQUENCE: 115
attcggcgga cgaaccgccg gcggggta                                         28
```

```
<210> SEQ ID NO 116
<211> LENGTH: 28
<212> TYPE: DNA
<213> ORGANISM: Hepatitis B virus

<400> SEQUENCE: 116
taccccgccg gcgattcgtc cgccgaat                                28

<210> SEQ ID NO 117
<211> LENGTH: 28
<212> TYPE: DNA
<213> ORGANISM: Hepatitis B virus

<400> SEQUENCE: 117
attcggcgga cgaatcgccg gcggggta                                28

<210> SEQ ID NO 118
<211> LENGTH: 28
<212> TYPE: DNA
<213> ORGANISM: Hepatitis B virus

<400> SEQUENCE: 118
taccccgccg gcgtttcgtc cgccgaat                                28

<210> SEQ ID NO 119
<211> LENGTH: 28
<212> TYPE: DNA
<213> ORGANISM: Hepatitis B virus

<400> SEQUENCE: 119
attcggcgga cgaaacgccg gcggggta                                28

<210> SEQ ID NO 120
<211> LENGTH: 30
<212> TYPE: DNA
<213> ORGANISM: Hepatitis B virus

<400> SEQUENCE: 120
tccgccgaat gcgccggctc tgagcaccct                              30

<210> SEQ ID NO 121
<211> LENGTH: 30
<212> TYPE: DNA
<213> ORGANISM: Hepatitis B virus

<400> SEQUENCE: 121
agggtgctca gagccggcgc attcggcgga                              30

<210> SEQ ID NO 122
<211> LENGTH: 27
<212> TYPE: DNA
<213> ORGANISM: Hepatitis B virus

<400> SEQUENCE: 122
tggaatatct ggtgtgcttt ggcgttt                                 27

<210> SEQ ID NO 123
<211> LENGTH: 27
<212> TYPE: DNA
<213> ORGANISM: Hepatitis B virus

<400> SEQUENCE: 123
```
aaacgccaaa gcacaccaga tattcca                                         27

<210> SEQ ID NO 124
<211> LENGTH: 30
<212> TYPE: DNA
<213> ORGANISM: Hepatitis B virus

<400> SEQUENCE: 124
atgcgccgat tctgtgcacc ctgccggaaa                                      30

<210> SEQ ID NO 125
<211> LENGTH: 30
<212> TYPE: DNA
<213> ORGANISM: Hepatitis B virus

<400> SEQUENCE: 125
tttccggcag ggtgcacaga atcggcgcat                                      30

<210> SEQ ID NO 126
<211> LENGTH: 27
<212> TYPE: DNA
<213> ORGANISM: Hepatitis B virus

<400> SEQUENCE: 126
agcccggaac atgcgagccc gcaccat                                         27

<210> SEQ ID NO 127
<211> LENGTH: 27
<212> TYPE: DNA
<213> ORGANISM: Hepatitis B virus

<400> SEQUENCE: 127
atggtgcggg ctcgcatgtt ccgggct                                         27

<210> SEQ ID NO 128
<211> LENGTH: 25
<212> TYPE: DNA
<213> ORGANISM: Hepatitis B virus

<400> SEQUENCE: 128
aggcgattct ggcgtggggt gaact                                           25

<210> SEQ ID NO 129
<211> LENGTH: 25
<212> TYPE: DNA
<213> ORGANISM: Hepatitis B virus

<400> SEQUENCE: 129
agttcacccc acgccagaat cgcct                                           25

<210> SEQ ID NO 130
<211> LENGTH: 32
<212> TYPE: DNA
<213> ORGANISM: Hepatitis B virus

<400> SEQUENCE: 130
tttcatatca gcgcgctgac ctttggccgc ga                                   32

<210> SEQ ID NO 131
<211> LENGTH: 32
<212> TYPE: DNA
<213> ORGANISM: Hepatitis B virus

<400> SEQUENCE: 131

-continued tcgcggccaa aggtcagcgc gctgatatga aa                                    32

<210> SEQ ID NO 132
<211> LENGTH: 33
<212> TYPE: DNA
<213> ORGANISM: Hepatitis B virus

<400> SEQUENCE: 132
tggcaacaac ctggaaagcc cggcgagccg cga                                   33

<210> SEQ ID NO 133
<211> LENGTH: 33
<212> TYPE: DNA
<213> ORGANISM: Hepatitis B virus

<400> SEQUENCE: 133
tcgcggctcg ccgggctttc caggttgttg cca                                   33

<210> SEQ ID NO 134
<211> LENGTH: 35
<212> TYPE: DNA
<213> ORGANISM: Hepatitis B virus

<400> SEQUENCE: 134
ttggcaacaa cctggaagaa ccggcgagcc gcgat                                 35

<210> SEQ ID NO 135
<211> LENGTH: 35
<212> TYPE: DNA
<213> ORGANISM: Hepatitis B virus

<400> SEQUENCE: 135
atcgcggctc gccggttctt ccaggttgtt gccaa                                 35

<210> SEQ ID NO 136
<211> LENGTH: 27
<212> TYPE: DNA
<213> ORGANISM: Hepatitis B virus

<400> SEQUENCE: 136
aagaaaaaga agaagtgaga tccggct                                          27

<210> SEQ ID NO 137
<211> LENGTH: 30
<212> TYPE: DNA
<213> ORGANISM: Hepatitis B virus

<400> SEQUENCE: 137
agcagccgga tctcacttct tcttttctt                                        30

<210> SEQ ID NO 138
<211> LENGTH: 170
<212> TYPE: PRT
<213> ORGANISM: Hepatitis B virus

<400> SEQUENCE: 138

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 139
<211> LENGTH: 170
<212> TYPE: PRT
<213> ORGANISM: Hepatitis B virus

<400> SEQUENCE: 139

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser His Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 140
<211> LENGTH: 170
<212> TYPE: PRT
<213> ORGANISM: Hepatitis B virus

<400> SEQUENCE: 140

Met Asp Ile Asp Pro Tyr Lys Glu Phe Gly Ala Thr Val His Leu Leu
1               5                   10                  15

Ser Phe Leu Pro Ser Asp Phe Phe Pro Ser Val Arg Asp Leu Leu Asp
            20                  25                  30

```
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                   100                 105                 110

Glu Thr Val Leu Glu Tyr Leu Val Ser Phe Gly Val Trp Ile Arg Thr
                   115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Leu Glu His His His His His His
                   165                 170

<210> SEQ ID NO 141
<211> LENGTH: 170
<212> TYPE: PRT
<213> ORGANISM: Hepatitis B virus

<400> SEQUENCE: 141

Met Asp Ile Asp Pro Tyr Lys Glu Phe Gly Ala Thr Val Glu Leu Leu
1               5                  10                  15

Ser His Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                   100                 105                 110

Glu Thr Val Leu Glu Tyr Leu Val Ser Phe Gly Val Trp Ile Arg Thr
                   115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Leu Glu His His His His His His
                   165                 170

<210> SEQ ID NO 142
<211> LENGTH: 170
<212> TYPE: PRT
<213> ORGANISM: Hepatitis B virus

<400> SEQUENCE: 142

Met Asp Ile Asp Pro Tyr Lys Glu Phe Gly Ala Thr Val Glu Leu Leu
1               5                  10                  15
```

```
Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Phe Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 143
<211> LENGTH: 170
<212> TYPE: PRT
<213> ORGANISM: Hepatitis B virus

<400> SEQUENCE: 143

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn His Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 144
<211> LENGTH: 170
<212> TYPE: PRT
<213> ORGANISM: Hepatitis B virus

<400> SEQUENCE: 144
```

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu His Leu Val Ser Phe Gly Val Trp Ile Arg Thr
        115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 145
<211> LENGTH: 170
<212> TYPE: PRT
<213> ORGANISM: Hepatitis B virus

<400> SEQUENCE: 145

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala His Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 146
<211> LENGTH: 171
<212> TYPE: PRT
```

<213> ORGANISM: Hepatitis B virus

<400> SEQUENCE: 146

```
Met Asp Ile Asp Pro Tyr Lys Glu Phe Gly Ala Thr Val Glu Leu Leu
1               5                   10                  15
Ser His Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Cys Asp Pro Ala
65                  70                  75                  80
Ser Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val Arg Arg Arg Gly Arg Ser Pro Arg Arg Arg Thr
145                 150                 155                 160
Pro Ser Leu Glu His His His His His Cys
                165                 170
```

<210> SEQ ID NO 147
<211> LENGTH: 171
<212> TYPE: PRT
<213> ORGANISM: Hepatitis B virus

<400> SEQUENCE: 147

```
Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Asn Asn Leu Cys Asp Pro Ala
65                  70                  75                  80
Ser Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
        115                 120                 125
Pro Pro Ala Tyr Arg Pro Pro Asn His Pro Ile Leu Ser Thr Leu Pro
    130                 135                 140
Glu Thr Thr Val Val Arg Arg Arg Gly Arg Ser Pro Arg Arg Arg Thr
145                 150                 155                 160
Pro Ser Leu Glu His His His His His Cys
                165                 170
```

```
<210> SEQ ID NO 148
<211> LENGTH: 156
<212> TYPE: PRT
<213> ORGANISM: Hepatitis B virus

<400> SEQUENCE: 148

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Glu His His His His His His
145                 150                 155

<210> SEQ ID NO 149
<211> LENGTH: 9
<212> TYPE: PRT
<213> ORGANISM: Hepatitis B virus

<400> SEQUENCE: 149

Lys Lys Lys Lys Lys Lys Lys Lys Lys
1               5
```

METHODS AND COMPOSITIONS FOR CONTROLLING ASSEMBLY OF VIRAL PROTEINS

CROSS-REFERENCES TO RELATED APPLICATIONS

This application claims the benefit of U.S. Provisional Patent Application No. 61/532,986 entitled "METHODS AND COMPOSITIONS FOR CONTROLLING ASSEMBLY OF VIRAL PROTEINS" and filed on 9 Sep. 2011 for Miguel de los Rios, Stephanie de los Rios, Jacek Ostrowski, Kenneth J. Oh, and Ilan Zipkin, which is incorporated herein by reference.

FIELD

This invention relates to manipulation of viral capsids and more particularly relates to therapeutic preparations using core protein modified viral capsids.

BACKGROUND

Description of the Related Art

Viral protein-based therapeutic agents represent promising new drugs for the treatment of various diseases and disorders including cancer, infectious diseases, neurological disorders, inflammation and immune disorders, and cardiovascular disease. These drugs can result from the encapsulation of a therapeutic agent inside viral proteins, or from the genetic or biochemical attachment of therapeutic agents to viral proteins. However, generation of drugs derived from viral proteins requires controlled synthesis and efficient assembly of such proteins. Viral capsid particles, composed of many copies of a viral protein (or proteins), typically self-assemble when their subunit proteins are expressed in vivo or in vitro, or when purified biochemically. Because of this propensity to self-assemble, these particles are difficult to manipulate for purposes of drug delivery or ligand display. For example, phage display for screening of peptide or protein activity requires concomitant expression of the ligand(s) to be displayed on the phage particle surface in the same cell as the particle subunit itself, often as a fusion protein. Challenges in generating drugs from viral capsid particles include controlling what therapeutic agent is associated with the particle, and in what manner and location it is associated.

As such, there is an ongoing need for systems in which the assembly of viral capsid particles can be controlled more specifically and independently of the subunit protein expression system.

SUMMARY

From the foregoing discussion, it should be apparent that a need exists for a method and composition that control the assembly of viral subunit proteins. Beneficially, such method and composition would enable the modification of the viral subunit protein including for therapeutic use.

The present invention has been developed in response to the present state of the art, and in particular, in response to the problems and needs in the art that have not yet been fully solved by currently available methods and compositions. Accordingly, the present invention has been developed to provide a method and composition for controlling the assembly of viral subunit proteins independently of the viral protein expression system that overcome many or all of the above-discussed shortcomings in the art.

The present disclosure is directed, at least in part, to methods and compositions for controlling self-assembly of viral core proteins to form a viral capsid (also referred to herein as a "nanocage"). It is now appreciated that self-assembly of viral capsids can be controlled by introducing certain modifications into a viral core protein to maintain the viral core proteins in a manipulatable or oligomeric form (e.g., a non-caspid structure) and/or the exposing modified viral core protein maintained in a denaturing solution to certain conditions that trigger a self-assembly reaction.

In one aspect, the disclosed methods provide a method for assembling a modified viral core protein (e.g., a modified Hepatitis B Virus (HBV) core protein) into a viral capsid structure. The method includes providing a modified HBV core protein in a solution comprising a denaturing agent and adding a reducing agent to the solution to form an assembled capsid structure. The modified viral core protein may include at least one mutation or modification that can substantially prevent assembly of the viral core proteins until assembly is desired. For example, a modified HBV viral core protein may comprise a cysteine residue, e.g., a cysteine residue in the spike region of the HBV structural core, which is capable of forming a disulfide bond to maintain the protein in a locked, open state under denaturing conditions. Assembly of the viral core proteins into a viral capsid may be triggered, for example, by contacting the viral core proteins with a reducing agent. In some embodiments, capsid self-assembly may be further controlled by reducing the concentration of a denaturant present in the assembly solution (e.g., diluting a first concentration of denaturant to a second concentration of denaturant). The method may also include adding a negatively-charged polymer to the assembly solution.

In another aspect, the disclosed methods provide a method of controlling assembly of a modified viral core protein (e.g., a modified HBV core protein) into a capsid structure that do not require a cysteine modification to control assembly. The method includes providing a modified HBV core protein in a solution comprising a denaturing agent and diluting the denaturing agent in the solution to form an assembled capsid. Reducing agents are not required in this method to initiate capsid formation because there are no constraining disulfide bonds present. The method may also include adding a negatively-charged polymer to the assembly solution.

In each of the methods disclosed herein, therapeutic agents may be encapsulated into the assembled capsid structure during the assembly process. In some embodiments, a therapeutic agent may be attached (e.g., covalently attached) to the HBV core proteins while the core proteins are in the locked, open state. In other embodiments, a therapeutic agent may be added to the assembly reaction and encapsulated into the assembled capsid by diffusion (e.g., the therapeutic agent is not bound to the HBV core protein, but based on concentration of agent in the solution is captured in the assembled capsid during assembly). Exemplary therapeutic agents include nucleic acid drugs (e.g., siRNAs, shRNAs, antisense nucleic acids, etc.), peptides, proteins, and small molecules.

Claims appended to this disclosure are incorporated by reference and form part of this disclosure. Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
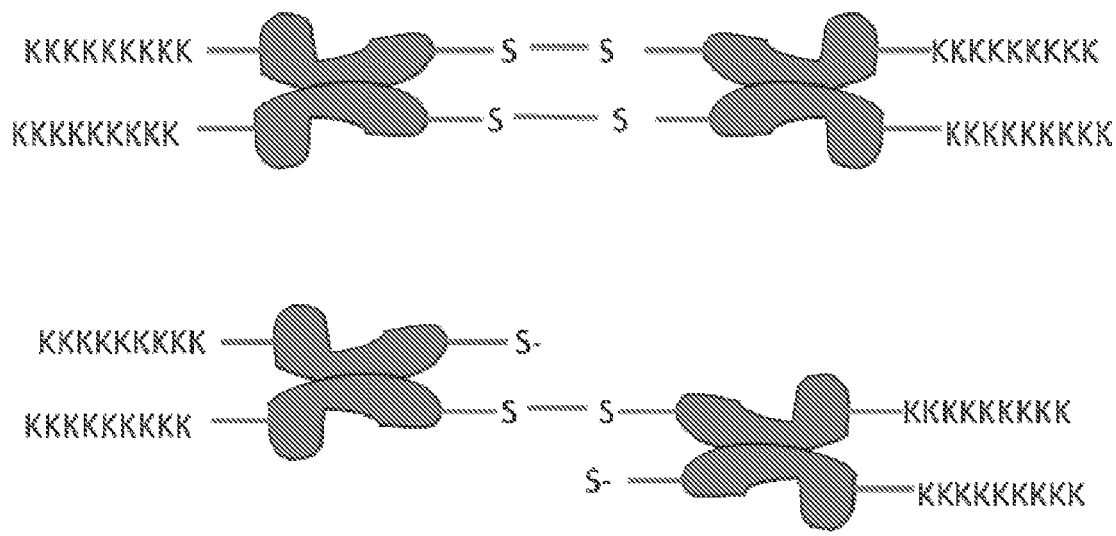
FIG. 1 is a schematic depicting modified HBV core protein dimers with a polylysine tail (e.g., a K9 tail SEQ ID NO: 149) in a locked state.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to impart a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. Additionally, the order in which a particular method occurs may or may not strictly adhere to the order of the corresponding steps shown.

The present disclosure is directed, at least in part, to methods and compositions for controlling self-assembly of modified viral core proteins into a viral capsid structure. For example, in one embodiment, the rate of viral core protein self-assembly may be controlled. In another embodiment, viral core protein self-assembly may be essentially delayed until a point at which self-assembly is desired. The viral core protein may, in some cases, be conjugated or loaded with a therapeutic agent prior to assembly, for example, to control the amount of drug encapsulated in each capsid. It is contemplated herein that one or more regions of the viral core protein may be more easily conjugated or loaded with a therapeutic agent prior to nanocage formation as compared to after nanocage formation. For example, in certain embodiments, a viral core protein may be loaded, prior to assembly, with a nucleic acid therapeutic agent, e.g., to form a chimeric therapeutic. Also advantageously, nanocages of high purity (e.g., low polydispersity and low fraction of non-assembled viral core protein) can be prepared using the disclosed methods. Self-assembly of the viral core proteins may be triggered, for example, by contacting the viral core proteins with a triggering agent (e.g., a reducing agent) and/or by reducing (e.g., diluting) the concentration of a denaturant present in the solution containing the viral core protein.

Throughout the specification, the assembled viral capsids contemplated herein may be referred to as "capsids," "nanocages," "cages," "particles," "therapeutic particles," and "therapeutic chimeric particles."

Self-Assembly of Viral Capsids

The methods and compositions contemplated herein provide control over viral core protein (e.g., Hepatitis B Virus core protein) self-assembly into a viral capsid. For example, in various embodiments the disclosed methods for controlling self-assembly of modified viral core proteins into viral capsids include: (1) exposing a modified viral core protein to a reducing agent; (2) a combination of exposing a modified viral core protein to a reducing agent and diluting the denaturant in which the viral core protein is stored (e.g., to maintain a non-assembled state); and (3) diluting the denaturant of the storage buffer without addition of a reducing agent.

It is contemplated herein that in some embodiments of the disclosed methods of assembling a viral capsid, e.g., comprising modified HBV core protein, the methods some self-assembly do not rely on ionic strength of an assembly solution (e.g., by raising the ionic strength of the assembly solution, e.g., by adding NaCl to promote self-assembly of a viral capsid).

As provided herein, a viral core protein may be modified such that formation of an assembled capsid structure (e.g., nanocage formation) can be essentially inhibited until desired. For example, the modification may allow the viral core protein to oligomerize to form a multimer of viral core proteins. For instance, in some cases, two viral core proteins may form a dimer, three viral core proteins may form a trimer, and four viral core proteins may form a tetramer. The multimers may be homomultimeric or heteromultimeric. Without wishing to be bound by any theory, it is believed that oligomerization of the viral core protein can essentially prevent participation of the viral core protein in capsid formation (e.g., prevent the natural propensity of self-assembly of viral core proteins). When the modified viral core protein is in an oligomeric form, the modified viral core protein may be described as being in a locked state, which prevents capsid assembly.

In certain embodiments, a viral core protein may be modified to contain a moiety that can be used to couple a first viral core protein to a second viral core protein into an oligomeric form or locked state. For example, a first viral core protein may be modified to contain a cysteine residue that can form a disulfide bridge with a second viral core protein. In some embodiments, the modification may comprise a substitution mutation or an insertion mutation within the viral core protein to induce oligomeric formation. The modification may occur at any suitable location in the core protein amino acid sequence. In certain embodiments, the modification is located on the surface of the first viral core protein so that the modification can interact with a second viral core protein inducing oligomer formation.

Virus core protein, and may also include Human Papilloma Virus (HPV) type 6 L1 and L2 protein and cowpea chlorotic mottle virus coat protein.

An exemplary viral core protein is Hepatitis B Virus (HBV) core protein (also referred to herein as "C-protein" or "CP"). It may be appreciated that different strains of HBV may have slight variations in the sequence of C-protein, and that any strain of HBV C-protein can be utilized. Exemplary sequences of HBV core protein include SEQ ID NO: 1 and 2, with amino acid sequence 1 to 183 corresponding to NCBI Protein Database accession numbers BAD86623 and AY741795, respectively:

```
                                                     (SEQ ID NO: 1)
MDIDPYKEFGASVELLSFLPSDFFPSIRDLLDTASALYREALESPEHCS

PHHTALRQAILCWGELMNLATWVGSNLEDPASRELVVSYVNVNMGLKIR

QLLWFHISCLTFGRETVLEYLVSFGVWIRTPPAYRPPNAPILSTLPETT

VVRRRGRSPRRRTPSPRRRRSQSPRRRRSQSRE
                                                     (SEQ ID NO: 2)
MDIDPYKEFGATVELLSFLPSDFFPSVRDLLDTASALYREALESPEHCS

PHHTALRQAILCWGELMTLATWVGNNLEDPASRDLVVNYVNTNMGLKIR

QLLWFHISCLTFGRETVLEYLVSFGVWIRTPPAYRPPNAPILSTLPETT

VVRRRGRSPRRRTPSPRRRRSQSPRRRRSQSRESQC
```

The corresponding nucleic acid sequence for SEQ ID NO: 1 and 2 are shown below, respectively:

```
Nucleic acid sequence for SEQ ID NO: 1
                                                     (SEQ ID NO: 3)
atggacattg acccttataa agaatttgga gcttctgtgg agttactctc ttttttgcct tctgactttt ttccttctat tcgagatctc ctcgacaccg cctccgctct gtatcgggag gctttagagt ctccggaaca ttgttcacct caccatacag cactcaggca agctattctg tgttggggtg agttaatgaa tctggccacc tgggtgggaa gtaatttgga agatccagca tccagggaat tagtagtcag ctatgtcaat gttaatatgg gcctaaaaat cagacaacta ctgtggtttc acatttcctg tcttactttt ggaagagaaa ctgttcttga gtatttggtg tcttttggag tgtggattcg cactcctcct gcttacagac caccaaatgc ccctatctta tcaacacttc cggaaactac tgttgttaga cgacgaggca ggtcccctag aagaagaact ccctcgcctc gcagacgaag gtctcaatcg ccgcgtcgca gaagatctca atctcgggaa tctcaatgtt ag Nucleic acid sequence for SEQ ID NO: 2
                                                     (SEQ ID NO: 4)
atggacattg atccttataa agaatttgga gctactgtgg agttactctc gtttttgcct tctgacttct ttccttcagt acgagatctt ctagataccg cctcagctct gtatcgggaa gccttagagt ctcctgagca ttgttcacct caccatactg cactcaggca agcaattctt tgctgggggg aactaatgac tttagccacc tgggtgggtg gtaatttgga agatccaata tccagagacc tagtagtcag ttatgttaac actcatatgg gcctaaagtt caggcaacta ttgtggtttc acatttcttg tctcactttt ggaagagaaa cggtcataga gtatttggtg tctttcggag tgtggattcg cactcctcta gcttatagac caccaaatgc ccctatctta tcaacacttc cggagactac tgttgttaga cgacgaggca ggtcccctag aagaagaact ccctcgcctc gcagacgaag gtctcaatcg ccgcgtcgca caaatctca atctcgggga tctcaatgtt ag
```

Any viral core protein that is capable, either alone or with another viral core protein, of self-assembling into a viral capsid is suitable for use in the disclosed methods. Exemplary viral core proteins include hepatitis core proteins such as human and duck Hepatitis B Virus core protein, Hepatitis C The skilled person would understand that a viral core protein may exist as a monomer (e.g., the viral core protein may comprise a single amino acid chain) or as a dimer (e.g., the viral core protein may comprise two amino acid chains). A dimer may be a homodimer or a heterodimer.

When the viral core protein is a HBV core protein, the skilled person would understand that HBV core proteins naturally form dimers in solution. Because HBV core proteins naturally form dimers, to prevent capsid structure assembly (e.g., nanocage formation), the HBV core protein may be modified to generate HBV core protein dimer-dimer complexes, as shown in FIG. 1A-B.

In certain embodiments, HBV core protein dimer-dimer complexes may be formed by modifying the spike region of the HBV core protein sequence. The spike region of the HBV core protein comprises from about amino acids 74 to 84 of SEQ ID NO: 1 or SEQ ID NO: 2. In certain embodiments, the spike region of a HBV core protein is modified to comprise a cysteine residue. For example, the spike region of an HBV core protein may be modified to comprise a cysteine residue at amino acid position 77, 79 or 80 of SEQ ID NO: 1 or SEQ ID NO: 2. It is contemplated herein that the introduction of a cysteine residue into the spike region (e.g., a E77C mutation) locks the HBV core protein dimer into a conformation that is not competent for self-assembly into nanocages due to the formation of a disulfide bond. Upon reduction of this disulfide bond, the protein dimer is conformationally free to associate with other core protein dimers and self-assemble into nanocages.

In an embodiment, the method for controlling assembly of HBV core proteins into viral capsids comprises exposing a modified viral core protein to a reducing agent without diluting the denaturant (e.g., the denaturant present in the buffer used to store the modified HBV core protein). The self-assembly method includes without limitation: providing a modified HBV core protein in a solution comprising a denaturing agent and adding a reducing agent to the solution to form an assembled capsid structure. Exemplary modified HBV core proteins comprise a cysteine in the spike region as described herein. For example, a core protein modified to contain a cysteine residue within the spike region, e.g., at amino acid position 77 of SEQ ID NO: 1 or SEQ ID NO: 2 and a poly-lysine tail, rapidly forms strong cages upon the addition of a reducing agent. Other exemplary modified core proteins that form viral capsids following the addition of a reducing agent are described below. For these modified core proteins, the presence of reducing agent initiates cage formation in the presence of denaturant (e.g., 2-6 M urea).

In some embodiments the method for controlling assembly of HBV core proteins into viral capsids includes exposing a modified viral core protein to a reducing agent and diluting the denaturant present in the assembly solution. The self-assembly method includes without limitation: (1) providing a modified HBV core protein in a solution comprising a denaturing agent; (2) adding a reducing agent to the solution; and (3) diluting the denaturant in the solution from a first concentration of denaturant to a second concentration of denaturant, thereby to form an assembled capsid structure. In some embodiments, the denaturant may be diluted prior to addition of the reducing agent. In other embodiments, the denaturant may be diluted after the addition of the reducing agent.

Modified HBV core proteins that self-assemble to form viral capsids following the addition of a reducing agent and dilution of the denaturant include without limitation modified core proteins that comprise one or more stabilizing and/or destabilizing mutations as described below. In some embodiments, exemplary modified HBV core proteins comprise a cysteine in the spike region and one or more stabilizing and/or destabilizing mutations in core protein as described below.

In certain embodiments the method for controlling assembly of HBV core proteins into viral capsids includes diluting the denaturant without adding a reducing agent. The self-assembly method includes without limitation: providing a modified HBV core protein in a solution comprising a denaturing agent and diluting the denaturant in the solution to form an assembled capsid structure. Modified HBV core proteins that self-assemble following dilution of the denaturant may in some instances not contain cysteine residues that form disulfide bonds. The weak protein-protein interactions that exist between these modified HBV cores are sufficient to prevent nanocage formation in the presence of a denaturant and subsequent dilution of the denaturant (e.g., dilution by about 25%, 50%, 75%, or 80% of the starting concentration of denaturant) can trigger nanocage formation. Exemplary non-limiting modified HBV core proteins are described below.

A viral core protein may be essentially inhibited from self-assembly by subjecting the viral core protein to conditions that destabilize self-assembly and/or stabilize the non-assembled form or locked form of the viral core protein. For example, a denaturant may be used to prevent self-assembly of the viral core protein. In each of the foregoing embodiments, the HBV core protein may be maintained in a storage buffer that contains a denaturant (e.g., 2-6 M urea) prior to initiation of capsid assembly.

Any denaturant and concentration of denaturant may be used that is suitable for essentially preventing self-assembly of the viral core protein. In some embodiments, one or more chaotropic agents, detergents, lyotropic agents, organic denaturants, and/or detergents may be used as the denaturant.

Non-limiting examples of chaotropic agents include urea, thiocyanate salts (e.g., guanidinium thiocyanate (GITC)), trichloroacetate salts, guanidine hydrochloride (GuHCl), nitrate salts, and perchlorate salts (e.g., lithium perchlorate).

Non-limiting examples of lyotropic agents include sulfate salts, phosphate salts, and acetate salts.

Non-limiting examples of organic denaturants include acetonitrile, methanol, ethanol, and trifluoroethanol (TFE).

Non-limiting examples of detergents include anionic, cationic, nonionic, or zwitterionic, detergents. Anionic detergents may include, for example, deoxycholic acid, cholic acid, and sodium dodecyl sulfate (SDS). Cationic detergents may include, for example, cetyltrimethylammonium bromide (CTAB). Nonionic detergents may include, for example, digitonin, triton, and tween. Zwitterionic detergents may include, for example, CHAPS.

In some embodiments, a denaturant may be used in combination with a modification to a viral core protein to essentially prevent self-assembly, e.g., when a viral core protein can form a particularly stable nanocage.

In embodiments that employ a disulfide bridge to prevent nanocage formation, an oxidizing environment may be used to stabilize the disulfide bridge. In some embodiments, oxygen gas dissolved in solution may be sufficient to maintain an oxidizing environment. However, it should be understood that any suitable oxidant may be added that maintains an oxidizing environment yet does not damage the viral core protein. A non-limiting example of an oxidant is iodine.

Self-assembly of the viral core proteins may be triggered at a desired point in time. For example, in the case of a viral core protein in which a reducible moiety is used to prevent self-assembly (e.g., a disulfide bond), a reducing agent may be used to trigger self-assembly. Thus, a disulfide bond may be broken using a thiol such as beta-mercaptoethanol (BME), tris(2-carboxyethyl)phosphine (TCEP), glutathione (GSH), dithiothreitol (DTT), 2mercaptoyethylamine (BMA), and/or free cysteine. Other suitable thiols will be known to those of ordinary skill in the art. In some instances, a protein such as thioredoxin may be used to break the disulfide bond.

In some embodiments, the reducing agent may be added in an excess molar ratio relative to the viral core protein. The range of reducing agent may be from about 0.1 molar equivalent to about 100 molar equivalents. For instance, in some cases, at least about 1 molar equivalent, at least about 4 molar equivalents, at least about 10 molar equivalents, at least about 20 molar equivalents, at least about 30 molar equivalents, or at least about 40 molar equivalents of the reducing agent relative to the viral core protein may be added. In some embodiments, the concentration of the reducing agent may be from about 0.1 molar equivalent to about 100 molar equivalents, from about 1 molar equivalent to about 100 molar equivalents, from about 1 molar equivalent to about 50 molar equivalents, from about 10 molar equivalent to about 100 molar equivalents, from about 10 molar equivalent to about 50 molar equivalents, or from about 10 molar equivalents to about 20 molar equivalents.

In embodiments that employ a denaturant to at least partially inhibit self-assembly of the capsid, reducing the concentration of the denaturant (e.g., removing at least some of the denaturant and/or diluting the denaturant) may be used to trigger self-assembly of the viral core protein. For example, the concentration of denaturant may be reduced by about at least 10%, at least 20%, least 25%, at least 50%, at least 75%, at least 80%, or at least 90%. In certain embodiments the concentration of denaturant may be reduced in the range of from about 10% to about 90%.

As described herein, in certain embodiments, the denaturant may be diluted from a first concentration to a second concentration to promote capsid formation during the assembly reaction. Dilution to the second concentration may include one or more dilution steps (e.g., one, two, three, four, five or more dilution steps). For example, prior to reducing the concentration of the denaturant (e.g., diluting the denaturant), the denaturant may have a concentration between about 2 M and about 8 M, between about 2 M and about 6 M, between about 2 M and about 4 M, between about 4 M and about 6 M, and between about 4 M and about 8 M, or any integer disposed within said ranges. After reducing the concentration of the denaturant (e.g., diluting the denaturant), the denaturant may have a concentration between about 0.25 M and about 4 M, between about 0.25 M and about 2 M, between about 0.25 M and about 1 M, between about 0.5 M and about 4 M, between about 1 M and about 4M, and in some cases less than about 0.25 M, or any integer disposed within said ranges. In some embodiments, the denaturing agent may be diluted prior to addition of the reducing agent. In other embodiments, the denaturing agent may be diluted after the addition of the reducing agent.

The methods of regulating assembly of a viral capsid structure may further comprise adding a negatively-charged (e.g., anionic) polymer to the assembly solution. In certain embodiments, the negatively-charged polymer is an RNA or DNA therapeutic agent (e.g., a siRNA) that may be encapsulated in the capsid. In other embodiments, the negatively charged polymer may include phosphonic acid, sulfonic acid, acrylic acid, maleic acid, sulfates and/or phosphates. Negatively-charged polymers may also include, but are not limited to poly(vinylphosphonic acid), poly(vinylsulfonic acid, sodium salt), poly(4-styrenesulfonic acid) ammonium salt, poly(4-styrenesulfonic acid) lithium salt, poly(4-styrenesulfonic acid), poly(4styrenesulfonic acid-co-maleic acid) sodium salt, polyanetholesulfonic acid sodium salt, polyepoxysuccinic acid, poly(2-acrylamido-2-methyl-1-propanesulfonic acid), poly(2acrylamido-2-methyl-1-propanesulfonic acid-co-acrylonitrile) acrylonitrile, poly(Nisopropylacrylamide)-carboxylic acid terminated, poly(N-isopropylacrylamide-co-methacrylic acid), poly(N-isopropylacrylamide-co-methacrylic acid-co-octadecyl acrylate), poly(acrylamide-co-acrylic acid), poly(acrylic acid sodium salt), poly(acrylic acid), poly(acrylic acid), a partial sodium salt-graft-poly(ethylene oxide) cross-linked, poly(acrylic acid-co-maleic acid), poly(isobutylene-co-maleic acid) sodium salt, poly(methyl vinyl etheralt-maleic acid monobutyl ester), poly(methyl vinyl ether-alt-maleic acid monoethyl ester), poly(methyl vinyl ether-alt-maleic acid), poly(styrene-alt-maleic acid) sodium salt, poly(2-ethylacrylic acid), poly[(2-ethyldimethylammonioethyl methacrylate ethyl sulfate)-co-(1vinylpyrrolidone)], poly [ethyl acrylate-co-methacrylic acid-co-3-(1-isocyanato-1-methylethyl)a-methylstyrene], poly(bis(4carboxyphenoxy)phosphazene), poly(bis(4-carboxyphenoxy)phosphazene) disodium salt, poly(styrene)-block-poly(acrylic acid), lignosulfonic acid sodium salt, lignosulfonic acid, acetate sodium salt, lignosulfonic acid, sugared sodium salt, acrylic acid-co-methyl methacrylate polymers (AAMMA), poly(methyl acrylic acid) (PMAA), poly(ethyl acrylic acid) (PEAA), poly(propyl acrylic acid) (PPAA), poly(butyl acrylic acid) (PBAA) and heparin.

In certain embodiments, the negatively-charged polymer may be at least one of acrylic acid polymer, acrylic acid-co-methyl methacrylate polymers (AAMMA), poly(methyl acrylic acid) (PMAA), poly(ethyl acrylic acid) (PEAA), poly (propyl acrylic acid) (PPAA), and poly(butyl acrylic acid) (PBAA).

In some embodiments, cationic polymers may be added to the assembly solution. Cationic polymers may be amine-based such as poly(ethyleneimine) (e.g., PEI bases) or another poly-cationic amino acid. PEI based polymers may be branched and consist of primary, secondary, and tertiary amine groups with ratios of 25%, 50%, and 25%, respectively. Exemplary cationic polymers include, but are not limited to, poly(acrylamide-codiallyldimethylammonium chloride), poly(allylamine hydrochloride), poly (diallyldimethylammonium chloride), poly(dimethylamine-co-epichlorohydrin-coethylenediamine), poly (ethyleneimine) branched or linear, poly[bis(2-chloroethyl)ether-alt-1,3-bis[3-(dimethylamino)propyl]urea], poly (arginine), poly(lysine), and poly(histidine).

The pH of the assembly solution may be between about 7.0 to about 9.5. In exemplary methods, the pH of a solution may be between about 7.0 to about 9.0, between about 7.0 to about 8.5, between about 7.4 to about 8.0 and between about 7.4 to about 7.6. It is contemplated herein that the pH of an assembly solution may be adjusted during the assembly reaction (e.g., the pH may be at a first pH at the beginning of an assembly reaction (e.g., pH 9.5) and may be adjusted during the course of the assembly reaction to a second pH (e.g., pH 7.4)).

In some embodiments, the pH of the assembly solution may be at about pH 7.0 or lower, e.g., capsid assembly may be conducted at a pH of 6.8 or lower, 6.5 or lower, 6.3 or lower, or 6.0 or lower. In certain embodiments, the pH of the assembly solution may be from about 5.0 to about 7.0. It is contemplated herein that certain mutations may be introduced into the HBV core (e.g., a F18H or A137H mutation) to destabilize a capsid at the dimer-dimer interface at low pH, e.g., a pH below the pKa of histidine, e.g., 6.0. Without wishing to be bound by theory, it is contemplated that mutations in the HBV core protein introducing a histidine at the dimer-dimer interface would not be able to form cage a low pH (e.g., such modified core proteins may be locked into a open state at low pH, e.g., a pH of about 6.0 to about 7.0). In certain embodiments, capsid assembly may be controlled by modifying the pH of the assembly solution (e.g., pH may be lower to about 7.0 or lower to prevent capsid assembly and raised to about 7.0 or higher to promote capsid assembly).

In various embodiments, assembly of the viral core proteins to form nanocages occurs at a managed rate. For example, the number of molar equivalents of triggering agent (e.g., a reducing agent) and/or the dilution rate of a denaturant may be adjusted to achieve a desired rate of self-assembly. In some case, at least about 95% of the viral core proteins may be self-assembled in less than about 3 hours, in less than about 2 hours, in less than about 1 hour, in less than about 30 minutes, in less than about 15 minutes, or in less than about 10 minutes.

The formation of nanocages (e.g., viral capsids) may also be measured. For instance, dynamic light scattering (DLS) may be used to measure the size of particles in solution (described in more detail in the Examples). In some embodiments, the assembled viral core proteins (i.e., the nanocages) have a smaller size as measured by DLS than the non-assembled viral core proteins. The average particle radius of the nanocages may be between about 10 nm and about 100 nm, between about 10 nm and about 50 nm, between about 15 nm and about 50 nm, between about 15 nm and about 40 nm, between about 15 nm and about 30 nm and between about 15 nm and about 20 nm.

The viral capsids formed by self-assembly of the viral core proteins may sometimes be purified. In certain embodiments, the assembled viral capsids are purified by size exclusion chromatography, centrifugation, and/or filtering. The methods contemplated herein may allow nanocages (e.g., viral capsids) to be prepared with high purity even in the absence of purification steps. For example, in some embodiments, particles with a polydispersity of less than about 20%, less than about 15%, or less than about 10% can be prepared. In some embodiments, particles with a polydispersity of between about 5% and about 20%, between about 10% and about 20% and between about 5% and about 15% can be prepared.

It is contemplated herein that the assembled viral capsid particles disclosed herein are substantially non-replicating and do not substantially incorporate attenuated wild-type virus. The viral core proteins may be designed to be substantially non-immunogenic and/or may be designed so that once the particle starts to disintegrate, it is degraded quickly so as to limit any potential immune response.

The assembled viral capsids contemplated herein may be substantially spherical and/or may be icosahedral in form. In some embodiments, the modified HBV core protein may comprise the first 149 amino acids of SEQ ID NO: 1 or SEQ ID NO: 2 as described herein. When a viral core protein includes about 149 amino acids, combined with a tail portion as discussed below, a capsid or cage structure with, e.g., a substantial T=4 geometry may be formed from, e.g., a plurality of modified viral core proteins.

In certain embodiments, the modified HBV core protein may comprise the first 138 amino acids of SEQ ID NO: 1 or SEQ ID NO: 2 as described herein. When a viral core protein includes about 138 amino acids, combined with a tail portion as discussed below, a capsid or cage structure with, e.g., a substantial T=3 geometry may be formed from, e.g., a plurality of modified viral core proteins.

It is also contemplated herein that any cleavable chemical species capable of coupling a first viral core protein to a second core protein may be used to prevent nanocage formation. For example, in some cases, a first viral core protein may contain an aldehyde group and a second viral core protein may contain a hydrazine group. The aldehyde group and the hydrazine group may react to form a hydrazone group that couples the first viral core protein to the second viral core protein. In some embodiments, a hydrazone group may be cleaved by contacting the viral core proteins with a solution having a pH of less than about 7, or in some embodiments less than about 6.

Additional cleavable chemical species that may be used to modify a viral core protein to maintain it in the locked state and regulate capsid assembly include without limitation the use of photocleavable linkers; chelating linkers; ssDNA linkers; dsDNA linkers; peptide linkers; autocleavable linkers; and saccharide linker. For example, photocleavable linkers such as bismaleimide may be used to lock to viral proteins in an open state to prevent assembly. The photocleavable linker may be cleaved by the application of light to trigger cage formation. Chelating linkers, e.g., a maleimide linkage on a first viral protein and a chelating moiety on a second viral protein, may be used to create a metal and linker complex to lock the two viral proteins in an open state to prevent assembly. Cage formation may be regulated by removing the metal. DNA linkers such as (ss) single-stranded or (ds) double-stranded DNA linker may also be used. For example, a cleavable linker such as bis-maleimide may include either a ssDNA or dsDNA between the two maleimide moieties. The ssDNA or dsDNA linker may be cleaved with an endonuclease that triggers nanocage formation. DsDNA linkers can also be broken by the addition of heat to the melting point of the dsDNA. Similarly, peptide linkers between two maleimide moieties may be used and subsequently cleaved by the addition of an endoprotease. Saccharide linkers may also be used between two maleimide moieties and subsequently cleaved by the addition of NaIO4 to trigger cage formation.

Modified Viral Core Protein

The wild-type HBV core protein is typically 183 amino acids (referred to herein as "core protein 183" or "CP183"). The amino-terminal 149 amino acids form a globular-fold or structural core. Provided herein, for example, is a structural core portion of an HBV core protein based on amino acids 1-149 of SEQ ID NO: 1 or SEQ ID NO: 2 (referred to herein as "structural core portion," "core protein 149" or "CP149"), that may include one or more modifications. The structural core portions of SEQ ID NO: 1 and SEQ ID NO: 2, respectively, are shown below:

CP149 based on SEQ ID NO: 1 has the following amino acid sequence:

(SEQ ID NO: 5)
MDIDPYKEFGASVELLSFLPSDFFPSIRDLLDTASALYREALESPEHCSPHHTALRQAIL

CWGELMNLATWVGSNLEDPASRELVVSYVNVNMGLKIRQLLWFHISCLTFGRETVLEYLV

SFGVWIRTPPAYRPPNAPILSTLPETTVV

CP149 based on SEQ ID NO: 2 has the following amino acid sequence:

(SEQ ID NO: 6)
MDIDPYKEFGATVELLSFLPSDFFPSVRDLLDTASALYREALESPEHCSPHHTALRQAILCWGELMTLAT

WVGNNLEDPASRDLVVNYVNTNMGLKIRQLLWFHISCLTFGRETVEYLVSFGVWIRTPPAYRPPNAPIL

STLPETTVV

The term "portion" when used in reference to a core protein refers to a fragment of that protein. The term "core protein" or "CP" followed by a number refer to an amino-terminal portion of a HBV core protein. For example, CP183 refers to HBV core protein with 183 amino acids (e.g., a wild-type HBV core protein) and CP149 refers to a HBV core protein with the amino-terminal 149 amino acids (e.g., a structural core portion of an HBV core protein).

It is noted that in some embodiments, a structural core portion may include the first amino-terminal 138 amino acids of an HBV core protein. It will be appreciated that a contemplated modified structural portion of a viral core protein may include amino acids 1-138 of SEQ ID NO: 1 or SEQ ID NO: 2 (referred to herein as "core protein 138" or "CP138"), that may include one or more modifications as described herein. The CP138 sequences corresponding to SEQ ID NO:1 and SEQ ID NO: 2 are shown below.

CP138 based on SEQ ID NO: 1 has the following amino acid sequence:

(SEQ ID NO: 7)
MDIDPYKEFGASVELLSFLPSDFFPSIRDLLDTASALYREALESPEHCSPHHTALRQAILCWGELMNLAT

WVGSNLEDPASRELVVSYVNVNMGLKIRQLLWFHISCLTFGRETVLEYLVSFGVWIRTPPAYRPPNAP

CP138 based on SEQ ID NO: 2 has the following amino acid sequence:

(SEQ ID NO: 8)
MDIDPYKEFGATVELLSFLPSDFFPSVRDLLDTASALYREALESPEHCSPHHTALRQAILCWGELMTLAT

WVGNNLCDPASRDLVVNYVNTNMGLKIRQLLWFHISCLTFGRETVLEYLVSFGVWIRTPPAYRPPNAP

The carboxyl-terminal 34 amino acids are typically referred to as the "tail portion" of the HBV core protein. A tail portion of the HBV core protein may be a wild-type tail portion (e.g., including the HBV core protein carboxyl-terminal 34 amino acids or a fragment thereof) or a synthetic tail portion (e.g., non-HBV core protein sequence, e.g., a lysine tail, arginine tail) or a combination thereof, as described below. In certain embodiments, a modified HBV core protein may include a histidine tag.

In certain embodiments, the modified HBV core protein is truncated at the carboxyl-terminus to remove all or part of the 34 amino acid tail portion. For example, the C terminal tail portion, which comprises from about amino acid residue 150 to about amino acid residue 183 of SEQ ID NO: 1 or SEQ ID NO: 2, may be truncated from the modified HBV core protein. The C-terminal tail portion comprises four arginine-rich repeats. It is contemplated herein that one, two, three or four of the arginine rich repeats may be truncated from the carboxyl-terminus of the modified HBV core protein. Exemplary truncation mutants (based on SEQ ID NO:2) include a mutation at CP170, wherein one arginine-rich repeat is truncated from the carboxy-terminus of the HBV core protein, as shown below (the remaining three arginine-rich repeats are underlined):

```
                                                          (SEQ ID NO: 9)
MDIDPYKEFGATVELLSFLPSDFFPSVRDLLDTASALYREALESPEHCSPHHTALRQAILCWGELMTLAT

WVGNNLEDPASRDLVVNYVNTNMGLKIRQLLWFHISCLTFGRETVLEYLVSFGVWIRTPPAYRPPNAPIL

STLPETTVVRRRGRSPRRRTPSPRRRRSQS.
```

A mutation at CP162, wherein two arginine-rich repeats are truncated from the carboxy-terminus of the HBV core protein, as shown below (the remaining two arginine-rich repeats are underlined):

```
                                                         (SEQ ID NO: 10)
MDIDPYKEFGATVELLSFLPSDFFPSVRDLLDTASALYREALESPEHCSPHHTALRQAILCWGELMTLAT

WVGNNLEDPASRDLVVNYVNTNMGLKIRQLLWFHISCLTFGRETVLEYLVSFGVWIRTPPAYRPPNAPIL

STLPETTVVRRRGRSPRRRTPS.
```

A mutation at CP155, wherein three arginine-rich repeats are truncated from the carboxy-terminus HBV core protein, as shown below (the remaining one arginine-rich repeat is underlined):

```
                                                         (SEQ ID NO: 11)
MDIDPYKEFGATVELLSFLPSDFFPSVRDLLDTASALYREALESPEHCSPHHTALRQAILCWGELMTLAT

WVGNNLEDPASRDLVVNYVNTNMGLKIRQLLWFHISCLTFGRETVLEYLVSFGVWIRTPPAYRPPNAPIL

STLPETTVVRRRGRS.
```

The structural core portion or CP149, as described above, may be generated when all four-arginine rich repeats are truncated from the carboxy-terminus.

For simplicity, the embodiments described herein exemplify truncations and/or modifications of the HBV C-protein variant SEQ ID NO: 2. It is appreciated that the same truncations and/or modifications can be engineered within HBV C-protein variant SEQ ID NO: 1.

As discussed above, in certain embodiments, structural core portion of an HBV core protein (e.g., amino acids 1-149 of an HBV core protein) may be modified to comprise a cysteine residue, for example, in the spike region of the HBV core protein, to control assembly of the capsid structure. The spike region comprises from about amino acid residue 74 to about amino acid residue 84 of SEQ ID NO: 1 or SEQ ID NO: 2. In certain embodiments, the spike region of an HBV core protein may be modified to comprise a cysteine residue at any amino acid position from about amino acid residue 74 to about amino acid residue 84 of SEQ ID NO: 1 or SEQ ID NO: 2, e.g., the HBV core protein may be modified to comprise a cysteine residue at amino acid position 77, 79 or 80 of SEQ ID NO: 1 or SEQ ID NO: 2. Exemplary structural core protein sequences comprising a cysteine residue in the spike region of SEQ ID NO:2 include CP149 with a glutamic acid to cysteine mutation at amino acid position 77 (underlined), which has the following amino acid sequence:

(SEQ ID NO: 12)
MDIDPYKEFGATVELLSFLPSDFFPSVRDLLDTASALYREALESPEHCSPHHTALRQAILCWGELMTLAT

WVGNNLCDPASRDLVVNYVNTNMGLKIRQLLWFHISCLTFGRETVLEYLVSFGVWIRTPPAYRPPNAPIL

STLPETTVV.

CP149 with a aspartic acid to cysteine mutation at amino acid position 78 (underlined) has the following amino acid sequence:

(SEQ ID NO: 13)
MDIDPYKEFGATVELLSFLPSDFFPSVRDLLDTASALYREALESPEHCSPHHTALRQAILCWGELMTLAT

WVGNNLECPASRDLVVNYVNTNMGLKIRQLLWFHISCLTFGRETVLEYLVSFGVWIRTPPAYRPPNAPIL

STLPETTVV.

CP149 with an alanine to cysteine mutation at amino acid position 80 (underlined) has the following amino acid sequence:

(SEQ ID NO: 14)
MDIDPYKEFGATVELLSFLPSDFFPSVRDLLDTASALYREALESPEHCSPH

HTALRQAILCWGELMTLATWVGNNLEDPCSRDLVVNYVNTNMGLKIRQLLW

FHISCLTFGRETVLEYLVSFGVWIRTPPAYRPPNAPILSTLPETTVV.

It is noted that in each of the embodiments discussed herein if the wild-type HBV core sequence is presented, it is contemplated that the wild-type HBV core sequence may be modified in the spike region to comprise a cysteine residue, e.g., to control assembly. It is also contemplated herein that the HBV core protein may be mutated to include a cysteine residue outside of the spike region in any location sufficient to form disulfide bonds with another HBV core protein to generate a locked HBV core protein dimer-dimer complex as illustrated in FIG. 1A-B.

In certain embodiments, a structural core portion of an HBV core protein may be also modified, for example, to (a) strengthen and further promote assembly of the viral core protein, e.g., HBV core protein monomers into a capsid (referred to herein as "stabilizing mutations"); (b) to destabilize the capsid structure; (c) enhance and promote the coating of one or more capsids with a layer comprising a lipid or lipid/cholesterol; (d) facilitate the attachment of other moieties, e.g., chemical modifiers and/or targeting agents; and/or (e) facilitate the disassembly of the entire capsid in the bloodstream following administration. Each of these modifications is discussed in detail below.

A modified structural core protein can be, in some embodiments, represented by SEQ ID NO: 15, where X, independently for each occurrence, represents an amino acid. It is understood that a contemplated viral core protein may include a structural portion represented by, e.g., SEQ ID NO: 15 and may additionally include a modified or unmodified tail portion, e.g., a modified C-terminal tail portion such as those described below.

(SEQ. ID. NO: 15)
MDIDPYKEFGATVXLLSXLPSDXFPSVRXLLDXASXXYREALESPEHXSPH

HTALRQAILXWGELMTLATWVGNNLXXPXSRDLVVNYVNTNMGLKIRQLLW

FHISXLTFGRETVLEXLVXXGXWIXTPPAXRPPNXPXLXTLPETTVV, wherein the X, at a given location, is selected from:
X at 14: X=E,H
X at 18: X=F,H
X at 23: X=F, C, H
X at 29: X=D, C
X at 33: X=T, C, H,
X at 36: X=A,H,
X at 37 X=L,C,H
X at 48: X=C,A
X at 61: X=C,A,
X at 77: X=E,C,
X at 78: X=D,C,S,E,
X at 79: X=P,C
X at 80: X=A, C
X at 107: X=C, A
X at 118: X=Y,H
X at 121: X=S,C
X at 122: X=F, H
X at 124: X=V, C
X at 127: X=R, C
X at 132: X=Y, A, V, I, F, C
X at 137: X=A, H
X at 139: X=I, A
X at 141: X=S, C Capsid Assembly Modifications In some embodiments, a HBV capsid may be formed from protein dimers. For example, intermolecular interactions between dimers may stabilize the assembly and may be formed by disulfide bonds, salt bridges, and hydrophobic interactions between proteins. In some embodiments, a structural core portion may include a mutation in interacting amino acid side chains to either stabilize and/or destabilize the interactions and therefore, the capsid or particle assembly. In certain embodiments, such mutations may affect the long-term stability of a capsid or particle formed from viral core proteins that include such viral structural portions. Such stabilizing and/or destabilizing mutations can be introduced, e.g., singly and/or in combination.

For example, stabilizing mutations may be introduced at amino acid positions 121 and/or 141 of a structural core portion of a HBV core protein (e.g., S121C and/or S141C of SEQ ID NO: 2) to form a disulfide bond, which may stabilize inter-dimer associations between viral protein core proteins. In some embodiments, a stabilizing mutation may be introduced at amino acid position 14 of a structural core portion of a HBV core protein (e.g., E141I of SEQ ID NO: 2). Stabilizing sequences based on CP162 of the HBV core protein variant SEQ ID NO: 2 include the following without limitation:

CP162 with E77C, S121C and S141C mutations in a SEQ ID NO: 2 variant

```
                                    (SEQ ID NO: 16)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AYRPPNAPIL CTLPETTVVR RRGRSPRRRT PS;
```

CP162 with E77C and E14H mutations in a SEQ ID NO: 2 variant

```
                                    (SEQ ID NO: 17)
MDIDPYKEFG ATVHLLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;
and
```

CP162 with E77C and S121C mutations in a SEQ ID NO: 2 variant

```
                                    (SEQ ID NO: 18)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AYRPPNAPIL STLPETTVVR RRGRSPRRRT PS.
```

Exemplary stabilizing mutation sequences shown above include a cysteine residue at amino acid position 77. It is contemplated herein that the amino acid 77 may be a glutamic acid. It is also contemplated herein that amino acid 77 may be a glutamic acid and that a cysteine residue may be introduced at another amino acid position within the spike region (e.g., from about amino acid 74 to about amino acid 84 of the spike region).

In certain embodiments, destabilizing mutations may be introduced into the structural core portion of a HBV core protein. Exemplary destabilizing mutations may be introduced at amino acid positions 18, 23, 33, 36, 37, 118, 122, 137, 132 and/or 139 of a structural core portion of a HBV core protein (e.g., F18H, F23H, T33H, A36H, L37H, Y118H, F122H, Y 132F, Y132A, Y132V, A137H, and/or I139A of SEQ ID NO: 2). Exemplary destabilizing sequences based on CP162 of the HBV core protein variant SEQ ID NO: 2 include the following:

CP162 with E77C and Y132A mutations in a SEQ ID NO:2 variant

```
                                    (SEQ ID NO: 19)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AARPPNAPIL STLPETTVVR RRGRSPRRRT PS;
```

CP162 with E77C and Y132V mutations in a SEQ ID NO: 2 variant

```
                                    (SEQ ID NO: 20)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AVRPPNAPIL STLPETTVVR RRGRSPRRRT PS;
```

CP162 with E77C and Y132F mutations in a SEQ ID NO: 2 variant

```
                                    (SEQ ID NO: 21)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AFRPPNAPIL STLPETTVVR RRGRSPRRRT PS;
```

CP162 with E77C and I139A mutations in a SEQ ID NO: 2 variant

```
                                    (SEQ ID NO: 22)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPAL STLPETTVVR RRGRSPRRRT PS;
```

CP162 with E77C and F18H mutations in a SEQ ID NO: 2 variant

```
                                    (SEQ ID NO: 23)
MDIDPYKEFG ATVELLSHLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;
```

CP162 with E77C and F23H mutations in a SEQ ID NO: 2 variant

```
                                    (SEQ ID NO: 24)
MDIDPYKEFG ATVELLSFLP SDHFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;
```

CP162 with E77C and T33H mutations in a SEQ ID NO: 2 variant

```
                                    (SEQ ID NO: 25)
MDIDPYKEFG ATVELLSFLP SDFFPSVRDL LDHASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;
```

CP162 with E77C and A36H mutations in a SEQ ID NO: 2 variant (SEQ ID NO: 26)
MDIDPYKEFG ATVELLSFLP SDFFPSVRDL LDTASHLYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;

CP162 with E77C and L37H mutations in a SEQ ID NO: 2 variant (SEQ ID NO: 27)
MDIDPYKEFG ATVELLSFLP SDFFPSVRDL LDTASAHYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;

CP162 with E77C and Y118H mutations in a SEQ ID NO: 2 variant (SEQ ID NO: 28)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEHLV

SFGVWIRTPP AYRPPNAPIL STLPETTVVR RRGRSPRRRT PS;

CP162 with E77C and F122H mutations in a SEQ ID NO: 2 variant (SEQ ID NO: 29)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SHGVWIRTPP AYRPPNAPIL STLPETTVVR RRGRSPRRRT PS;
and

CP162 with E77C and A137H mutations in a SEQ ID NO: 2 variant (SEQ ID NO: 30)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNHPIL STLPETTVVR RRGRSPRRRT PS.

Exemplary destabilizing mutation sequences shown above also include a cysteine residue at amino acid position 77. It is contemplated herein that the amino acid 77 may be a glutamic acid. It is also contemplated herein that amino acid 77 may be a glutamic acid and that a cysteine residue may be introduced at another amino acid position within the spike region (e.g., from about amino acid 74 to about amino acid 84 of the spike region).

In some embodiments, both stabilizing and destabilizing mutations may be introduced into the structural core portion of a HBV core protein. Exemplary structural core protein sequences with both stabilizing and destabilizing mutations based on CP162 of the HBV core protein variant SEQ ID NO: 2 include the following:

CP162 with E77C, Y132F, S121C and S141C mutations in a SEQ ID NO: 2 variant (SEQ ID NO: 31)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AFRPPNAPIL CTLPETTVVR RRGRSPRRRT PS;

CP162 with E77C, F18H, S121C and S141C mutations in a SEQ ID NO:2 variant (SEQ ID NO: 32)
MDIDPYKEFG ATVELLSHLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AYRPPNAPIL CTLPETTVVR RRGRSPRRRT PS;

CP162 with E77C, Y132A, S121C and S141C mutations in a SEQ ID NO:2 variant (SEQ ID NO: 33)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AARPPNAPIL CTLPETTVVR RRGRSPRRRT PS;
and

CP162 with E77C, A137H, S121C and S141C mutations in a SEQ ID NO:2 variant (SEQ ID NO: 34)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AYRPPNHPIL CTLPETTVVR RRGRSPRRRT PS.

Exemplary stabilizing and destabilizing mutation sequences shown above also include a cysteine residue at amino acid position 77. It is contemplated herein that the amino acid 77 may be a glutamic acid. It is also contemplated herein that amino acid 77 may be a glutamic acid and that a cysteine residue may be introduced at another amino acid position within the spike region (e.g., from about amino acid 74 to about amino acid 84 of the spike region).

In certain embodiments, the native cysteine residues at positions 48, 61, and/or 107 may also be mutated, (for example to an alanine), without substantially affecting the ability of the core protein to form a capsid or particle. Exemplary sequences based on a CP149 structural core portion of a HBV core protein variant based on SEQ ID NO: 2 include the following:

CP162 with E77C and C48A mutations in a SEQ ID NO:2 variant

```
                                              (SEQ ID NO: 35)
MDIDPYKEFGATVELLSFLPSDFFPSVRDLLDTASALYREALESPEHASP
HHTALRQAILCWGELMTLATWVGNNLCDPASRDLVVNYVNTNMGLKIRQL
LWFHISCLTFGRETVLEYLVSFGVWIRTPPAYRPPNAPILSTLPETTVV;
```

CP162 with E77C and C61A mutations in a SEQ ID NO:2 variant

```
                                              (SEQ ID NO: 36)
MDIDPYKEFGATVELLSFLPSDFFPSVRDLLDTASALYREALESPEHCSP
HHTALRQAILAWGELMTLATWVGNNLCDPASRDLVVNYVNTNMGLKIRQL
LWFHISCLTFGRETVLEYLVSFGVWIRTPPAYRPPNAPILSTLPETTVV;
```

CP162 with E77C and C107A mutations in a SEQ ID NO:2 variant

```
                                              (SEQ ID NO: 37)
MDIDPYKEFGATVELLSFLPSDFFPSVRDLLDTASALYREALESPEHCSP
HHTALRQAILCWGELMTLATWVGNNLCDPASRDLVVNYVNTNMGLKIRQL
LWFHISALTFGRETVLEYLVSFGVWIRTPPAYRPPNAPILSTLPETTVV;
```

CP162 with E77C, C48A and C61A mutations in a SEQ ID NO:2 variant

```
                                              (SEQ ID NO: 38)
MDIDPYKEFGATVELLSFLPSDFFPSVRDLLDTASALYREALESPEHASP
HHTALRQAILAWGELMTLATWVGNNLCDPASRDLVVNYVNTNMGLKIRQL
LWFHISCLTFGRETVLEYLVSFGVWIRTPPAYRPPNAPILSTLPETTVVD;
```

CP162 with E77C, C48A and C107A mutations in a SEQ ID NO:2 variant

```
                                              (SEQ ID NO: 39)
MDIDPYKEFGATVELLSFLPSDFFPSVRDLLDTASALYREALESPEHASP
HHTALRQAILCWGELMTLATWVGNNLCDPASRDLVVNYVNTNMGLKIRQL
LWFHISALTFGRETVLEYLVSFGVWIRTPPAYRPPNAPILSTLPETTVV;
```

CP162 with E77C, C61A and C107A mutations in a SEQ ID NO:2 variant

```
                                              (SEQ ID NO: 40)
MDIDPYKEFGATVELLSFLPSDFFPSVRDLLDTASALYREALESPEHCSP
HHTALRQAILAWGELMTLATWVGNNLCDPASRDLVVNYVNTNMGLKIRQL
LWFHISALTFGRETVLEYLVSFGVWIRTPPAYRPPNAPILSTLPETTVV;
``` and

CP162 with E77C, C48A, C61A and C107A mutations in a SEQ ID NO:2 variant

```
                                              (SEQ ID NO: 41)
MDIDPYKEFGATVELLSFLPSDFFPSVRDLLDTASALYREALESPEHASP
HHTALRQAILAWGELMTLATWVGNNLCDPASRDLVVNYVNTNMGLKIRQL
LWFHISALTFGRETVLEYLVSFGVWIRTPPAYRPPNAPILSTLPETTVV.
```

Modifications of the structural core portion of a viral core protein can include the introduction of, e.g., a pair of cysteines into a spike area of a formed dimer or the interface between dimers. For example, a first cysteine (e.g., amino acid 23) is introduced in the first position in order to form a disulfide bond with a second cysteine (amino acid 132 in this case) in a neighboring molecule. Similarly, the second position may also participate in a disulfide bond, allowing the dimer to participate in four disulfide bridges and a total of 180 stabilizing covalent interactions. At least four different types of disulfide bonds may be created:

For example, exemplary modified viral core proteins, that include a modified structural core portion, include the following:

HBV C-protein variant of SEQ ID NO: 2 comprising mutation 1: phenylalanine 23 to cysteine; tyrosine 132 to cysteine:

```
                                              (SEQ ID NO: 42)
MDIDPYKEFGATVELLSFLPSDCFPSVRDLLDTASALYREALESPEHCSP
HHTALRQAILCWGELMTLATWVGNNLEDPASRDLVVNYVNTNMGLKIRQL
LWFHISCLTFGRETVLEYLVSFGVWIRTPPACRPPNAPILSTLPETTVVR
RRGRSPRRRTPSPRRRRSQSPRRRRSQSRESQC;
```

HBV C-protein SEQ ID NO: 1 comprising mutation 1: phenylalanine 23 to cysteine; tyrosine 132 to cysteine:

```
                                              (SEQ ID NO: 43)
MDIDPYKEFGASVELLSFLPSDCFPSIRDLLDTASALYREALESPEHCSP
HHTALRQAILCWGELMNLATWVGSNLEDPASRELVVSYVNVNMGLKIRQL
LWFHISCLTFGRETVLEYLVSFGVWIRTPPACRPPNAPILSTLPETTVVR
RRGRSPRRRTPSPRRRRSQSPRRRRSQSRESQC;
```

HBV C-protein variant SEQ ID NO: 2 comprising mutation 2: aspartic acid 29 to cysteine; arginine 127 to cysteine:

```
                                              (SEQ ID NO: 44)
MDIDPYKEFGATVELLSFLPSDFFPSVRCLLDTASALYREALESPEHCSP
HHTALRQAILCWGELMTLATWVGNNLEDPASRDLVVNYVNTNMGLKIRQL
LWFHI
SCLTFGRETVLEYLVSFGVWICTPPAYRPPNAPILSTLPETTVVRRRGRS
PRRRTPSPRRRRSQSPRRRRSQSRESQC
```

HBV C-protein SEQ ID NO: 1 comprising mutation 2: aspartic acid 29 to cysteine; arginine 127 to cysteine:

```
                                              (SEQ ID NO: 45)
MDIDPYKEFGASVELLSFLPSDFFPSIRCLLDTASALYREALESPEHCSP
HHTALRQAILCWGELMNLATWVGSNLEDPASRELVVSYVNVNMGLKIRQL
LWFHISCLTFGRETVLEYLVSFGVWICTPPAYRPPNAPILSTLPETTVVR
RRGRSPRRRTPSPRRRRSQSPRRRRSQSRESQC;
```

HBV C-protein variant SEQ ID NO: 2 comprising mutation 3: threonine 33 to cysteine; valine 124 to cysteine:

(SEQ ID NO: 46)
MDIDPYKEFGATVELLSFLPSDFFPSVRDLLDCASALYREALESPEHCSP

HHTALRQAILCWGELMTLATWVGNNLEDPASRDLVVNYVNTNMGLKIRQL

LWFHISCLTFGRETVLEYLVSFGCWIRTPPAYRPPNAPILSTLPETTVVR

RRGRSPRRRTPSPRRRRSQSPRRRRSQSRESQC;

HBV C-protein SEQ ID NO: 1 comprising mutation 3: threonine 33 to cysteine; valine 124 to cysteine:

(SEQ ID NO: 47)
MDIDPYKEFGASVELLSFLPSDFFPSIRDLLDCASALYREALESPEHCSP

HHTALRQAILCWGELMNLATWVGSNLEDPASRELVVSYVNVNMGLKIRQL

LWFHISCLTFGRETVLEYLVSFGCWIRTPPAYRPPNAPILSTLPETTVVR

RRGRSPRRRTPSPRRRRSQSPRRRRSQSRESQC;

HBV C-protein variant SEQ ID NO: 2 comprising mutation 4: leucine 37 to cysteine; valine 120 to cysteine:

(SEQ ID NO: 48)
MDIDPYKEFGATVELLSFLPSDFFPSVRDLLDTASACYREALESPEHCSP

HHTALRQAILCWGELMTLATWVGNNLEDPASRDLVVNYVNTNMGLKIRQL

LWFHISCLTFGRETVLEYLCSFGVNIRTPPAYRPPNAPILSTLPETTVVR

RRGRSPRRRTPSPRRRRSQSPRRRRSQSRESQC;
and

HBV C-protein SEQ ID NO: 1 comprising mutation 4: leucine 37 to cysteine; valine 120 to cysteine:

(SEQ ID NO: 49)
MDIDPYKEFGASVELLSFLPSDFFPSIRDLLDTASACYREALESPEHCSP

HHTALRQAILCWGELMNLATWVGSNLEDPASRELVVSYVNVNMGLKIRQL

LWFHISCLTFGRETVLEYLCSFGVWIRTPPAYRPPNAPILSTLPETTVVR

RRGRSPRRRTPSPRRRRSQSPRRRRSQSRESQC.

It is contemplated herein that in each of the foregoing modified HBV core protein sequences, amino acid 77 may be a glutamic acid and a cysteine residue may be introduced into another location within the spike region, e.g., a cysteine residue may be substituted at about amino acid position 74 to about amino acid position 84, e.g., at amino acid position 78 or 80.

Capsid Attachment Site Modifications

In some embodiments, a structural core portion of the viral core protein may be modified to include a conjugation site that allows the attachment of a moiety, e.g., a chemical linker moiety such as a lipid linker moiety (e.g., a maleimide intermediate). For example, either of the amino acids cysteine or lysine may be placed in the structural core in such a way so that when formed in a capsid or particle these modifications may protrude away from the capsid surface, e.g., toward a plasma membrane.

In an embodiment, such modifications may permit the addition of one or more lipid linker moieties which can serve to promote or facilitate a lipid layer. The assembled viral capsids may comprise a partial or substantially complete coating disposed on the particle that includes one or more lipids. For example, at least one lipid molecule may covalently bound through a chemical linker moiety, e.g., a lipid linker moiety, to a viral core protein, e.g., to a structural core portion of a disclosed viral core protein. For non-limiting example, the lipid may be attached via bond or chemical linker moiety, to an engineered location on the structural core portion of the viral core protein, for example at amino acid position 77, 78 or 80 of a hepatitis B structural core portion, as described above.

In certain embodiments three positions on a structural core portion of a viral core protein may be used for the introduction of one or more cysteines and/or lysines, e.g., amino acid residue 77, glutamic acid to cysteine or lysine; amino acid residue 78, aspartic acid to cysteine or lysine; and/or amino acid residue 80, alanine to cysteine or lysine on a HBV core protein (e.g., SEQ ID NO: 2). In some embodiments such cysteine modifications may be further functionalized. Cysteine mutations may also be introduced at other locations in the C-protein. Exemplary modified structural core portions CP149 of a HBV core protein variant SEQ ID NO:2 include:

CP149 with a E77C mutation (underlined):

(SEQ ID NO: 12)
MDIDPYKEFGATVELLSFLPSDFFPSVRDLLDTASALYREALESPEHCSP

HHTALRQAILCWGELMTLATWVGNNLCDPASRDLVVNYVNTNMGLKIRQL

LWFHISCLTFGRETVLEYLVSFGVWIRTPPAYRPPNAPILSTLPETTVV;

CP149 with a D78C mutation (underlined):

(SEQ ID NO: 13)
MDIDPYKEFGATVELLSFLPSDFFPSVRDLLDTASALYREALESPEHCSP

HHTALRQAILCWGELMTLATWVGNNLECPASRDLVVNYVNTNMGLKIRQL

LWFHISCLTFGRETVLEYLVSFGVWIRTPPAYRPPNAPILSTLPETTVV;

CP149 with an A80C mutation (underlined):

(SEQ ID NO: 14)
MDIDPYKEFGATVELLSFLPSDFFPSVRDLLDTASALYREALESPEHCSP

HHTALRQAILCWGELMTLATWVGNNLEDPCSRDLVVNYVNTNMGLKIRQL

LWFHISCLTFGRETVLEYLVSFGVWIRTPPAYRPPNAPILSTLPETTVV;

CP149 with an D78S mutation (SEQ ID NO: 50)
MDIDPYKEFGATVELLSFLPSDFFPSVRDLLDTASALYREALESPEHCSP

HHTALRQAILCWGELMTLATWVGNNLESPASRDLVVNYVNTNMGLKIRQL

LWFHISCLTFGRETVLEYLVSFGVWIRTPPAYRPPNAPILSTLPETTVV;
and

CP149 with an D78E mutation (SEQ ID NO: 51)
MDIDPYKEFGATVELLSFLPSDFFPSVRDLLDTASALYREALESPEHCSP

HHTALRQAILCWGELMTLATWVGNNLEEPASRDLVVNYVNTNMGLKIRQL

LWFHISCLTFGRETVLEYLVSFGVWIRTPPAYRPPNAPILSTLPETTVV.

Contemplated lipid linker moieties may include those discussed herein. Exemplary lipid linker moieties may be formed from contacting e.g., a succinimidyl derivative such as succinimidyl-4-(p-maleimidophenyl)butyrate (SMPB) or m-maleimidobenzoyl-Nhydroxysuccinimide ester with a modified structural core portion of the viral core protein.

In an embodiment, a chemical linker, e.g., a bifunctional linker, may bind another moiety to a particle formed from viral core proteins that include a modified structure core portion, e.g., that include one or more cysteine residues. Exemplary chemical linkers include moieties such as those formed by contacting a cysteine residue with a maleimide-containing compound such as phosphatidylethanolamine-maleimide (PE-maleimide or PEmal). Phospholipids, for example, may be directly linked through a chemical linker to a modified structural core portion, e.g., to link a lipid molecule and/or a targeting agent.

An assembled capsid may have a layer or coating comprising one or more lipids, e.g., a neutral lipid, an anionic lipid, and/or a cationic lipid. For example, a neutral lipid and/or an amphipathic lipid, for example, a phospholipid such as phophatidyl serine, may be covalently bonded to a lipid linker moiety. Such covalently bound lipid molecules may guide the placement of a coating, e.g., that may include one more neutral lipids, and/or may include an anionic lipid that is surface neutral, such as POPG.

Exemplary phospholipids suitable for use include, but are not limited to, hydrogenated soy phosphatidylcholine (HSPC), egg phosphatidylcholine (EPC), phosphatidyl ethanolamine (PE), phosphatidyl glycerol (PG), phosphatidyl inositol (PI), monosialogangolioside, spingomyelin (SPM), distearoylphosphatidylcholine (DSPC), dimyristoylphosphatidylcholine (DMPC), or dimyristoylphosphatidylglycerol (DMPG).

In some embodiments, an assembled capsid contemplated herein may be coated with one or more lipids including one, two, or more of lipids such as palmitoyloleoylphosphatidylglycerol (POPG), hydrogenated soy phosphatidylcholine (HSPC). Contemplated lipids include PEG-phospholipids, including poly(ethylene glycol)-derivatized distearoylphosphatidylethanolamine (PEG-DSPE) and/or poly(ethylene glycol)-derivatized ceramides (PEG-CER).

Provided herein are assembled capsids that may include a coating comprising one or more lipids and cholesterol, for example, and may include various amounts of cholesterol, HSPC or POPG. The lipid coating may include about 5% to about 40% cholesterol, about 10% to about 80% HSPC and/or about 5% to about 80% POPG, or any specific percentage within said ranges. In some embodiments, a coating may comprise, for example, (a) about 20% cholesterol and about 80% HSPC; (b) about 50% cholesterol and about 50% HSPC; (c) about 20% cholesterol and about 20% HSPC and about 60% POPG; (d) about 50% cholesterol and about 50% POPG; (e) 20% cholesterol and 80% POPG; or (f) about 10% cholesterol and about 15% HSPC and about 65% POPG. In an embodiment, a coating may include about 20% cholesterol, about 20% HSPC and about 60% POPG.

A coating composition may have a coating to particle mass value of about 10% to about 60%, about 10% to about 50%, about 15 to about 40%, about 20% to about 35% of the total protein (w/w), or any specific percentage with the recited ranges. For example, a lipid coating composition may coat a particle at a mass value of about 30% to about 100% (w/w).

In various embodiments suitable ratios of protein:lipid for the coating process may range from approximately 1:1 protein:lipid (w:w) to approximately 1:30 protein:lipid (w:w). Protein:lipid rations may sometimes be from 0.1:1 to 1:100 or any intermediate ratio within such ranges.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine such as egg phosphatidylcholine or hydrogenated soy phosphatidylcholine, phosphatidylethanolamine, phosphatidylserine, phosphatidylinositol, phosphatidic acid, pahnitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, phosphatidyl glycerol, monosialoganlgolioside, spingomyelin, dimyristoylphosphatidylcholine, and dilinoleoylphosphatidylcholine. Other compounds lacking in phosphorus, such as sphingolipid, glycosphingolipid families, diacylglycerols, and (3-acyloxyacids, are also within the group designated as amphipathic lipids. Additionally, the amphipathic lipid described above can be mixed with other lipids including triglycerides and sterols.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, Nglutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). Examples of cationic lipids include, but are not limited to, N,N-dioleyl-N, N-dimethylammonium chloride (DODAC), dioctadecyldimethylammonium (DODMA), distearyldimethylammonium (DSDMA), N-(1-2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-Nhydroxyethyl ammonium bromide (DMRIE), 1,2-dilinoleyloxy-N,N-dimethylaminopropane (DLinDMA), 1,2-dilinolenyloxy-N,N-dimethylaminopropane (DLenDMA), and mixtures thereof. In certain embodiments, anionic lipids can be neutral on the surface with an internal negative charge.

Capsid Disassembly Modifications

Additional alterations or mutations may be made on, e.g., a viral structural core that may, for example, facilitate disassembly of a capsid or particle formed disclosed viral core proteins after, for example, administering in vivo. For example, mutations are contemplated that may introduce blood protease recognition sequences, e.g., protease recognition sites at hinge and loop regions. Such sequences can be inserted, for example, into the spike region of the HBV C-protein (e.g., replacing amino acids 79 and 80 with these 12 amino acid insertion loops. In some embodiments, a viral core protein may include up to about 40, or about 46 such insertion residues and may still, in some embodiments, be capable of forming a particle or capsid.

Exemplary blood protease recognition sequences include for example, thrombin (GPGAPGLVPRGS; SEQ ID NO: 52) and factor Xa (GPASGPGIEGRA; SEQ ID NO: 53). For example, contemplated HBV C-proteins from SEQ ID NO: 2 variant that comprise such a blood protease recognition sequence can be represented by:

CP162 comprising a E77C mutation and a thrombin recognition site introduced between amino acids 78 and 79:

```
                                      (SEQ ID NO: 54)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS;
and
```

CP162 comprising a E77C mutation and a factor Xa recognition site introduced between amino acids 78 and 79:

```
                                      (SEQ ID NO: 55)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT PS.
```

Modified Tail Portions

Various modifications of the terminal tails of the disclosed HBV core protein and truncation mutations or structural core portions thereof are contemplated. For example, the C-terminal tail of a hepatitis B core protein, can be engineered to, for example, provide appropriate properties for binding a nucleic acid and/or protein to the modified viral core protein. For example, a therapeutic chimeric is provided that includes a viral core protein with a modified tail portion and a nucleic acid associated with, e.g., bound to the modified tail portion.

The 34 amino C-terminal tail of the wild type HBV-C protein is presumed to hang inside the fully formed viral capsid and bind, e.g., a viral nucleic acid, and is shown below:

C-terminal tail amino acid sequence 150 to 183:

```
                                      (SEQ ID NO: 56)
RRRGRSPRRRTPSPRRRRSQSPRRRRSQSRESQC.
```

This wild type tail can be modified, truncated, and/or mutated to provide a modified tail portion, that, together with a structural core portion, provides a viral core protein for use in the assembling a modified HBV viral capsid.

In some embodiments, a modified tail portion, e.g., a modified C-terminal tail portion, may include a modification that includes one or more poly-lysines. For example, the modified tail portion may include about 4 to about 30 lysines, or about 5 to about 20 lysines, e.g., about 7, 8, 9, or 10 lysines.

In certain embodiments, the modified tail portion may include one or more lysine domains. For example, each poly-lysine domain may comprise about one to about thirty lysine residues. In some embodiments the poly-lysine domain may comprise about 5 lysine residues to about 20 lysine residues. When more than one polylysine domain is present, the poly-lysine domains can be separated by about 1 to about 20 amino acid residues. In some embodiments, where more than one poly-lysine domain is present each poly-lysine domain may comprise about 4 lysine residues to about 20 lysine residues (or any specific amino acid length disposed with the range). In some embodiments, at least four or at least five consecutive lysine residues are included in a modified C-terminal tail.

Poly-lysines and poly-lysine domains and/or a poly-histidine tag may form part of a modified C-terminal tails separately or in combination. A poly-histidine tag may, in some embodiments, facilitate purification of the proteins.

Exemplary C-terminal tail portions include those having, e.g., 5 lysines (K5), 7 lysines (K7), 9 lysines (K9), 10 lysines (K10), 11 lysines (K11), 13 lysines (K13), 20 lysines (K20). Other exemplary C-terminal tail portions include those with a poly-lysine region with nine lysines alternating with a poly-alanine region with nine alanines (KA9), a poly-lysine region with nine lysines alternating with a poly-glycine region with nine glycines (KG9) and a poly-lysine region with nine lysines interrupted by a sequence of at least four amino acids between the fourth and fifth lysines (K4-5). In some embodiments, an about four amino acid stretch between the fourth and fifth lysines of the K4-5 tail may be amino acids Ser-Gln-Ser-Pro (SEQ ID NO: 57). For example, a modified tail portion may be represented by:

```
                                      (SEQ ID NO: 58)
KLAAA[KKKKK]$_i$LE[H]$_j$
``` wherein i is an integer from 4 to 21, and j is an integer from 0 to 10. For example, i may be 5, 6, 7, 8, 9, 10, 11, 12, 13, 14, 15, 16, 17, 18, 19 or 20; j may be 0, 1, 2, 3, 4, 5 or more.

In various embodiments, a modified tail portion may be formed from alternating lysines. For example, in one embodiment, a modified tail portion can be represented by:

```
                                      (SEQ ID NO: 59)
DKLAA[AK]$_p$LE[H]$_j$
``` wherein p is an integer from 5 to 12, and j is an integer from 0 to 10. For example, p may be 5, 6, 7, 8, 9, 10, 11, or 12; j may be 0, 1, 2, 3, 4, 5 or more.

Exemplary CP149 structural core portions of a HBV core protein with a modified tail portions include:

CP149 with a E77C mutation, a K5 tail portion and a histidine tag in a SEQ ID NO:2 variant

```
                                      (SEQ ID NO: 60)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

LEHHHHHH;
```

CP149 with a E77C mutation, a K7 tail portion in a SEQ ID NO: 2 variant

```
                                        (SEQ ID NO: 61)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKLEHHHHHH;
```

CP149 with E77C mutation, a K9 tail portion and a histidine tag in a SEQ ID NO: 2 variant

```
                                        (SEQ ID NO: 62)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKLEHHHH HH;
```

CP149 with a E77C mutation, a K10 tail portion and a histidine tag in a SEQ ID NO: 2 variant

```
                                        (SEQ ID NO: 63)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKKLEHHH HHH;
```

CP149 with a E77C mutation, a K11 tail portion and a histidine tag in a SEQ ID NO: 2 variant

```
                                        (SEQ ID NO: 64)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKKKLEHH HHHH;
```

CP149 with a E77C mutation, a K13 tail portion and a histidine tag in a SEQ ID NO: 2 variant

```
                                        (SEQ ID NO: 65)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKKKKKLE HHHHHH;
```

CP149 with E77C mutation, a K20 tail portion and a histidine tag in a SEQ ID NO: 2 variant

```
                                        (SEQ ID NO: 66)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKKKKKKK KKKKKLEHHH HHH;
```

CP149 with a E77C mutation, a K4-5 tail portion and a histidine tag in a SEQ ID NO: 2 variant

```
                                        (SEQ ID NO: 67)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKS

QSPKKKKKLE HHHHHH;
```

CP149 with a E77C mutation, a KA9 tail portion and a histidine tag in a SEQ ID NO: 2 variant

```
                                        (SEQ ID NO: 68)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKAKAK

AKAKAKAKAK AKLEHHHHHH;
and
```

CP149 with a E77C mutation, a KG9 tail portion and a histidine tag in a SEQ ID NO: 2 variant

```
                                        (SEQ ID NO: 69)
MDIDPYKEFG ATVELLSFLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKGKGK

GKGKGKGKGK GKLEHHHHHH.
```

Exemplary CP149 structural core portions of a HBV core protein with a capsid assembly mutations (e.g., stabilizing and destabilizing mutations) and/or mutations for chemical attachment sites and a modified tail portion include:

CP149 with E77C and F18H mutations, a K9 tail potion, and a histidine tag in a SEQ ID NO: 2 variant

```
                                        (SEQ ID NO: 70)
MDIDPYKEFG ATVELLSHLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVD KLAAAKKKKK

KKKKLEHHHH HH;
```

CP149 with E77C and Y132A mutations, a K9 tail potion, and a histidine tag in a SEQ ID NO: 2 variant (SEQ ID NO: 71)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
SFGVWIRTPP AARPPNAPIL STLPETTVVD KLAAAKKKKK
KKKKLEHHHH HH;

CP149 with E77C and Y132V mutations, a K9 tail potion, and a histidine tag in a SEQ ID NO: 2 variant (SEQ ID NO: 72)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
SFGVWIRTPP AVRPPNAPIL STLPETTVVD KLAAAKKKKK
KKKKLEHHHH HH;

CP149 with E77C and Y132I mutations, a K9 tail potion, and a histidine tag in a SEQ ID NO: 2 variant (SEQ ID NO: 136)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
SFGVWIRTPP AIRPPNAPIL STLPETTVVD KLAAAKKKKK
KKKKLEHHHH HH;

CP149 with E77C and Y132F mutations, a K9 tail potion, and a histidine tag in a SEQ ID NO: 2 variant (SEQ ID NO: 137)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
SFGVWIRTPP AFRPPNAPIL STLPETTVVD KLAAAKKKKK
KKKKLEHHHH HH;

CP149 with E77C and I139A mutations, a K9 tail potion, and a histidine tag in a SEQ ID NO: 2 variant (SEQ ID NO: 73)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
SFGVWIRTPP AYRPPNAPAL STLPETTVVD KLAAAKKKKK
KKKKLEHHHH HH;

CP149 with E77C and C48A mutations, a K9 tail potion, and a histidine tag in a SEQ ID NO: 2 variant (SEQ ID NO: 74)
MDIDPYKEFG ATVELLSFLP SDFFPSVRDL LDTASALYRE
ALESPEHASP HHTALRQAIL CWGELMTLAT WVGNNLCDPA
SRDLVVNYVN TNMGLKIRQL LWFHISCLTF GRETVLEYLV
SFGVWIRTPP AYRPPNAPIL STLPETTVVD KLAAAKKKKK
KKKKLEHHHH HH;

CP149 with E77C, C48A, C61A and C107A mutations, a K9 tail potion, and a histidine tag in a SEQ ID NO: 2 variant (SEQ ID NO: 75)
MDIDPYKEFG ATVELLSFLP SDFFPSVRDL LDTASALYRE
ALESPEHASP HHTALRQAIL AWGELMTLAT WVGNNLCDPA
SRDLVVNYVN TNMGLKIRQL LWFHISALTF GRETVLEYLV
SFGVWIRTPP AYRPPNAPIL STLPETTVVD KLAAAKKKKK
KKKKLEHHHH HH;

CP149 with E77C and S121C mutations, a K9 tail potion, and a histidine tag in a SEQ ID NO: 2 variant (SEQ ID NO: 76)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
CFGVWIRTPP AYRPPNAPIL STLPETTVVD KLAAAKKKKK
KKKKLEHHHH HH;

CP149 with E77C, S121C and S141C mutations, a K9 tail potion, and a histidine tag in a SEQ ID NO: 2 variant (SEQ ID NO: 77)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
CFGVWIRTPP AYRPPNAPIL CTLPETTVVD KLAAAKKKKK
KKKLEHHHH HH;

CP149 with E77C, S121C, S141C and Y132F mutations, a K9 tail potion, and a histidine tag in a SEQ ID NO: 2 variant (SEQ ID NO: 78)
MDIDPYKEFG ATVELLSFLP SDFFPSVRDL LDTASALYRE
ALESPEHCSP HHTALRQAIL CWGELMTLAT WVGNNLCDPA
SRDLVVNYVN TNMGLKIRQL LWFHISCLTF GRETVLEYLV
CFGVWIRTPP AFRPPNAPIL CTLPETTVVD KLAAAKKKKK
KKKKLEHHHH HH;

CP149 with E77C, S121C, S141C and F18H mutations, a K9 tail potion, and a histidine tag in a SEQ ID NO: 2 variant

```
                                           (SEQ ID NO: 79)
MDIDPYKEFG ATVELLSHLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

CFGVWIRTPP AYRPPNAPIL CTLPETTVVD KLAAAKKKKK

KKKKLEHHHH HH;
```

CP149 with a D78E mutation, a K9 tail potion, and a histidine tag in a SEQ ID NO: 2 variant

```
                                           (SEQ ID NO: 80)
MDIDPYKEFG ATVELLSFLP SDFFPSVRDL LDTASALYRE

ALESPEHCSP HHTALRQAIL CWGELMTLAT WVGNNLEEPA

SRDLVVNYVN TNMGLKIRQL LWFHISCLTF GRETVLEYLV

SFGVWIRTPP AYRPPNAPIL STLPETTVVD KLAAAKKKKK

KKKKLEHHHH HH;
and
```

CP149 with a E77K mutation, a K9 tail potion, and a histidine tag in a SEQ ID NO: 2 variant

```
                                           (SEQ ID NO: 81)
MDIDPYKEFG ATVELLSFLP SDFFPSVRDL LDTASALYRE

ALESPEHCSP HHTALRQAIL CWGELMTLAT WVGNNLKDPA

SRDLVVNYVN TNMGLKIRQL LWFHISCLTF GRETVLEYLV

SFGVWIRTPP AYRPPNAPIL STLPETTVVD KLAAAKKKKK

KKKKLEHHHH HH.
```

It is contemplated herein that the poly-lysine tail for each of the foregoing embodiments could be of varying length (e.g., K5, K7, K10, K11, K13 or K20) or with alternating lysine sequences (e.g., KG and KA), may include a different linker, and may or may not have a histidine tag.

In other embodiments, a modified tail portion includes one or more poly-arginines. For example, the modified tail portion may include about 4 to about 30 arginines, or about 5 to about 20 arginines, e.g., about 7, 8, 9, or 10 arginines.

In some embodiments, the modified tail portion may include one or more arginine domains. When more than one poly-arginine domain is present, the poly-arginine domains can be separated by about 1 to about 20 amino acid residues. For example, each poly-arginine domain may comprise about one to about thirty arginine residues. In some embodiments, when more than one poly-arginine domain is present, the poly-arginine domain can comprise about 4 arginine residues to about 20 arginine residues (or any specific amino acid length disposed with the range). In some embodiments, a modified C-terminal tail includes at least four or at least five consecutive arginine residues. In another embodiment, a modified C terminal tail may have mixtures of arginines and lysines, e.g., one or more arginine domains and one or more lysine domains.

Poly-arginine domains and/or a poly-histidine tag can be added to the C-terminal tails separately or in combination. A poly-histidine tag may, in some embodiments, facilitate purification of the proteins. Exemplary C-terminal tail portions may include 5 arginines (R5), 7 arginines (R7), 9 arginines (R9), 11 arginines (R11), 13 arginines (R13), and 20 arginines (R20). Such modified tail portions that include poly-arginine domains may be represented by:

```
                                           SEQ ID NO: 82
DKLAAA[R]qLE[H]j
``` wherein q is an integer from 4 to 21 or more, and j is an integer from 0 to 10. For example, q may be 5, 6, 7, 8, 9, 10, 11, 12, 13, 14, 15, 16, 17, 18, 19 or 20; j may be 0, 1, 2, 3, 4, 5 or more.

It is contemplated herein that each of the foregoing embodiments describing modified HBV core proteins including truncation mutations, assembly mutations (e.g., stabilizing and/or destabilizing mutations), capsid attachment mutations, disassembly mutations, either singly or in combination can be modified with a poly-lysine tail or a polyarginine tail as described herein.

A linker segment may be optionally present between, e.g., a modified structural core portion and a modified tail portion, for example, between the amino acid residue 149 and another modified tail portion domain. In some embodiments, the linker segment is about 3 amino acids to about 15 amino acids in length (or any specific amino acid length disposed with the range) and can link, e.g., a modified tail portion including a poly-lysine domain and/or a poly-arginine domain to, e.g., amino acid 149 of the HBV core protein, for example, to provide flexibility to the C-terminal tail. For example, a poly-lysine domain may be followed by a polyhistidine tag and/or followed by an XhoI restriction site. In some embodiments, a polyhistidine tag can include at least six histidine residues added to the C-terminal tail. For example, such linker segments may be represented by:

```
                                           (SEQ ID NO: 83)
[SAG]s (SEQ ID NO: 84)
[TAG]r (SEQ ID NO: 85)
[GAG]t
``` wherein r, s and t are each independently, integers from 1 to 6 or more.

In certain embodiments, the modified HBV core protein may include a C-terminal cysteine residue. This cysteine may be included on the C-terminus of a natural or synthetic tail portion and therefore be encapsulated in the assembled cage. The C-terminal cysteine residue may be used for conjugation to a therapeutic agent or for stabilizing a mutation in a tail portion. An exemplary modified HBV core protein including a C-terminal cysteine residue based on a CP162 truncation mutant (based on a SEQ ID NO:2 variant) with E77C and F18H mutations is as follows:

```
                                           (SEQ ID NO: 86)
MDIDPYKEFG ATVELLSHLP SDFFPSVRDL LDTASALYRE

ALESPEHCSP HHTALRQAIL CWGELMTLAT WVGNNLCDPA

SRDLVVNYVN TNMGLKIRQL LWFHISCLTF GRETVLEYLV

SFGVWIRTPP AYRPPNAPIL STLPETTVVR RRGRSPRRRT

PSLEHHHHHH C
```

In each of the foregoing embodiments, it is appreciated that the same truncations and/or modifications can be engineered within HBV C-protein variant SEQ ID NO: 1.

It is also contemplated herein for each of the foregoing embodiments that a skilled person in the art recognizes that nucleic acid and amino acid sequences of the specific modified viral core proteins, e.g., about 75% to about 99% identical, about 80% to about 95% identical, about 85% to about 90% identical, or about 95% to about 99% identical, or any specific percent identity disposed within these ranges, to disclosed viral core proteins is capable of forming a capsid and within the scope of the present invention.

Expression of Viral Core Proteins

The disclosed viral core proteins can be expressed and purified using common molecular biology and biochemistry techniques. For example, recombinant expression vectors can be used which can be engineered to carry a viral core protein gene into a host cell to provide for expression of the viral core protein. Such vectors, for example, can be introduced into a host cell by transfection means including, but not limited to, heat shock, calcium phosphate, DEAE-dextran, electroporation or liposome-mediated transfer. Recombinant expression vectors include, but are not limited to, *E. coli* based expression vectors such as BL21 (DE3) pLysS, COS cell-based expression vectors such as CDM8 or pDC201, or CHO cell-based expression vectors such as pED vectors. A C-protein gene coding region, for example, can be linked to one of any number of promoters in an expression vector that can be activated in the chosen cell line. In an embodiment, a cassette (capsid gene and promoter) is carried by a vector that contains a selectable marker such that cells receiving the vector can be identified.

For example, promoters to express the capsid proteins within a cell line can be drawn from those that are functionally active within the host cell. Such promoters can include, but are not limited to, a T7 promoter, a CMV promoter, a SV40 early promoter, a herpes TK promoter, and others known in recombinant DNA technology. Inducible promoters can be used, and include promoters such as metallothionine promoter (MT), mouse mammary tumor virus promoter (MMTV), and others known to those skilled in the art. Exemplary selectable markers and their attendant selection agents can be drawn, for example, from the group including, but not limited to, ampicillin, kanamycin, aminoglycoside phosphotransferase/G418, hygromycin-B phosphotransferase/hygromycin-B, and amplifiable selection markers such as dihydrofolate reductase/methotrexate and others known to skilled practitioners.

A variety of eukaryotic, prokaryotic, insect, plant and yeast expression vector systems (e.g., vectors which contain the necessary elements for directing the replication, transcription, and translation of viral core protein coding sequences) can be utilized by those skilled in the art to express viral core protein coding sequences. These include but are not limited to microorganisms such as bacteria transformed with recombinant bacteriophage DNA, plasmid DNA or cosmid DNA expression vectors containing the capsid protein coding sequences; yeast transformed with recombinant yeast expression vectors containing the capsid protein coding sequences; insect cell systems infected with recombinant virus expression vectors (e.g., baculovirus) containing the capsid protein coding sequences; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the capsid protein coding sequences.

Therapeutic Agents

A therapeutic agent (e.g., a drug) may be encapsulated in the assembled viral capsid structure. The drug may be bound to the modified viral core protein by Coulombic forces or covalent bonding. Encapsulation of the drug may occur, in some instances, by conjugating the drug to a region of the viral core protein prior to self-assembly (i.e., when the viral core protein is in an open, locked state prior to assembly) and then triggering self-assembly such that the resultant viral capsid contains the drug. For example, in some embodiments, the drug may be bound to the amino acid tail portion of a modified HBV core protein. In some embodiments, the drug bound to the amino acid tail portion may be encapsulated following addition of the reducing agent.

In certain embodiments, a drug may be bound to an anionic or cationic polymer added to the assembly solution. Drugs bound to an anionic or cationic polymer maybe encapsulated into the assembled viral capsid based on association of an anionic or cationic polymer with a modified core protein or a modified tail portion.

In various embodiments, a solution of a drug and non-assembled viral core protein may be combined and self-assembly of the capsid triggered such that some of the drug is encapsulated and some of the drug is not encapsulated by the resultant viral capsids, i.e., the drug may be encapsulated in the capsid structure by diffusion after addition of the triggering agent (e.g., reducing agent). For example, the drug may be added to the solution prior to the addition of a reducing agent.

It is contemplated herein that therapeutic agents that may be encapsulated in the assembled viral capsid include nucleic acids, peptides, proteins, and/or small molecules. Non limiting examples of nucleic acid drugs include inhibitory nucleic acids such as a single-stranded or double-stranded RNA, siRNA (small interfering RNA), shRNA (short hairpin RNA), or antisense RNA, or a portion thereof, or an analog or mimetic thereof, that when administered to a mammal results in a decrease (e.g., by 10%, 25%, 50%, 75%, 90%, 95%, or 100%) in the expression of a target. Typically, an inhibitory nucleic acid comprises or corresponds to at least a portion of a target nucleic acid or gene, or an ortholog thereof, or comprises at least a portion of the complementary strand of a target nucleic acid or gene. An inhibitory nucleic acid typically has substantial or complete identity or homology (e.g., 60%, 70%, 80%, 85%, 90%, 95%, 99% or 100%) to the target nucleic acid. The term "target," as used herein, refers to a nucleic acid or variants thereof required for expression of a polypeptide that is the site or potential site of therapeutic intervention by a therapeutic agent; or a nonpeptide entity including a microorganism, virus, bacterium, or single cell parasite (wherein the entire genome of a virus may be regarded as a target); and/or a naturally occurring interfering RNA or microRNA or precursor thereof. For example, target may refer to the sequence of nucleotides corresponding to the portion of a gene's coding mRNA.

Non-limiting examples of drugs that may be encapsulated in the nanocage include bioactive agents such as cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antineoplastics, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, agents useful for erythropoiesis stimulation, antiulcer/antireflux agents, antinauseants/antiemetics and oil-soluble vitamins, or combinations thereof.

Non-limiting examples of chemotherapeutic agents include cyclophosphamide, doxorubicin, vincristine, prednisone, busulfan, cisplatin, methotrexate, daunorubicin, melphalan, cladribine, vinblastine, auristatin, bleomycin, calicheamycin, and chlorambucil.

Non-limiting examples of enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

Formulation and Delivery

It is contemplated herein that an assembled viral capsid may be formulated into a therapeutic composition using methods well-known in the art. This technology can be applied for delivery of drugs that can be sequestered inside the viral capsid. For non-limiting example, DNA and RNA (including siRNA) can be sequestered inside the capsid and then released at the desired time either free or associated with the appropriate nuclear localization molecules. Applications include cancer therapy, controlled drug release in pain control, marker delivery and anti-inflammatory delivery as well as in vitro gene delivery to cell cultures, and signal or drug delivery to in vitro engineered tissues.

Viral capsids may be formulated for delivery including with a pharmaceutically acceptable carrier, or compound. As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, nasal, optical, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, other fluids configured to preserve the integrity of the viral capsid, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols such as mannitol, sorbitol, and sodium chloride sometimes are included in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means, including nasal and optical. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Delivery vehicles can also be prepared in the form of suppositories (e.g., with conventional suppository bases such as cocoa butter and other glycerides) or retention enemas for rectal delivery.

In some embodiments oral or parenteral compositions are formulated in a dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD.sub.50 (the dose lethal to 50% of the population) and the ED.sub.50 (the dose therapeutically effective in 50% of the population). The dose ratio between toxic and therapeutic effects is the therapeutic index and it can be expressed as the ratio LD.sub.50/ED.sub.50. Molecules which exhibit high therapeutic indices often are utilized. While molecules that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such molecules often lies within a range of circulating concentrations that include the ED.sub.50 with little or no toxicity. The dosage may vary within this range depending upon the dosage form employed and the route of administration utilized. For any molecules used in the methods described herein, the therapeutically effective dose can be estimated initially from cell culture assays. A dose may be formulated in animal models to achieve a circulating plasma concentration range that includes the IC.sub.50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Another example of effective dose determination for an individual is the ability to directly assay levels of "free" and "bound" compound in the serum of the test subject. Such assays may utilize antibody mimics and/or biosensors.

Antibody conjugates can be used for modifying a given biological response, the drug moiety delivered via the viral capsid is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a polypeptide such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Alternatively, an antibody can be conjugated to a second antibody to form an antibody heteroconjugate.

For compounds, exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated, particularly when one delivers the molecule directly to the cell cytosol. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules can be inserted into viral capsids and used in gene therapy methods for treatment, including without limitation, cancer. Gene therapy capsids can be delivered to a subject by, for example, intravenous injection and local administration. Pharmaceutical preparations of gene therapy capsids can include a gene therapy capsid in an acceptable diluent, or can comprise a slow release matrix in which the gene delivery vehicle is imbedded.

Pharmaceutical compositions can be included in a container, pack, or dispenser together with instructions for administration. Pharmaceutical compositions of active ingredients can be administered by any of the paths described herein for therapeutic and prophylactic methods for treatment. With regard to both prophylactic and therapeutic methods of treatment, such treatments may be specifically tailored or modified, based on knowledge obtained from pharmacogenomic analyses described herein. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes, oligonucleotides, and analgesics.

Successful treatment of disorders including cancer can be brought about by techniques that serve to inhibit the expression or activity of target gene products. Inhibitory molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')2 and FAb expression library fragments, scFV molecules, and epitope-binding fragments thereof).

Further, antisense and ribozyme molecules that inhibit expression of the target gene can also be used to reduce the level of target gene expression, thus effectively reducing the level of target gene activity. Still further, triple helix molecules can be utilized in reducing the level of target gene activity.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via the viral capsid gene therapy method herein.

Another method by which nucleic acid molecules may be utilized in treating or preventing a disease characterized by aberrant gene expression is through the use of aptamer molecules specific for the defective polypeptide. Aptamers are nucleic acid molecules having a tertiary structure that permits them to specifically bind to polypeptide ligands. Since nucleic acid molecules may in many cases be more conveniently introduced into target cells than therapeutic polypeptide molecules may be, aptamers offer a method by which abnormal polypeptide activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of cancer and related disorders.

In instances where the target antigen is intracellular and whole antibodies are used, viral capsids can be used to deliver the antibody or a fragment of the Fab region that binds to the target antigen into cells. Where fragments of the antibody are used, the smallest inhibitory fragment that binds to the target antigen often is utilized. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population.

EXAMPLES

The examples which follow are intended in no way to limit the scope of the invention, but are provided to illustrate different features of the present invention, including preparation and use of the therapeutics contemplated herein. Many other embodiments of this invention will be apparent to one skilled in the art.

Example 1

Cloning of HBV E77C his-Tagged Core Protein

A. HBV E77C His-Tagged Core Protein

E77C His-tagged HBV core protein was cloned into the NdeI/XhoI restriction sites of vector pET21b (Novagen). This plasmid was transformed into *E. coli* BL21 (DE3) PlysS cells (Stratagene) for protein expression. The nucleic acid and corresponding amino acid sequences of the E77C His-tagged Core protein are depicted below:

```
                                           (SEQ ID NO: 87)
ATG GAT ATC GAT CCG TAT AAA GAA TTT GGC GCC ACC

GTG GAA CTG CTG AGC TTT CTG CCG AGC GAT TTC TTT

CCG AGC GTG CGT GAT CTG CTG GAT ACC GCG AGC GCG

CTG TAT CGC GAA GCG CTG GAA AGC CCG GAA CAT TGT

AGC CCG CAC CAT ACC GCC CTG CGT CAG GCG ATT CTG

TGC TGG GGT GAA CTG ATG ACC CTG GCG ACC TGG GTT

GGC AAC AAC CTG TGT GAT CCG GCG AGC CGC GAT CTG
```

```
-continued
GTT GTG AAC TAT GTG AAT ACC AAC ATG GGC CTG AAA

ATT CGT CAG CTG CTG TGG TTT CAT ATC AGC TGC CTG

ACC TTT GGC CGC GAA ACC GTG CTG GAA TAT CTG GTG

AGC TTT GGC GTT TGG ATC CGT ACC CCG CCG GCG TAT

CGT CCG CCG AAT GCG CCG ATT CTG AGC ACC CTG CCG

GAA ACC ACC GTT GTG CGT CGC CGT GGT CGC AGC CCG

CGC CGT CGT ACC CCG AGC CCG CGT CGT CGT CGT AGC

CAG AGC CCG CGT CGT CGC CGC AGC CAG AGC CGC GAA

AGC CAG CTC GAG CAC CAC CAC CAC CAC CAC
```

```
                                           (SEQ ID NO: 88)
MDIDPYKEFGATVELLSFLPSDFFPSVRDLLDTASALYREALESPEHCSP

HHTALRQAILCWGELMTLATWVGNNLCDPASRDLVVNYVNTNMGLKIRQL

LWFHISCLTFGRETVLEYLVSFGVWIRTPPAYRPPNAPILSTLPETTVVR

RRGRSPRRRTPSPRRRRSQSPRRRRSQSRESQLEHHHHHH
```

B. Cloning and Expression of Poly-Lysine Tail Mutants

DNA fragments containing the genes for K5, K7, K9, K10, K11, K13, K20, KA9, KG9 and K4-5 core protein mutants described previously were synthesized via PCR using the Cassette1 template and the primer sequences described in Table 1. Each PCR reaction was composed of 12.5 μl of 5×GC polymerase buffer (Finnzyme), 1.25 μl of a 10 mM dNTP mixture, 1.5 μl of 5 μM forward primer, 1.5 μl of 5 μM reverse primer, 0.6 μl of Stratagene mini-prepped template, 0.8 μl of 2 unit/μl Phusion Hot Start polymerase (Finnzyme), and 44.25 μl of water. The PCR reaction consisted of a one-time incubation at 98° C. for 1 minute, followed by incubation at 98° C. for 25 seconds, incubation at 70° C. for 30 seconds, and incubation at 72° C. for 1 minute and 10 seconds. These last three steps were repeated 24 times followed by a final incubation at 72° C. for 7 minutes.

The Cassette 1 template consists of the following nucleic acid sequence inserted into the NdeI/XhoI restriction sites of vector pET22b:

```
                                           (SEQ ID NO: 89)
ATGGATATCGATCCGTATAAAGAATTTGGCGCCACCGTGGAACTGCTGAG

CTTTCTGCCGAGCGATTTCTTTCCGAGCGTGCGTGATCTGCTGGATACCG

CGAGCGCGCTGTATCGCGAAGCGCTGGAAAGCCCGGAACATTGTAGCCCG

CACCATACCGCCCTGCGTCAGGCGATTCTGTGCTGGGGTGAACTGATGAC

CCTGGCGACCTGGGTTGGCAACAACCTGTGCGATCCGGCGAGCCGCGATC

TGGTTGTGAACTATGTGAATACCAACATGGGCCTGAAAATTCGTCTGCTG

CTGTGGTTTCATATCAGCTGCCTGACCTTTGGCCGCGAAACCGTGCTGGA

ATATCTGGTGAGCTTTGGCGTTTGGATCCGTACCCCGCCGGCGTATCGTC

CGCCGAATGCGCCGATTCTGAGCACCCTGCCGGAAACCACCGTTGTCGAC

AAGCTTGCGGCCGCACTCGAGCACCACCACCACCACCACTGA
```

TABLE 1

| Tail Mutant | Forward Primer (5' → 3') | Reverse Primer (5' → 3') |
|---|---|---|
| K5 | CGACTCACTATAGGGGAATTGTGAGCGG (SEQ ID NO: 90) | GGCCTCGAGCTTCTTTTTCTTCTTTGCGGCCGCAAGCTTGTCGAC (SEQ ID NO: 91) |
| K7 | CGACTCACTATAGGGGAATTGTGAGCGG (SEQ ID NO: 90) | GGCCTCGAGCTTCTTCTTTTTCTTCTTCTTTGCGGCCGCAAGCTTGTCGAC (SEQ ID NO: 92) |
| K9 | CGACTCACTATAGGGGAATTGTGAGCGG (SEQ ID NO: 90) | GGCCTCGAGCTTCTTCTTTTTCTTCTTCTTTTTCTTTGCGGCCGCAAGCTTGTCGAC (SEQ ID NO: 93) |
| K10 | CGACTCACTATAGGGGAATTGTGAGCGG (SEQ ID NO: 90) | GGCCTCGAGTTTCTTCTTCTTCTTCTTCTTTTTTCTTTGCGGCCGCAAGCTTGTCGAC (SEQ ID NO: 94) |
| K11 | CGACTCACTATAGGGGAATTGTGAGCGG (SEQ ID NO: 90) | GGCCTCGAGCTTCTTCTTTTTCTTCTTCTTTTTCTTCTTCTTTGCGGCCGCAAGCTTGTCGAC (SEQ ID NO: 95) |
| K13 | CGACTCACTATAGGGGAATTGTGAGCGG (SEQ ID NO: 90) | GGCCTCGAGCTTCTTCTTTTTCTTCTTCTTTTTCTTCTTCTTCTTTTTCTTGCGGCCGCAAGCTTGTCGAC (SEQ ID NO: 96) |
| K20 | CGACTCACTATAGGGGAATTGTGAGCGG (SEQ ID NO: 90) | GGCCTCGAGCTTTTTCTTCTTCTTCTTCTTCTTCTTTTTCTTCTTCTTCTTCTTCTTCTTTTTCTTTGCGGCCGCAAGCTTGTCGAC (SEQ ID NO: 97) |
| KA9 | CGACTCACTATAGGGGAATTGTGAGCGG (SEQ ID NO: 90) | GGCCTCGAGCTTCGCCTTAGCCTTCGCCTTAGCCTTTGCCTTCGCCTTAGCCTTTGCCTTTGCGGCCGCAAGCTTGTCGAC (SEQ ID NO: 98) |
| KG9 | CGACTCACTATAGGGGAATTGTGAGCGG (SEQ ID NO: 90) | GGC CTC GAG CTT ACC CTT GCC CTT GCC CTT ACC CTT GCC CTT ACC CTT ACC CTT GCC CTT ACC CTT TGC GGC CGC AAG CTT GTC GAC (SEQ ID NO: 99) |
| K4-5 | CGACTCACTATAGGGGAATTGTGAGCGG (SEQ ID NO: 90) | GGCCTCGAGTTTCTTCTTCTTCTTCGGGCTCTGGCTCTTCTTTTTCTTTGCGGCCGCAAGCTTGTCGAC (SEQ ID NO: 100) |
| CP155 | CGACTCACTATAGGGGAATTGTGAGCGG (SEQ ID NO: 90) | ATTCTCGAGGCTGCGACCACGGCGACGCAC (SEQ ID NO: 101) |
| CP162 | CGACTCACTATAGGGGAATTGTGAGCGG (SEQ ID NO: 90) | ATTCTCGAGGCTCGGGGTACGACGGCGCGG (SEQ ID NO: 102) |
| CP170 | CGACTCACTATAGGGGAATTGTGAGCGG (SEQ ID NO: 90) | ATTCTCGAGGCTCTGGCTACGACGACGACGCGGGCTCGGGT (SEQ ID NO: 103) |
| Linker 1 | CGACTCACTATAGGGGAATTGTGAGCGG (SEQ ID NO: 90) | GGCCTCGAGCTTCTTCTTTTTCTTCTTCTTTTTCTTGCCGGCGCTGCCCGCGCTGACAACGGTGGTTTCCGGCAG (SEQ ID NO: 104) |
| Linker 2 | CGACTCACTATAGGGGAATTGTGAGCGG (SEQ ID NO: 90) | GGCCTCGAGCTTCTTCTTTTTCTTCTTCTTTTTCTTGCCGGCGGTGCCCGCGGTGACAACGGTGGTTTCCGGCAG (SEQ ID NO: 105) |

TABLE 1-continued

| Tail Mutant | Forward Primer (5' → 3') | Reverse Primer (5' → 3') |
|---|---|---|
| Linker 3 | CGACTCACTATAGGGGAATT GTGAGCGG (SEQ ID NO: 90) | GGCCTCGAGCTTCTTCTTTTTCTT CTTCTTTTTCTTGCCGGCGCCGCC CGCGCCGACAACGGTGGTTTCCG GCAG (SEQ ID NO: 106) |

The PCR products and a pET22b vector were both digested with restriction enzymes NdeI and XhoI at 37° C. for 2 hours. The digested products were run on an agarose gel and the bands were excised and purified via gel extraction (Stratagene). Ligation reactions were composed of 5 µl of digested and purified PCR product, 1 µl of digested and purified pET22b vector, 1 µl of T4 DNA ligase buffer (NEB), 1 µl of T4 DNA ligase (NEB), and 2 µl of water and were incubated at room temperature for 12 hours.

The ligation reactions were transformed into XLI Blue *E. coli* cells (Stratagene) and the resulting colonies were grown in IX LB broth. The plasmids were purified via miniprep (Stratagene). The purified plasmids were sequenced (see below) and transformed into *E. coli* BL21 (DE3) PlysS cells (Stratagene) for protein expression. This strategy can be used for proteins containing from 0 to 30 lysine residues.

C. Cloning of Modified Structural Core Mutants:

DNA fragments containing point mutations of the K9 construct were synthesized via PCR using the K9 template (or in the case of double or triple mutants, the appropriate single or double mutant K9 template) and the primer sequences described in Table 2. Each PCR reaction consisted of 5 µl of 10×Pfu Turbo polymerase buffer (Stratagene), 1 µl of a 10 mM dNTP mixture, 1.5 µl of 5 µM forward primer, 1.5 µl of 5 µM reverse primer, 1 µl of Stratagene mini-prepped template, 1 µl of 2.5 unit/µl Pfu Turbo polymerase (Stratagene), and 39 µl of water. The PCR reaction consisted of a one-time incubation at 98° C. for 1 minute, followed by incubation at 98° C. for 30 seconds, incubation at 64-72° C. (depending on primer Tm) for 1 minute, and incubation at 72° C. for 6 minutes. These last three steps were repeated 20 times.

The K9 template consists of the following nucleic acid sequence inserted into the NdeI/XhoI restriction sites of vector pET22b:

(SEQ ID NO: 107)
ATGGATATCGATCCGTATAAAGAATTTGGCGCCACCGTGGAACTGCTGAGCTTTCTGCCGAGCGATTTCTT

TCCGAGCGTGCGTGATCTGCTGGATACCGCGAGCGCGCTGTATCGCGAAGCGCTGGAAAGCCCGGAACATT

GTAGCCCGCACCATACCGCCCTGCGTCAGGCGATTCTGTGCTGGGGTGAACTGATGACCCTGGCGACCTGG

GTTGGCAACAACCTGTGCGATCCGGCGAGCCGCGATCTGGTTGTGAACTATGTGAATACCAACATGGGCCT

GAAAATTCGTCAGCTGCTGTGGTTTCATATCAGCTGCCTGACCTTTGGCCGCGAAACCGTGCTGGAATATC

TGGTGAGCTTTGGCGTTTGGATCCGTACCCCGCCGGCGTATCGTCCGCCGAATGCGCCGATTCTGAGCACC

CTGCCGGAAACCACCGTTGTCGACAAGCTTGCGGCCGCAAAGAAAAAGAAGAAGAAAAAGAAGAAGCTCGA

GCACCACCACCACCACCAC

TABLE 2

| Point Mutant | Forward Primer (5'→3') | Reverse Primer (5'→3') |
|---|---|---|
| F18H | AACTGCTGAGCCATCTGCCGAGCGATTT (SEQ ID NO: 108) | AAATCGCTCGGCAGATGGCTCAGCAGTT (SEQ ID NO: 109) |
| Y132A | TACCCCGCCGGCGGCTCGTCCGCCGAAT (SEQ ID NO: 110) | ATTCGGCGGACGAGCCGCCGGCGGGGTA (SEQ ID NO: 111) |
| Y132V | TACCCCGCCGGCGGTTCGTCCGCCGAAT (SEQ ID NO: 112) | ATTCGGCGGACGAACCGCCGGCGGGGTA (SEQ ID NO: 113) |
| Y132I | TACCCCGCCGGCGATTCGTCCGCCGAAT (SEQ ID NO: 114) | ATTCGGCGGACGAATCGCCGGCGGGGTA (SEQ ID NO: 115) |
| Y132F | TACCCCGCCGGCGTTTCGTCCGCCGAAT (SEQ ID NO: 116) | ATTCGGCGGACGAAACGCCGGCGGGGTA (SEQ ID NO: 117) |
| I139A | TCCGCCGAATGCGCCGGCTCTGAGCACCCT (SEQ ID NO: 118) | AGGGTGCTCAGAGCCGGCGCATTCGGCGGA (SEQ ID NO: 119) |
| S121C | TGGAATATCTGGTGTGCTTTGGCGTTT (SEQ ID NO: 120) | AAACGCCAAAGCACACCAGATATTCCA (SEQ ID NO: 121) |
| S141C | ATGCGCCGATTCTGTGCACCCTGCCGGAAA (SEQ ID NO: 122) | TTTCCGGCAGGGTGCACAGAATCGGCGCAT (SEQ ID NO: 123) |
| C48A | AGCCCGGAACATGCGAGCCCGCACCAT (SEQ ID NO: 124) | ATGGTGCGGGCTCGCATGTTCCGGGCT (SEQ ID NO: 125) |
| C61A | AGGCGATTCTGGCGTGGGGTGAACT (SEQ ID NO: 126) | AGTTCACCCCACGCCAGAATCGCCT (SEQ ID NO: 127) |
| C107A | TTTCATATCAGCGCGCTGACCTTTGGCCGCGA (SEQ ID NO: 128) | TCGCGGCCAAAGGTCAGCGCGCTGATATGAAA (SEQ ID NO: 129) |
| C77E D78S | TGGCAACAACCTGGAAAGCCCGGCGAGCCGCGA (SEQ ID NO: 130) | TCGCGGCTCGCCGGGCTTTCCAGGTTGTTGCCA (SEQ ID NO: 131) |
| C77E D78E | TTGGCAACAACCTGGAAGAACCGGCGAGCCGCGAT (SEQ ID NO: 132) | ATCGCGGCTCGCCGGTTCTTCCAGGTTGTTGCCAA (SEQ ID NO: 133) |

The PCR products were digested with the restriction enzyme DpnI at 37° C. for 1.5 hours to eliminate any un-mutated template. The digested products were run on a 1% agarose gel and the bands were excised and purified via gel extraction (Stratagene).

The PCR products were then transformed into *E. coli* BL21 (DE3) PlysS cells (Stratagene) and the resulting colonies were grown in 1×LB broth and the plasmid purified via miniprep (Stratagene). The purified plasmids were then sequenced to confirm the change in nucleic acid sequence. This strategy can be applied to single amino acid changes or the deletion or insertion of multiple amino acid residues such as the removal of a poly-histidine tag (primers shown in Table 3).

TABLE 3

| | Forward Primer (5'→3') | Reverse Primer (5'→3') |
|---|---|---|
| His Tag Removal | AAGAAAAAGAAGAAGTGAGATCCGGCT (SEQ ID NO: 134) | AGCAGCCGGATCTCACTTCTTCTTTTTCTT (SEQ ID NO: 135) |

Example 2

Expression of HBV Core Protein

Various wild type and modified core proteins described herein were expressed and purified according to Protocol 1 or Protocol 2 as follows:

Protocol 1: A pET-11a vector containing the full-length HBV C-protein gene was transformed into *E. coli* DE3 cells and grown at 37° C. in LB media that was fortified with 2-4% glucose, trace elements and 200 µg/mL of carbenicillin. Protein expression was induced by the addition of 2 mM IPTG (isopropyl-beta-D-thiogalactopyranoside). Cells were harvested by pelleting after three hours of induction. SDS-PAGE was used to assess expression of Cprotein.

Core protein was purified from *E. coli* by resuspending in a solution of 50 mM Tris-HCl, pH 7.4, 1 mM EDTA, 5 mM DTT, 1 mM AEBSF, 0.1 mg/mL DNaseI and 0.1 mg/mL RNase. Cells were then lysed by passage through a French pressure cell. The suspension was centrifuged at 26,000×G for one hour. The pellet was discarded and solid sucrose was added to the supernatant to a final concentration of 0.15 M and centrifuged at 100,000×G for one hour. The pellet was discarded and solid (NH4)2SO4 was then added to reach a final concentration of 40% saturation. The mixture was stirred for one hour and then centrifuged for one hour at 26,000×G. The pellet was resuspended in a solution of 100 mM Tris-HCl at pH 7.5, 100 mM NaCl, 50 mM sucrose and 2 mM DTT (Buffer A) and loaded onto a Sepharose CL-4B (Pharmacia Biotech, Piscataway, N.J.) column (5 cm diameter×95 cm) equilibrated with Buffer A. The column was eluted at 2 mL/minute. Using this purification scheme, HBV viral capsids were separated from large aggregates and from soluble proteins of lower molecular weight. The fractions were pooled according to chromatographic profile and SDS-PAGE analysis. The solution was concentrated by ultrafiltration using Diaflo YM 100 ultrafitration membrane (Amicon, Beverly, Mass.) to about 10 mg/mL. Concentrated C-protein was dialyzed against 50 mM Tris-HCl, pH 7.5 and 0.15 M sucrose. The solution was then adjusted to pH 9.5 by adding 10N NaOH and urea to reach a final concentration of 3.5 M. The solution was then filtered using a Millex-HA 0.45 µm pore size filter unit (Millipore, Bedford, Mass.) and applied to a column (6.0 cm diameter×60 cm) of Superdex 75 (Pharmacia Biotech, Piscataway, N.J.) equilibrated with a solution consisting of 100 mM sodium bicarbonate, pH 9.5, and 2 mM DTT. The column was eluted at 5 mL/minute. The fractions containing dimeric protein as assessed by SDS-PAGE were pooled. These procedures can be used for the expression and purification of all core protein mutants. Alternately, the expression of this protein can be done in yeast cells according to methods well known to persons skilled in the art.

Protocol 2: All protein constructs containing a C-terminal 6-histidine tag were purified as follows. The pET vector containing the gene for K9 protein was kept in BL21 (DE3) PlysS cells for expression. The starter culture was inoculated from a colony on a 1×Luria Broth (1×LB) agar plate or from a 10% glycerol stock, stored at −80° C. The 1×LB was autoclaved in a 2 L flask and cooled. 100 mg of ampicillin (Amp) was added to the 1×LB. A starter culture was inoculated and allowed to grow at 37° C. for up to 24 hours with shaking at 200 rpm.

Fifteen 2 L flasks with 0.8 L of 2× yeast-tryptone (2×YT) broth were autoclaved and 1 mL of 100 mg/mL Amp was added to each flask. 50 mL of starter culture was then added to each flask. The culture was incubated at 37° C., while shaking at 200 rpm until the optical density (OD) at 600 nm reached 0.4-0.6. This process took approximately 2 hours. When the OD reached 0.4-0.6, the culture was induced with 1 mL of 1 M IPTG. Shaking continued for 4 more hours until OD reached 2.0 or greater. The cells were harvested by centrifuging in 500 mL centrifuge bottles at 11,300×G for 8 minutes. The bacterial pellets were transferred into two 50 mL conical tubes. Each tube was labeled with date/construct/prep number and frozen at −20° C.

Two 50 ml tubes (approximately 20 mL each) of cell paste were thawed. The following steps were applied to each tube. 40 mL of resuspension buffer (5 M urea, 50 mM NaHCO3 (pH 9.5), 10 mM imidazole) was added into each tube. The cells were suspended by continuous pipetting and poured into a 400 mL beaker. More resuspension buffer was added until there is ~100 mL total cell resuspension in the beaker. The beaker containing resuspended cells were placed in an ice bath and sonicated for 5 minutes using a Branson probe sonifier (pulse mode at approximately 40% duty cycling and power setting of 5). The cell mixture was sonicated in several intervals and allowed to rest on ice if it appeared that the sample was heated to higher than room temperature. The cell lysate was diluted 2 fold to 200 mL total, and 200 µL of 100 mg/mL DNase was added to the suspension. This suspension was stirred on ice for 10 minutes. The sonication step was repeated for 5 more minutes while on ice. The lysate was transferred to six 50 mL plastic centrifuge tubes, and centrifuged at 32,000×g for 45 minutes. Supernatant was discarded.

For purification, a 50 mL Ni2+-NTA agarose (Qiagen) column was washed and equilibrated in the resuspension buffer. 12 L of cells was lysed for each run of the column. The centrifuged lysate from 12 L of cells was combined and diluted to 500 mL with resuspension buffer. The centrifuged cell lysate was loaded onto the column, and the protein solution was allowed to sink to the top of the nickel matrix. 50 mL of resuspension buffer was passed through the column. An optional salt wash can be performed by washing the column with 250 mL of NaCl wash buffer (5 M urea, 50 mM NaHCO3 (pH 9.5), 20 mM imidazole, 250 mM NaCl). This salt wash reduces the A260/A280 ratio of the final purified protein by a value of 0.1 A.U. The column was washed with 250 mL of wash buffer (5 M Urea, 50 mM NaHCO3 (pH 9.5), 20 mM imidazole). Subsequently, 200 mL of elution buffer (5 M Urea, 2 mM NaHCO3 (pH 9.5), 250 mM imidazole) was passed through the column. Fractions were collected at every 5 mL, and of these, which 5 to 8 fractions contained protein.

The presence and/or concentration of protein was detected by measuring the absorbance of the fractions. SDS polyacrylamide gel electrophoresis (SDS PAGE) analysis was performed on the proteins to determine purity. Fractions containing protein were pooled, and transferred to dialysis tubing. Dialysis was performed in 4 L of storage buffer (5 M Urea, 1 mM EDTA, 2 mM NaHCO3 (pH 9.5)) for at least 4 hours at 4° C. The protein was then concentrated in an Amicon stirred cell concentrator (Millipore) to a final protein concentration of up to 75 mg/ml. A 12 L cell growth yielded approximately 500 mg of pure protein. Pure dialyzed protein was stored at −80° C. for 6-8 months.

Example 3

Assembly and Purification of Modified HBV Core Proteins

This example describes general methods for forming assembling and purifying capsids generated from modified HBV core proteins. In protocol 1, modified HBV core proteins were self-assembled into capsid structures following addition of a reducing agent to a solution containing the modified HBV core protein and a denaturing agent with no dilution step to reduce the amount of denaturing agent in the solution. In protocol 2, modified HBV core proteins were self-assembled into capsid structures following addition of a reducing agent to a solution containing the modified HBV core protein and a denaturing agent with a dilution step to reduce the concentration of denaturing agent. In protocol 3, modified HBV core proteins were self-assembled into capsid structures following dilution of the denaturing agent in a solution containing the modified HBV core protein without the addition of a reducing agent.

Without wishing to be bound by theory, HBV core protein mutants that are capable of forming strong cages in the presence of reducing agent are assembled into capsids using protocol 1 whereas mutants that form weaker cages, e.g., because there is mutation at the dimer-dimer interface, are assembled into capsids using protocols 2 and 3.

filtered with a 0.2 micron polyethersulfone syringe filter (Nalgene 25 mm disc). Some assembled capsid structures were then subject to surface functionalization.

Protocol 1 was used to assemble capsid structures with modified HBV core proteins including: modified HBV core protein (CP183) with an E77C mutation; CP149 proteins (based on a SEQ ID NO: 2 variant) with an E77C mutation and a poly-lysine tail including a K5 (SEQ ID NO: 60), K7 (SEQ ID NO: 61), K9 (SEQ ID NO: 62), K10 (SEQ ID NO: 63), K11 (SEQ ID NO: 64), K13 (SEQ ID NO: 65), K20 (SEQ ID NO: 66), K4-5 (SEQ ID NO: 67), KA9 (SEQ ID NO: 68) or KG9 (SEQ ID NO: 69) tail; CP149 protein (based on a SEQ ID NO: 2 variant) with mutations at E77C, S121C and S141C with a K9 tail portion (SEQ ID NO: 77); CP149 protein (based on a SEQ ID NO: 2 variant) with mutations at E77C, C48A, C61A and C107A with a K9 tail portion (SEQ ID NO: 75); CP162 protein (based on SEQ ID NO: 2 variant) with mutations at E77C:

```
                                                              (SEQ ID NO: 138)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVR RRGRSPRRRT PSLEHHHHHH;
```

Protocol 1: Methods of Self-Assembly of Viral Capsids by Exposure to Reducing Agents CP162 protein (based on SEQ ID NO: 2 variant) with mutations at E77C and F122I1:

```
                                                              (SEQ ID NO: 139)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SHGVWIRTPP AYRPPNAPIL STLPETTVVR RRGRSPRRRT PSLEHHHHHH;
and
```

Modified HBV core protein stored in a protein storage buffer between 4M and 6M urea was thawed for 30 minutes at CP162 protein (based on SEQ ID NO: 2 variant) with mutations at E77C and E14I1:

```
                                                              (SEQ ID NO: 140)
MDIDPYKEFG ATVHLLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVR RRGRSPRRRT PSLEHHHHHH.
``` room temperature. SiRNA stored at −20 degrees C. was also thawed for 30 minutes. 32 mg of modified HBV core protein was measured and siRNA was added to the protein at a ratio of 0.1 siRNA per core protein monomer and allowed to bind for 60 minutes. Ten molar equivalents of 13-mercaptoethanol was added to the siRNA-protein solution and allowed to reduce for fifteen minutes and form capsid structures. An additional ten molar equivalents of 13-mercaptoethanol was added to the solution and allowed to equilibrate for at least twelve hours.

The solution containing assembled capsid structures was filtered with a 0.2 micron polyethersulfone syringe filter (Nalgene 25 mm disc). Assembled capsid structures were purified on an Akta Purification System using a stationary phase Sepharose CL-6B (16×300 mm) column with a mobile phase of DSB2 buffer (1M urea, 25 mM glycine, 20 mM NaCl, 1 mM EDTA, pH 9.5). Fractions were collected and pooled using elutions between 20-32 mL. Pooled fractions were Protocol 2: Methods of Self-Assembly of Viral Capsids by Exposure to Reducing Agents and Dilution of Denaturants Modified HBV core protein stored in a protein storage buffer between 4M and 6M urea was thawed for 30 minutes at room temperature. SiRNA stored at −20 degrees C. was also thawed for 30 minutes. 32 mg of modified HBV core protein was measured and siRNA was added to the protein at a ratio of 0.1 siRNA per protein monomer and allowed to bind for 60 minutes. Ten molar equivalents of 13-mercaptoethanol was added to the siRNA-protein solution and allowed to reduce for fifteen minutes and form capsid structures. One ml of DSB2 buffer (1M urea, 25 mM glycine, 20 mM NaCl, 1 mM EDTA, pH 9.5) was then added to the solution and allowed to equilibrate for fifteen minutes. One ml of 1×TAE buffer (40 mM TRIS acetate, 1 mM EDTA, pH 8.8) was added to the solution followed by a fifteen minute equilibration. One ml of 0.5×PBS pH 9.5 was added to the solution followed by a fifteen minute equilibration. The final concentration of urea was 1.25 M. An additional ten molar equivalents of 13-mercaptoethanol was added to the solution and allowed to equilibrate for at least twelve hours.

The solution containing assembled capsid structures was filtered with a 0.2 micron polyethersulfone syringe filter (Nalgene 25 mm disc). Assembled capsid structures were purified on an Akta Purification System using a stationary phase Sepharose CL-6B (16×300 mm) column with a mobile phase of DSB2 buffer. Fractions were collected and pooled using elutions between 20-32 mL. Pooled fractions were filtered with a 0.2 micron polyethersulfone syringe filter (Nalgene 25 mm disc). Some assembled capsid structures were then subject to surface functionalization.

Protocol 2 was used to assemble capsid structures with modified HBV core proteins including: CP149 protein (based on a SEQ ID NO:2 variant) with mutations at E77C and F18H with a K9 tail portion (SEQ ID NO: 70); CP149 protein (based on a SEQ ID NO:2 variant) with mutations at E77C and Y132F with a K9 tail portion (SEQ ID NO: 137); CP149 protein (based on a SEQ ID NO:2 variant) with mutations at E77C and Y132I with a K9 tail portion (SEQ ID NO: 136); CP149 protein (based on a SEQ ID NO:2 variant) with mutations at E77C and Y132V with a K9 tail portion (SEQ ID NO: 72); CP149 protein (based on a SEQ ID NO:2 variant) with mutations at E77C, F18H, S 121C and S 141C with a K9 tail portion (SEQ ID NO: 79).

Protocol 2 was also used to assemble the following HBV core proteins:

CP162 protein (based on a SEQ ID NO: 2 variant) with E77C and F18H mutations

```
                                                        (SEQ ID NO: 141)
MDIDPYKEFG ATVELLSHLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVR RRGRSPRRRT PSLEHHHHHH;
```

CP162 protein (based on a SEQ ID NO:2 variant) with E77C and Y132F mutations

```
                                                        (SEQ ID NO: 142)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AFRPPNAPIL STLPETTVVR RRGRSPRRRT PSLEHHHHHH;
```

CP162 protein (based on a SEQ ID NO:2 variant) with E77C and A137H mutations

```
                                                        (SEQ ID NO: 143)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNHPIL STLPETTVVR RRGRSPRRRT PSLEHHHHHH;
```

CP162 protein (based on a SEQ ID NO: 2 variant) with E77C and Y118H mutations

```
                                                        (SEQ ID NO: 144)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEHLV

SFGVWIRTPP AYRPPNAPIL STLPETTVVR RRGRSPRRRT PSLEHHHHHH;
```

CP162 protein (based on a SEQ ID NO: 2 variant) with E77C and L37H mutations (SEQ ID NO: 145)
MDIDPYKEFG ATVELLSFLP SDFFPSVRDL LDTASAHYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVR RRGRSPRRRT PSLEHHHHHH;

CP162 protein (based on a SEQ ID NO: 2 variant) with E77C, C171 and F1811 mutations (SEQ ID NO: 146)
MDIDPYKEFG ATVELLSHLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVR RRGRSPRRRT PSLEHHHHHH C;

and
CP162 protein (based on a SEQ ID NO: 2 variant) with E77C, C171 and A137H mutations (SEQ ID NO: 147)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNHPIL STLPETTVVR RRGRSPRRRT PSLEHHHHHH C.

Protocol 3: Methods of Self-Assembly of Viral Capsids by Dilution of Denaturants Modified HBV core protein stored in a protein storage buffer between 4M and 6M urea was thawed for 30 minutes at room temperature. SiRNA stored at −20 degrees C. was also thawed for 30 minutes. 32 mg of modified HBV core protein was measured and siRNA was added to the protein at a ratio of 0.1 siRNA per protein monomer and allowed to bind for 60 minutes. One ml of DSB2 buffer (1M urea, 25 mM glycine, 20 mM NaCl, 1 mM EDTA, pH 9.5) was added to the siRNA-protein solution and allowed to equilibrate for fifteen minutes and form capsid structures. The addition of one ml DSB2 buffer followed by a fifteen minute equilibration was repeated two more times, for a total of three cycles. The final concentration of urea was 1.25 M. The solution was allowed to equilibrate for at least twelve hours after the third cycle.

The solution containing assembled capsid structures was filtered with a 0.2 micron polyethersulfone syringe filter (Nalgene 25 mm disc). Assembled capsid structures were purified on an Akta Purification System using a stationary phase Sepharose CL-6B (16×300 mm) column with a mobile phase of DSB2 buffer. Fractions were collected and pooled using elutions between 20-32 mL. Pooled fractions were filtered with a 0.2 micron polyethersulfone syringe filter (Nalgene 25 mm disc). Some assembled capsid structures were then subject to surface functionalization.

Protocol 3 was used to assemble capsid structures with modified HBV core proteins including: CP149 protein (based on a SEQ ID NO: 2 variant) with a E77K mutation and a K9 tail (SEQ ID NO: 81).

Example 4

Dynamic Light Scattering Measurements to Monitor Viral Capsid Assembly

This example measures the radius of viral capsid structures assembled using protocols 1-3 described in Example 3 by Dynamic Light Scattering (DLS). DLS is a tool to examine the size characteristics of small (sub-micrometer) particles in solution.

Figure 2:
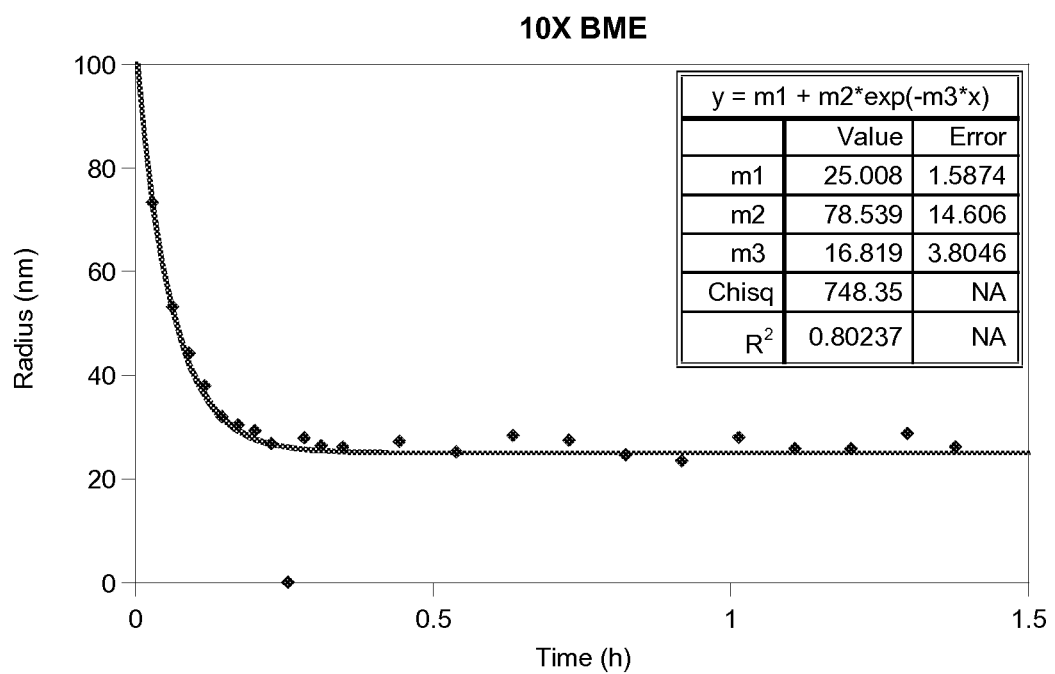
FIG. 2 is a dynamic light scattering (DLS) plot showing the formation of modified HBV viral capsids in the presence of 10× beta-mercaptoethanol (BME)

FIG. 2 shows a dynamic light scattering (DLS) plot of particle radius as a function of time following addition of 10 molar equivalents of BME to the protein (modified HBV core protein CP149 with a E77C mutation and a K9 tail (SEQ ID NO: 62)) and inhibitory dsRNA solution as described in Protocol 1 in Example 3. The data show that cage formation is dependent on the presence of BME, as indicated by the change in particle size.

Figure 3:
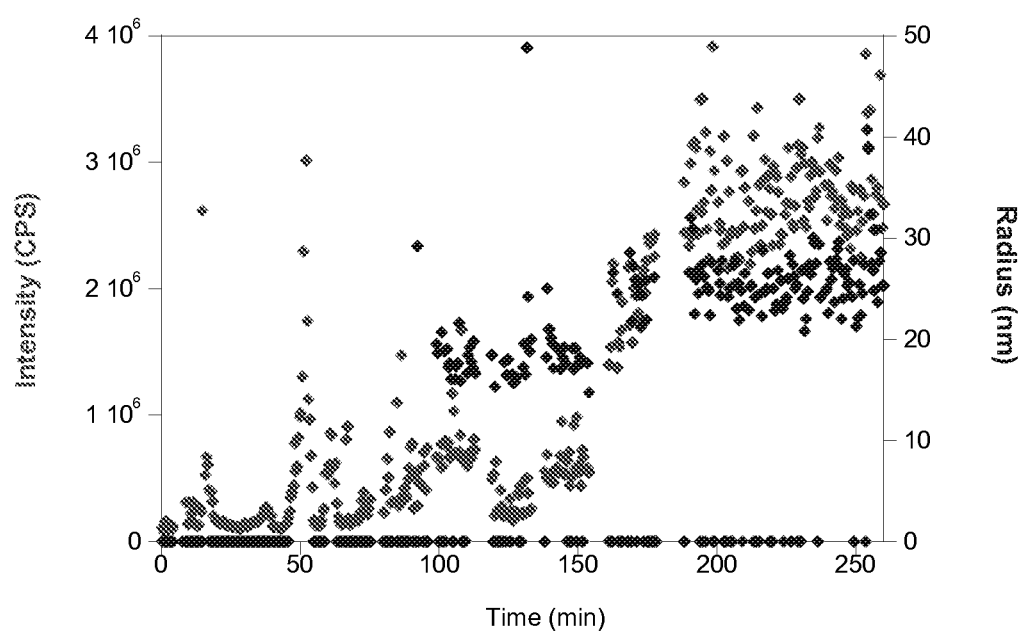
FIG. 3 is a DLS plot showing the formation of modified HBV viral capsids following the addition of BME.

FIG. 3 shows a DLS plot of particle radius (nm) (right vertical axis, darker data points) and signal intensity (CPS) (left vertical axis, lighter data points) as a function of time following the addition of BME to the protein (modified HBV core protein CP162 with a E77C mutation (SEQ ID NO: 138)) and inhibitory dsRNA (20 siRNA/cage) solution as described in Protocol 1 in Example 3. Capsid assembly was observed between 100-150 minutes as indicated by a shift in particle radius to approximately 15-20 nm.

Figure 4:
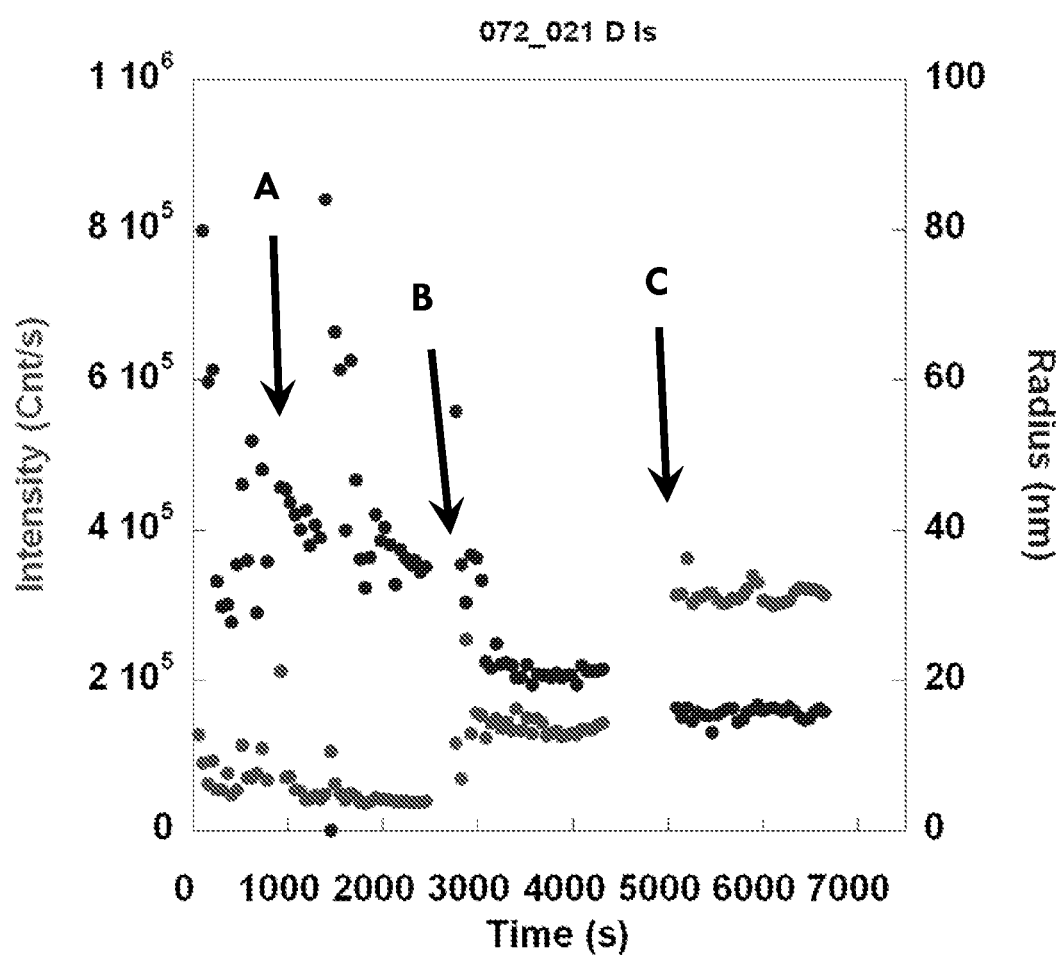
FIG. 4 is a DLS plot showing the formation of modified HBV viral capsids following the addition of BME.

FIG. 4 shows a DLS plot of particle radius (nm) (right vertical axis, darker data points) and signal intensity (CPS) (left vertical axis, lighter data points) as a function of time following the addition of 10 Molar equivalents of BME to the protein (modified HBV core protein CP149 with E77C, C48A, C61A, and C107A mutations (SEQ ID NO: 75)) and inhibitory dsRNA solution as described in Protocol 1 in Example 3. (A) The inhibitory dsRNA (0.1 equivalents) was added to the solution, which had a urea concentration of 2.5 M. (B) Capsid assembly was observed between 3000-4000 seconds following the addition of BME as indicated by the shift in particle radius to approximately 20 nm. (C) Lowering the urea concentration to 1.25 M with 0.5×PBS at pH 9.5 promoted the additional formation of capsids, but was not required to form capsids.

Figure 5:
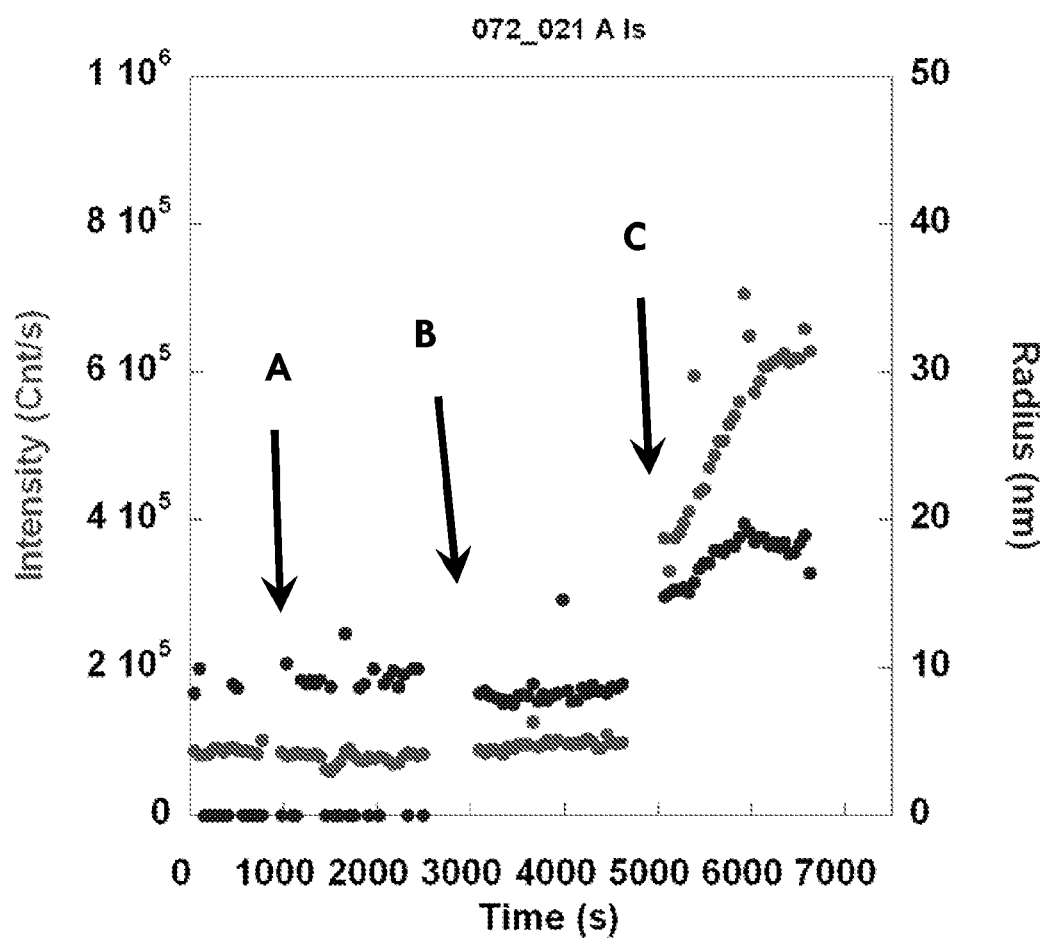
FIG. 5 is a DLS plots showing the formation of modified HBV viral capsids following the addition of BME and dilution of denaturant.

FIG. 5 shows a DLS plot of particle radius (nm) (right vertical axis, darker data points) and signal intensity (CPS) (left vertical axis, lighter data points) as a function of time following the addition of 10 Molar equivalents of BME to the protein (modified HBV core protein CP149 with E77C and F18H mutations with a K9 tail (SEQ ID NO: 70)) and inhibitory dsRNA solution as described in Protocol 2 in Example 3. (A) The inhibitory dsRNA (0.1 equivalents) was added to the solution, which had a urea concentration of 2.5 M. (B) 10 Molar equivalents of BME were added. (C) Capsid assembly was observed second following the dilution of urea to 1.25 M with 0.5×PBS pH 9.5 as indicated by the shift in particle radius to approximately 15-20 nm.

Figure 6:
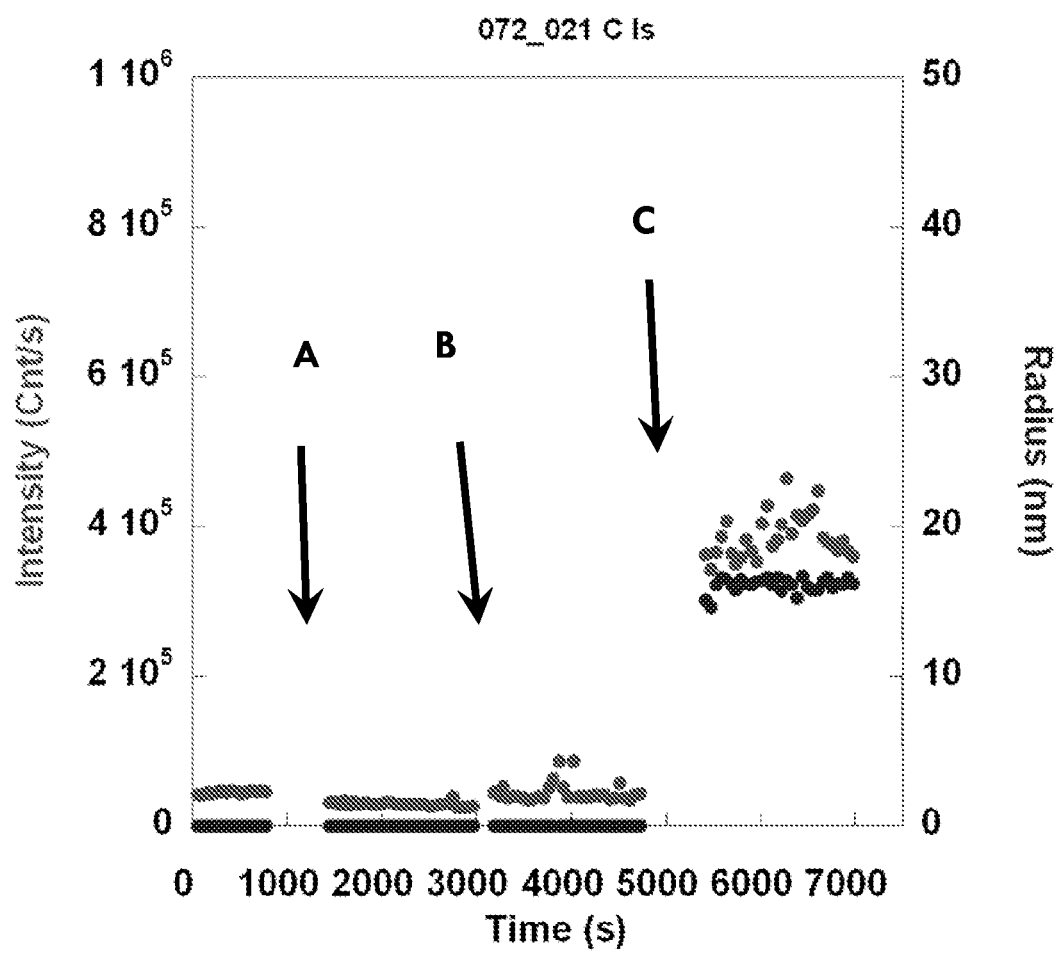
FIG. 6 is a DLS plots showing the formation of modified HBV viral capsids following the addition of BME and dilution of denaturant.

FIG. 6 shows a DLS plot of particle radius (nm) (right vertical axis, darker data points) and signal intensity (CPS) (left vertical axis, lighter data points) as a function of time following the addition of 10 Molar equivalents of BME to the protein (modified HBV core protein CP149 with E77C and Y132F mutations with a K9 tail (SEQ ID NO: 137)) and inhibitory dsRNA solution as described in Protocol 2 in Example 3. (A) The inhibitory dsRNA (0.1 equivalents) was added to the solution, which had a urea concentration of 2.5 M. (B) 10 Molar equivalents of BME were added. (C) Capsid assembly was observed following the dilution of urea to 1.25 M with 0.5×PBS pH 9.5 as indicated by the shift in particle radius to approximately 15-20 nm.

Figure 7:
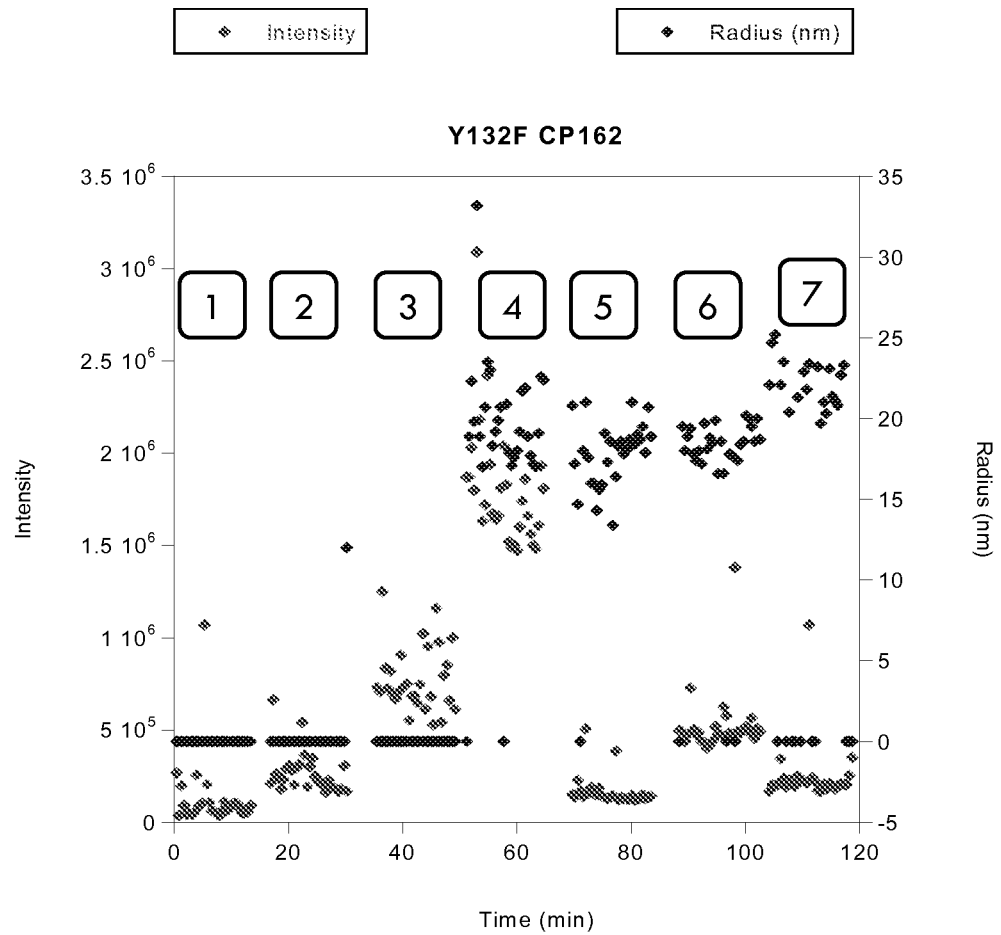
FIG. 7 is a DLS plots showing the formation of modified HBV viral capsids following the addition of BME and dilution of denaturant.

FIG. 7 shows a DLS plot of particle radius (nm) (right vertical axis, darker data points) and signal intensity (CPS) (left vertical axis, lighter data points) as a function of time following the addition of 10 Molar equivalents of BME to the protein (modified HBV core protein CP162 with E77C and Y132F mutations (SEQ ID NO: 142)) and inhibitory dsRNA solution as described in Protocol 2 in Example 3. The inhibitory dsRNA (0.1 equivalents) was added and the solution diluted to a urea concentration of 2.5 M (step 2). 10 Molar equivalents of BME was added (step 3). Capsid assembly was observed second following the dilution of urea to 1.25 M with 0.5×PBS pH 9.5 as indicated by the shift in particle radius to approximately 15-20 nm (steps 4-6).

Figure 8:
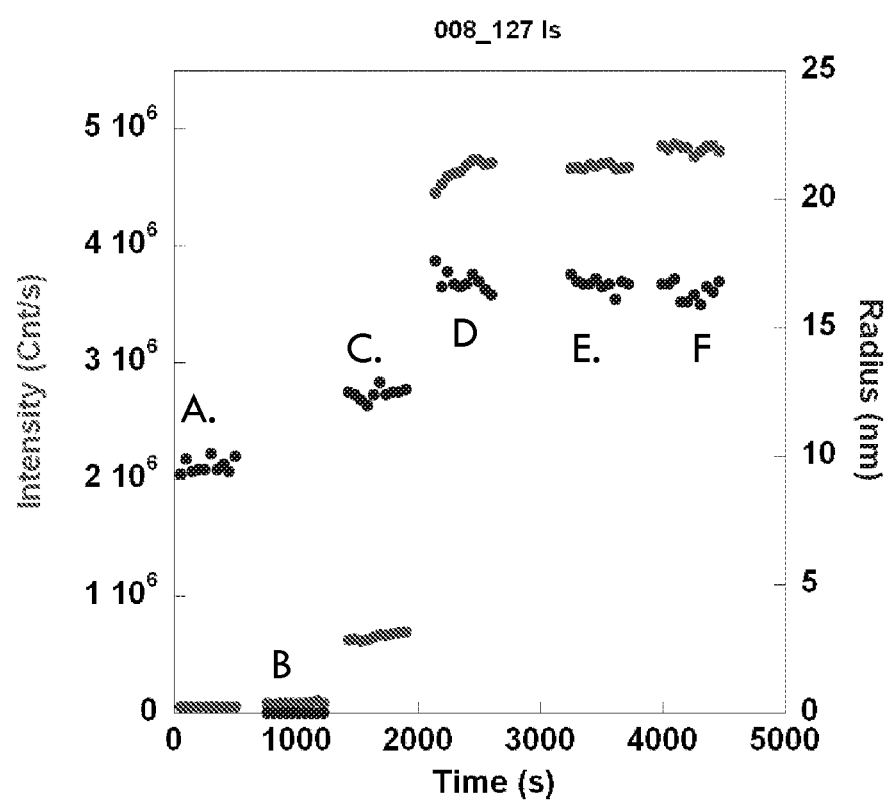
FIG. 8 is a DLS plot showing the formation of modified HBV viral capsids following the dilution of denaturant in the presence of a negative polymer.

FIG. 8 shows a DLS plot of particle radius (nm) (right vertical axis, darker data points) and signal intensity (CPS) (left vertical axis, lighter data points) as a function of time following addition of each cage-forming reaction component to the protein solution being monitored. Briefly, as described in Protocol 3 of Example 3, modified HBV core protein, E77K mutation with a K9 tail (SEQ ID NO: 81) (38.4 mg/mL stock), stored at −80 deg C. in protein storage buffer which contains 6M urea, was thawed for 30 minutes and 100 μL placed in a cuvvette (A). The following reaction components were sequentially added to the cuvette and both size and intensity were measured between each addition: 3.75 μL heparin (100 mg/mL stock) (B); 100 μL DSB2 buffer (1M urea, 25 mM glycine, 20 mM NaCl, 1 mM EDTA, pH 9.5) (C); 100 μL 0.5×PBS, pH 9.5 (D) and 100 μL 1×PBS, pH 7.4 (E). Particle radius measurements were consistent with the formation of HBV capsids. Well-formed cages were first detected after the addition of the first PBS containing system. These data suggest formation of these E77K/K9 nanocages is dependent upon the dilution of urea. As a control, after nanocages had formed, 1.5 μL of 1.42M (3ME was added to the reaction mix (F). Particle size did not change with the addition of the reducing agent nor did the intensity of the sample change, indicating the cage formation process is not under control of the redox state of the solution.

Figure 9:
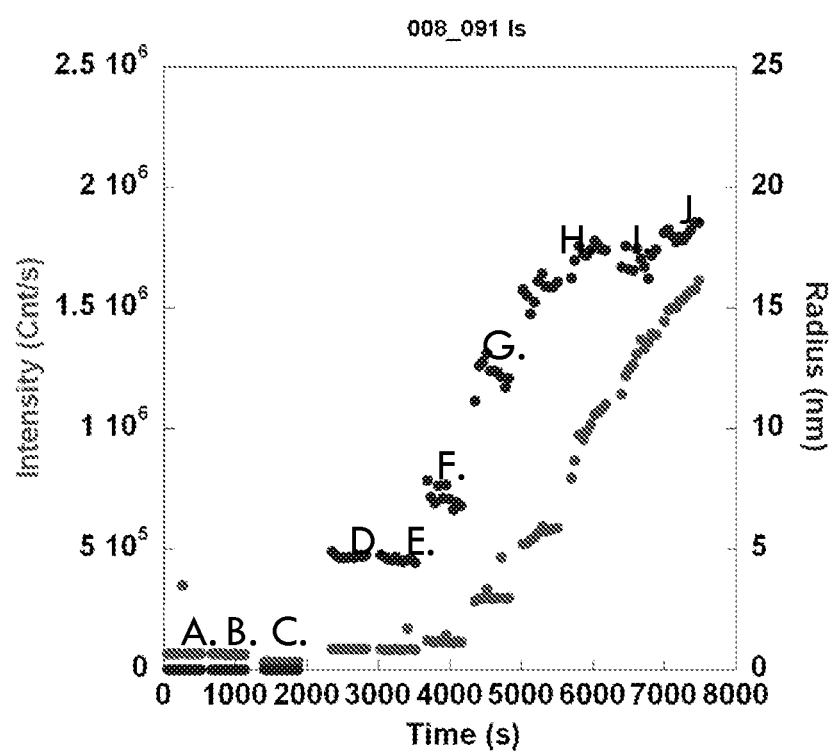
FIG. 9 is a DLS plot showing the formation of modified HBV viral capsids following the addition of BME in the absence of a negative polymer.

FIG. 9 shows a DLS plot of particle radius (right vertical axis, darker data points) and signal intensity (left vertical axis, lighter data points) as a function of time following addition of each cage-forming reaction component to the protein solution in the absence of a negatively charged polymer. Modified HBV core protein, CP149 with a E77C mutation was used in this experiment:

(SEQ ID NO: 148)
MDIDPYKEFG ATVELLSFLP SDFFPSVRDL LDTASALYRE ALESPEHCSP HHTALRQAIL

CWGELMTLAT WVGNNLCDPA SRDLVVNYVN TNMGLKIRQL LWFHISCLTF GRETVLEYLV

SFGVWIRTPP AYRPPNAPIL STLPETTVVE HHHHHH.

Briefly, modified HBV core protein, CP149 with a E77C mutation (38.4 mg/mL stock), stored at −80 deg C. in protein storage buffer which contains 6M urea, was thawed for 30 minutes and 100 μL placed in a cuvvette. The following reaction components were sequentially added to the cuvette and both size and intensity were measured between each addition: dH20 (to replace the volume of polymer) (B); 10 M equivalents of BME (C); 100 μL DSB2 buffer (1M urea, 25 mM glycine, 20 mM NaCl, 1 mM EDTA, pH 9.5) (D); 100μ 0.5×PBS, pH 9.5 (E); and 100 μL 0.5×PBS, pH 7.4 (100 μL was added 5 times after an equilibration step following each addition) (F-J). Particle radius measurements were consistent with the formation of HBV capsids. Well-formed cages were first detected after the addition of the third addition of PBS to the assembly reaction (see step H). These data suggest CP149 form cage in the absence of a negatively charge polymer.

Solutions of purified therapeutic particles were analyzed to validate that the predicted material was obtained. The data indicate that select fractions purified from a size exclusion column were monodispersed. Table 4 shows the data obtained for a modified HBV core during the assembly process (e.g., CP149 with a E77C mutation and a K9 tail, which was subsequently lipid coated after cage formation).

TABLE 4

| Assembly Method | Particle Size Radius (nm) | Particle Size St. Dev. (nm) | Polydispersity (percent) |
| --- | --- | --- | --- |
| Thaw out protein | Not detected | N/A | N/A |
| Dilute protein | Not detected | N/A | N/A |
| Add siRNA | 59.7 | 10.5 | 8.0 |
| Add reducing agent (e.g., BME) | 21.6 | 3.6 | 11.0 |
| Desalt capsid solution | 19.3 | 0.9 | 8.6 |
| Add PE-maleimide | 23.9 | 1.2 | 11.1 |
| Cap sulfhydryl with NEM | 23.9 | 1.7 | 13.3 |
| Coat with Lipid | 33.2 | 3.5 | 8.4 |
| Syringe Filter | 31.6 | 2.2 | 10.8 |

Example 5

Rate of Capsid Formation

This example measures the rate of capsid formation under various reducing conditions.

The rate of capsid formation can be controlled based on the amount of reducing agent added to the modified HBV protein solution. Modified HBV protein dimers are maintained in an open or locked state in the presence of a denaturing solution.

Figure 10:
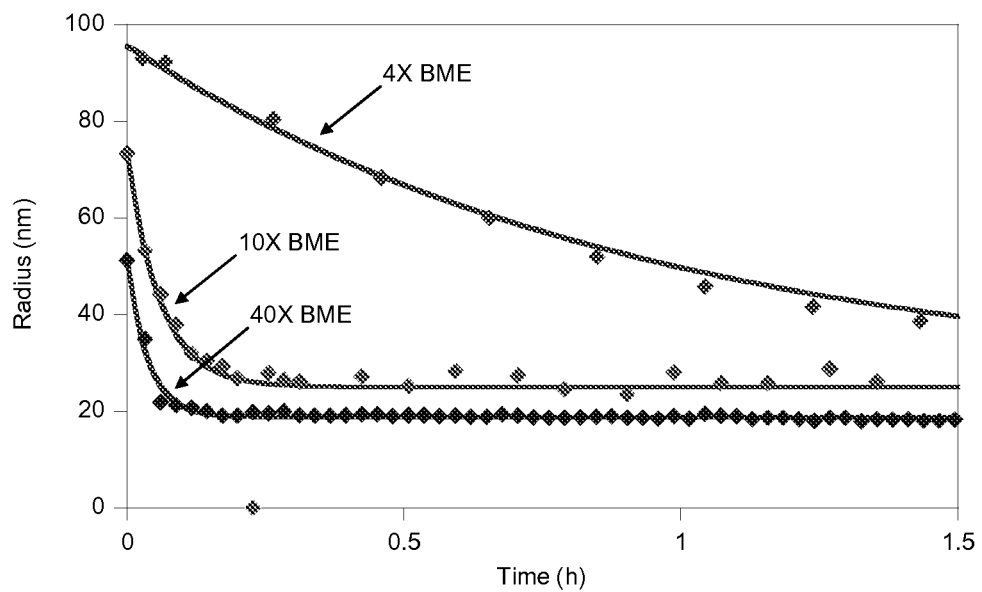
FIG. 10 is a DLS plot showing the rate of capsid formation at 4×BME, 10×BME, and 40×BME.

As shown in FIG. 10, increasing concentrations of β-mercaptoethanol (BME) were added to the siRNA protein solution (i.e., 4×, 10×, and 40×BME). The rate of capsid formation was measured using dynamic light scattering where the radius of the capsid was measured over time. The data show that the rate of cage formation is dependent upon the concentration of BME in the solution. At 4×BME, assembled capsids formed at a $t_{1/2}$ of 42.9 minutes; at 10×BME, at a $t_{1/2}$ of 2.5 minutes; and at 40×BME, $t_{1/2}$ of 1.6 minutes.

TABLE 5

| | 4X $y = m1 + m2*exp(-m3*x)$ | | | 10X $y = m1 + m2*exp(-m3*x)$ | | | 40X $y = m1 + m2*exp(-m3*x)$ | |
|---|---|---|---|---|---|---|---|---|
| | Value | Error | | Value | Error | | Value | Error |
| m1 | 23.876 | 0.080147 | m1 | 25.008 | 1.5874 | m1 | 18.769 | 0.10072 |
| m2 | 68.747 | 0.67357 | m2 | 78.539 | 14.606 | m2 | 33.012 | 0.7372 |
| m3 | 1.0311 | 0.017611 | m3 | 16.819 | 3.8046 | m3 | 26.912 | 1.2126 |
| chisq | 179.1 | NA | chisq | 748.35 | NA | chisq | 31.544 | NA |
| R2 | 0.98883 | NA | R2 | 0.80237 | NA | R2 | 0.97571 | NA |

The results in Table 5 and FIG. 10 indicate that rate of capsid assembly increases with increasing BME concentration.

Figure 11:
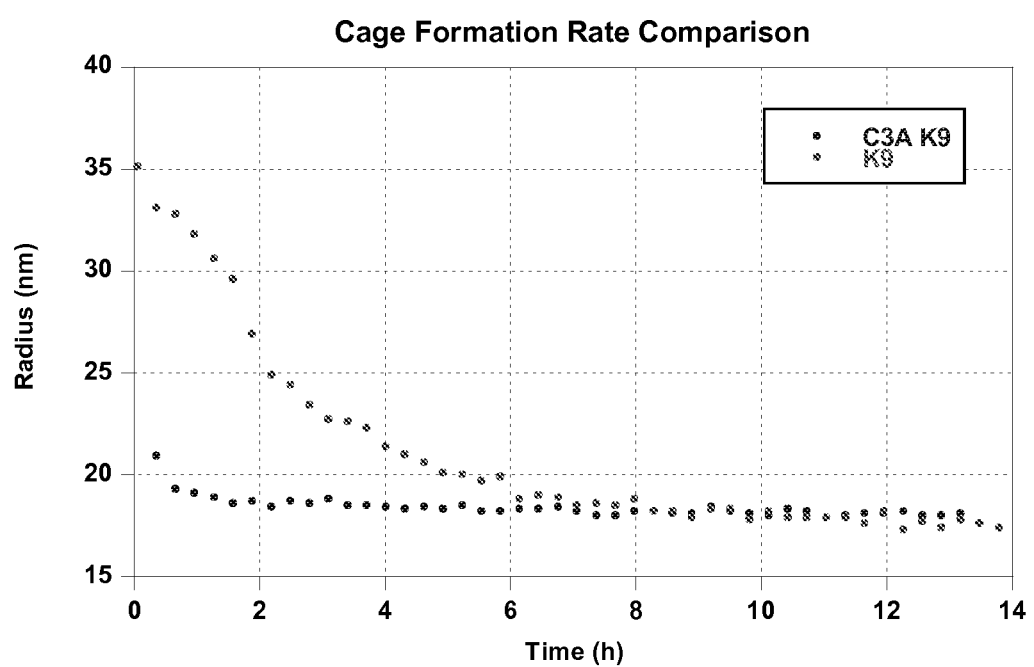
FIG. 11 is a DLS plot showing the rate of viral capsid formation between a modified HBV core protein with a poly-lysine tail (e.g., a K9 tail) portion (lighter points) and a modified HBV core protein with C48A, C61A, and C107A mutations in a SEQ ID NO: 2 variant and a poly-lysine tail (e.g., a K9 tail) portion (darker points).

The rate of capsid formation was also affected by the presence of certain mutations in the modified HBV core protein. As shown in FIG. 11, modified HBV core proteins, e.g., CP149 with E77C, C48A, C61A, and C107A mutations with a K9 tail (SEQ ID NO: 75) formed capsids faster than modified HBV core proteins with a E77C mutation and a K9 tail (SEQ ID NO: 62). Both modified HBV core proteins were based on a SEQ ID NO: 2 variant.

INCORPORATION BY REFERENCE

All publications and patents mentioned herein, including those items listed below, are hereby incorporated by reference in their entirety as if each individual publication or patent was specifically and individually incorporated by reference. In case of conflict, the present application, including any definitions herein, will control.

U.S. Pat. No. 7,964,196; US Patent Publication Nos. US2007-0269370 and 2009-0226525; and PCT Patent Application Publication No. WO2010/120874.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. All changes which come within the meaning and range of equivalency of the claims are to be embraced within their scope.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The terms "a" and "an" and "the" used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A method for assembling a modified Hepatitis B Virus (HBV) core protein into a capsid structure, the method comprising:
   providing a solution comprising a modified HBV core protein comprising a spike region and a first concentration of a denaturing agent, wherein the spike region of the modified HBV core protein comprises a cysteine residue at a position selected from 74 to 84 of SEQ ID NO: 1 or 2, and the modified HBV core protein optionally comprises one or more additional modifications in SEQ ID NO: 1 or 2; and
   adding a reducing agent to the solution, wherein the concentration of the reducing agent is from about 0.1 molar equivalent to about 100 molar equivalent, thereby to form an assembled capsid structure.

2. The method of claim 1, wherein the modified HBV core protein comprises a cysteine at amino acid position 77, 79 or 80 of SEQ ID NO: 1 or SEQ ID NO: 2.

3. The method of claim 1, wherein the modified HBV core protein comprises a cysteine at amino acid position 77 of SEQ ID NO: 1 or SEQ ID NO: 2.

4. The method of claim 1, wherein the reducing agent is at least one of beta-mercaptoethanol (BME), tris(2-carboxyethyl)phosphine (TCEP), glutathione (GSH), dithiothreitol (DTT), 2-mercaptoyethylamine (BMA) and free cysteine.

5. The method of claim 1, further comprising diluting the first concentration of denaturing agent to a second concentration thereby to form an assembled capsid.

6. The method of claim 5, wherein the first concentration of denaturing agent is diluted to a second concentration prior to, during, or after addition of the reducing agent.

7. The method of claim 5, wherein the second concentration of denaturing agent following the dilution step is from about 0.25 M to about 4 M.

8. The method of claim 5, further comprising adding a drug to the solution prior to the dilution step.

9. The method of claim 8, wherein the drug is bound to the amino acid tail portion of the HBV core protein and encapsulated in the capsid structure following the dilution step, or encapsulated in the capsid structure by diffusion following the dilution step.

10. The method of claim 8, wherein the drug is selected from the group consisting of a nucleic acid, a peptide, a protein, and a small molecule.

11. The method of claim 1, further comprising adding a negatively-charged polymer to the solution, wherein the polymer is added prior to addition of the reducing agent.

12. The method of claim 1, wherein the pH of the solution is about pH 7.0 or lower prior to addition of the reducing agent.

13. The method of claim 1, further comprising adding a drug to the solution, wherein the drug is added prior to, during, or after addition of the reducing agent.

14. The method of claim 13, wherein the drug binds to the amino acid tail portion of the modified HBV core protein.

15. The method of claim 13, wherein the drug is encapsulated in the capsid structure by diffusion following addition of the reducing agent or bound to the amino acid tail portion and encapsulated in the capsid structure following addition of the reducing agent.

16. The method of claim 15, wherein the drug is selected from the group consisting of a nucleic acid, a peptide, a protein, and a small molecule.

17. The method of claim 1, wherein the denaturing agent is at least one of urea, guanidinium hydrochloride (GuHC1), guanidinium thiocyanate (GITC), methanol, ethanol, trifluoroethanol (TFE), acetonitrile, and lithium perchloride.

18. The method of claim 1, wherein the first concentration of denaturing agent is from about 2 M to about 8 M.

19. The method of claim 1, wherein the modified HBV core protein is a C-terminal truncation mutant.

20. The method of claim 19, wherein one to four arginine-rich repeats are truncated from the carboxyl-terminus of the modified HBV core protein.

21. The method of claim 19, wherein the C-terminal truncation mutant comprises a 13 amino acid C-terminal truncation, a 21 amino acid C-terminal truncation, a 28 amino acid C-terminal truncation or a 34 amino acid C-terminal truncation.

22. The method of claim 1, wherein the modified HBV core protein further comprises a modified carboxyl-terminal amino acid tail portion.

23. The method of claim 22, wherein the amino acid tail portion is a synthetic tail portion.

24. The method of claim 22, wherein the amino acid tail portion is positively charged.

25. The method of claim 24, wherein the positively-charged amino acid tail portion is at least one of a lysine-rich tail portion and an arginine-rich tail portion.

26. The method of claim 25, wherein the lysine-rich tail portion comprises at least one of from about 4 to about 30 lysines and a lysine domain of about 4 to about 30 lysines.

27. The method of claim 26, wherein the lysine domain is about 9 lysines.

28. The method of claim 1, further comprising at least one of measuring the formation of the assembled capsid structure and purifying the assembled capsid structure.

29. The method of claim 1, wherein the modified HBV core protein is a CP162 mutant comprising a F18H mutation and an E77C mutation.

30. The method of claim 1, wherein the modified HBV core protein is a CP149 mutant comprising a F18H mutation, an E77C mutation, and the C-terminal tail is replaced with 9 lysines (K9).

31. The method of claim 1, wherein the modified HBV core protein is a CP162 mutant comprising an F18H mutation, an S121C mutation, a S141C mutation and an E77C mutation.

32. The method of claim 1, wherein the modified HBV core protein is a CP149 mutant comprising a F18H mutation, an S121C mutation, an S141C mutation and an E77C mutation, and the C-terminal tail is replaced with 9 lysines (K9).

* * * * *